United States Patent
Brugger et al.

(10) Patent No.: US 9,708,321 B2
(45) Date of Patent: Jul. 18, 2017

(54) SPIRO-QUINAZOLINONE DERIVATIVES AND THEIR USE AS POSITIVE ALLOSTERIC MODULATORS OF MGLUR4

(71) Applicant: Merck Patent GmbH, Darmstadt (DE)

(72) Inventors: Nadia Brugger, Cambridge, MA (US); Brian L. Hodous, Cambridge, MA (US); Amanda E. Sutton, Hingham, MA (US); Justin Potnick, Acton, MA (US); Theresa L. Johnson, Salem, MA (US); Thomas E. Richardson, Durham, NC (US); Thomas Francis Nelson Haxell, Morrisville, NC (US); James M. Dorsey, Durham, NC (US); Robert James Foglesong, Durham, NC (US)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/765,615

(22) PCT Filed: Jan. 23, 2014

(86) PCT No.: PCT/EP2014/000169
§ 371 (c)(1),
(2) Date: Aug. 4, 2015

(87) PCT Pub. No.: WO2014/117920
PCT Pub. Date: Aug. 7, 2014

(65) Prior Publication Data
US 2015/0361079 A1    Dec. 17, 2015

Related U.S. Application Data

(60) Provisional application No. 61/760,367, filed on Feb. 4, 2013.

(51) Int. Cl.
| | | |
|---|---|---|
| *C07D 471/10* | (2006.01) | |
| *C07D 239/91* | (2006.01) | |
| *C07D 487/10* | (2006.01) | |
| *A61K 31/4747* | (2006.01) | |
| *A61K 31/527* | (2006.01) | |
| *A61K 31/537* | (2006.01) | |
| *C07D 498/10* | (2006.01) | |

(52) U.S. Cl.
CPC ........ *C07D 471/10* (2013.01); *A61K 31/4747* (2013.01); *A61K 31/527* (2013.01); *A61K 31/537* (2013.01); *C07D 239/91* (2013.01); *C07D 487/10* (2013.01); *C07D 498/10* (2013.01)

(58) Field of Classification Search
CPC .. C07D 471/10; C07D 498/10; C07D 239/91; C07D 487/10; A61K 31/4747; A61K 31/527; A61K 31/537
See application file for complete search history.

(56) References Cited

U.S. PATENT DOCUMENTS

| | | | | |
|---|---|---|---|---|
| 3,714,093 | A * | 1/1973 | Wolf | .................... C07D 471/10 544/231 |
| 5,633,247 | A * | 5/1997 | Baldwin | .............. C07D 221/20 514/210.2 |
| 7,498,323 | B2 | 3/2009 | Nishizawa | |
| 8,618,132 | B2 | 12/2013 | Stenkamp | |
| 9,173,864 | B2 * | 11/2015 | Friedman | ............. A61K 9/0046 |
| 2010/0113418 | A1 | 5/2010 | Fukatsu | |
| 2013/0065895 | A1 | 3/2013 | Conn et al. | |
| 2013/0096110 | A1 | 4/2013 | Conn et al. | |

FOREIGN PATENT DOCUMENTS

| | | | |
|---|---|---|---|
| EP | 2311840 | A1 | 4/2011 |
| JP | 48-67287 | * | 9/1973 |
| WO | 2004/022554 | A1 | 3/2004 |
| WO | 2004/039780 | A1 | 5/2004 |
| WO | 2004/092169 | A1 | 10/2004 |
| WO | 2008/102749 | A1 | 8/2008 |
| WO | 2009/127609 | A1 | 10/2009 |
| WO | 2010/008521 | A1 | 1/2010 |
| WO | 2010/094120 | A1 | 8/2010 |
| WO | 2011/047481 | A1 | 4/2011 |
| WO | 2011/100607 | A1 | 8/2011 |
| WO | 2011/143444 | A2 | 11/2011 |

OTHER PUBLICATIONS

Esakkirajan, M., "Anti-proliferative effect of a compound isolated from Cassia auriculata against human colon cancer cell line HCT 15." Spectrochimica Acta Part A: Molecular and Biomolecular Spectroscopy 120 (2014): 462-466.*
Amalric, M.,"Group III and subtype 4 metabotropic glutamate receptor agonists: discovery and pathophysiological applications in Parkinson's disease." Neuropharmacology 66 (2013): 53-64.*
Hirose, N., "Studies on Benzoheterocyclic Derivatives. XIV. Synthesis of Spiro [cycloalkane-1', 2 (1H) quinazolin]-4 (3H)-ones and the Related Compounds." Chemical and Pharmaceutical Bulletin 21.5 (1973): 1005-1013.*
Célanire, S., "Recent advances in the drug discovery of metabotropic glutamate receptor 4 (mGluR4) activators for the treatment of CNS and non-CNS disorders." Expert opinion on drug discovery 7.3 (2012): 261-280.*
International Search Report dated Mar. 10, 2014 issued in corresponding PCT/EP2014/000169 application (pp. 1-4).
X.S. Wang et al. "Facile Method for the Combinatorial Synthesis of 2,2-Disubstituted Quinazolin-4(1H)-one Derivatives Catalyzed by Iodine in Ionic Liquids", Journal of Combinatorial Chemistry, vol. 12, No. 4 (Mar. 24, 2010) pp. 417-421.
H.L. Birch et al., "Novel 7-methoxy-6-oxazol-5-yl-2,3-dihydro-1H-quinazolin-4-ones as IMPDH Inhibitors", Bioorganic & Medicinal Chemistry Letters, vol. 15, No. 23 (2005) pp. 5335-5339.

(Continued)

*Primary Examiner* — Samantha Shterengarts
*Assistant Examiner* — Matt Mauro
(74) *Attorney, Agent, or Firm* — Millen, White, Zelano, Branigan, P.C.

(57) ABSTRACT

The present invention relates to novel spiro-quinazolinone derivatives as positive allosteric modulators for modulating metabotropic glutamate receptor subtype 4 (mGluR4) and/or altering glutamate level or glutamatergic signalling.

21 Claims, No Drawings

(56) References Cited

OTHER PUBLICATIONS

M. Yamato et al., "Synthesis and Structure-Activity Relationship of Spiro[isochroman-piperidine] Analogs for Inhibition of Histamine Release. II", Chemical and Pharmaceutical Bulletin, vol. 29, No. 12 (1981) pp. 3494-3498.
Shetty BV et al. (J. Med. Chem. 1970, 13(5): 886-895).
Uitsuoka M et al. (Bioorg. Med. Chem. Let. 2008, 18: 5101-5106).
Chen G et al. (Med. Chem. Commun. 2011, 2: 315-320).
Sharma M et al. (J. Org. Chem. 2012, 77: 929-937).
Pessimissis N et al., Anticancer Res. 29(1 ), 371-7, 2009.
Chang HJ et al., Clin. Cancer Res. 1 1 (9), 3288-95, 2005.
Iacoveili L et al., J. Neurosci. 26(32) 8388-97, 2006.
Eschle BK., Neuroscience, 155(2), 522-9, 2008.
Mustazza C et al. (Chem Pharm Bull 2006, 54(5): 611-622).
Hirose N et al. (Chem Pharm Bull 1973, 21(5): 1005-1013).
Yamato M et al. (Chem Pharm Bull 1980, 28(9): 2623-2628).
Takai H et al. (Chem Pharm Bull 1985, 33(3): 1116-1128).
Yamato M et al. (Heterocycles 1987, 26(1): 191-197).

* cited by examiner

SPIRO-QUINAZOLINONE DERIVATIVES AND THEIR USE AS POSITIVE ALLOSTERIC MODULATORS OF MGLUR4

TECHNICAL FIELD

The present invention relates to novel spiro-quinazolinone derivatives as positive allosteric modulators for modulating metabotropic glutamate receptor subtype 4 (mGluR4) and/or altering glutamate level or glutamatergic signalling.

PRIOR ART

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res. Rev., 26:230-235).

In addition, glutamate activates metabotropic glutamate receptors (mGluRs) which have a more modulatory role that contributes to the fine-tuning of synaptic efficacy. The mGluRs are G protein-coupled receptors (GPCRs) with seven-transmembrane spanning domains and belong to GPCR family 3 along with the calcium-sensing, GABAb and pheromone receptors. The mGluR family is composed of eight members. They are classified into three groups (group I comprising mGluR1 and mGluR5; group II comprising mGluR2 and mGluR3; group III comprising mGluR4, mGluR6, mGluR7 and mGluR8) according to sequence homology, pharmacological profile and nature of intracellular signalling cascades activated (Schoepp et al., (1999) Neuropharmacology, 38: 1431-1476).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

In the central nervous system, mGluR4 receptors are expressed most intensely in the cerebellar cortex, basal ganglia, sensory relay nuclei of the thalamus and hippocampus (Bradley et al., (1999) Journal of Comparative Neurology, 407:33-46; Corti et al., (2002) Neuroscience, 1 10:403-420). The mGluR4 subtype is negatively coupled to adenylate cyclase via activation of the Gori/o protein, is expressed primarily on presynaptic terminals, functioning as an autoreceptor or heteroreceptor and activation of mGluR4 leads to decreases in transmitter release from presynaptic terminals (Corti et al., (2002) Neuroscience, 1 10:403-420; Millan et al., (2002) Journal of Biological Chemistry, 277: 47796-47803; Valenti et al., (2003) Journal of Neuroscience, 23:7218-7226).

Orthosteric agonists of mGluR4 are not selective and activate the other Group III mGluRs (Schoepp et al., (1999) Neuropharmacology, 38: 1431-1476). The Group III orthosteric agonist L-AP4 (L-2-amino-4-phosphonobutyrate) was able to reduce motor deficits in animal models of Parkinson's disease (Valenti et al., (2003) J. Neurosci., 23:7218-7226) and decrease excitotoxicity (Bruno et al., (2000) J. Neurosci., 20; 6413-6420) and these effects appear to be mediated through mGluR4 (Marino et al., (2005) Curr. Topics Med. Chem., 5:885-895). In addition to L-AP4, ACPT-1, another selective group III mGluR agonist has been shown to caused a dose and structure-dependent decrease in haloperidol-induced catalepsy and attenuated haloperidol-increased Proenkephalin mRNA expression in the striatum (Konieczny et al., (2007) Neuroscience, 145:61 1-620). Furthermore, Lopez et al. (2007, J. Neuroscience, 27:6701-671 1) have shown that bilateral infusions of ACPT-l or L-AP4 into the globus pallidus fully reversed the severe akinetic deficits produced by 6-hydroxydopamine lesions of nigrostriatal dopamine neurons in a reaction-time task without affecting the performance of controls. In addition, the reversal of haloperidol-induced catalepsy by intrapallidal ACPT-1 was prevented by concomitant administration of a selective group III receptor antagonist (R5)-alpha-cyclopropyl-4-phosphonophenylglycine. The opposite effects produced by group III mGluR activation in the SNr strongly suggest a role of mGluR4 rather than others mGluR receptor sub-types in normalizing basal ganglia activity (Lopez et al. 2007).

These results suggest that, among mGluR subtypes, mGluR4 is believed to be the most interesting novel drug target for the treatment of Parkinson's disease (for a review see Conn et al., (2005) Nature Review Neuroscience, 6:787-798). Symptoms of Parkinson's disease appear to be due to an imbalance in the direct and indirect output pathways of the basal ganglia, and reduction of transmission at the inhibitory GABAergic striato-pallidal synapse in the indirect pathway may result in alleviation of these symptoms (Marino et al., (2002) Amino Acids, 23: 185-191). mGluR4 is more abundant in striato-pallidal synapses than in striato-nigral synapses, and its localization suggests function as a presynaptic heteroreceptor on GABAergic neurons (Bradley et al., (1999) Journal of Comparative Neurology, 407:33-46) suggesting that selective activation or positive modulation of mGluR4 would decrease GABA release in this synapse thereby decreasing output of the indirect pathway and reducing or eliminating the Parkinson's disease symptoms. Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism. These molecules have the same side-effect profile as levodopa.

The common end point of Parkinson's disease (PD) pathology is a progressive degeneration of the dopaminergic neurons located in the pars compacta of the substantia nigra (SNpc) that project and release dopamine into the striatum. PD symptoms usually appear when more than 60% of SNpc neurons have already disappeared. This results in profound movements disturbances including rest tremor, rigidity and stiffness, gait and balance control dysfunctions and dementia that dramatically deteriorate patients and family quality of life.

Current treatments aim at substituting the missing dopamine or mimicking its effects by chronically providing patients with the dopamine precursor L-DOPA, inhibitors of dopamine catabolic enzymes (MAO inhibitors) or direct dopamine receptors agonists. Although these treatments proved relatively efficient in controlling the main symptoms of PD, their chronic administration is associated with serious side effects. For example, the efficacy of L-DOPA following few years of treatment invariably tends to diminish in intensity and stability leading to uneven on/off periods that require an increase in dosing. In addition, chronic administration of high doses of L-DOPA is associated with the occurrence of involuntary movements (dyskinesia) that are usually overcome by combining a reduction in the dose of L-DOPA with other dopaminergic agents. Yet, massive supply of dopamine in the brain has also been associated with psychiatric disturbances including depression, psychotic symptoms, obsessive behaviours sleep disturbances etc. Finally, none of the compounds of the current pharmacopeia for PD have demonstrated neuroprotective activity that would delay disease progression. Therefore, to address these important unmet medical needs, efforts are required to develop new treatments for PD that target the neurochemical systems downstream dopamine itself.

The control of movements by dopamine in healthy subjects follows a complex pattern of neurochemical systems and brain structures interactions (Wichmann and Delong, 2003, Adv Neurol 91:9-18). The basal ganglia that is composed mainly of the substantia nigra (SN), and the striatal and thalamic complex constitutes the cornerstone of these interactions. The internal capsule of the globus pallidus (GPi) and SN pars reticulata (SNpr) fulfil the roles of relays between cortical areas that directly control movements and the basal ganglia itself. GPi and SNpr receive both an inhibitory direct connection (direct pathway) and an excitatory indirect input (indirect pathway) from the basal ganglia. Both pathways are modulated by dopamine with opposite valence so that the direct pathway is stimulated while the indirect pathway is inhibited by dopamine. Consequently in the diseased brain, the lack of dopamine leads to a dysregulation of the output activity of both the direct and indirect pathways. In particular, the indirect pathway gets overactivated, which is reflected by increased GABA release into the globus pallidus external segment (GPe). Consequently, glutamate release is increased in the SN pars compacta (SNpc), GPi and SNpr. These distortions of the balance of neurotransmission in the direct and indirect pathways are believed to result in movement control abnormalities and the precipitation of neurodegeneration of dopaminergic neurons. Fine analysis of these pathways provided insights on the possibility to target neurochemical pathways downstream dopamine to restore its function in the PD brain without interfering directly with it. In particular, metabotropic glutamate receptors (mGluRs) have been shown to modulate neurotransmitter release at the presynaptic level. Specifically, the subtype 4 of mGluR (mGluR4) predominantly expressed in the brain in discrete areas was demonstrated to dampen glutamate and GABA neurotransmissions at the subthalamic nucleus (STN)—SNpc (Valenti O et al., 2005, J Pharmacol Exp Ther 313:1296-1304) and striatum—GPe (Valenti O et al., 2003, J Neurosci 23:7218-7226) synapses, respectively. Evidence suggests that inhibition was achieved through presynaptic mechanisms providing a functional confirmation of the observed presynaptic receptor localization (Corti et al., 2002, Neuroscience 110:403-420; Schoepp, 2001, J Pharmacol Exp Ther 299:12-20).

Furthermore, behavioural analyses confirmed the beneficial effects of stimulation of mGluR4 in both chronic and acute rat models of PD. For example, the cataleptic behaviour observed following haloperidol administration and reserpine-induced immobility were both reversed by the positive allosteric modulator (PAM) VU0155041 (Niswender et al., 2008, Mol Pharmacol 74:1345-1358). Both models mimic key features of the human disease that are rigidity and akinesia, respectively. Finally, the increased release of glutamate is believed to participate, at least in part, in the degeneration of the remaining dopaminergic neurons whereby worsening the condition and reducing treatment efficacy. Hence, the mGluR4 positive allosteric modulator (PAM) PHCCC, which reduces glutamate release, also protects neurons from further degenerating in rats treated with the neurotoxin 6-hydroxydopamine (6-OHDA) that selectively destroys dopaminergic neurons (Vernon 2009, J Neurosci 29: 12842-12844). Altogether these results suggest that stimulation of mGluR4 has great potential to alleviate PD symptoms in patient and provide neuroprotection to the remaining neurons.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, mGluR5, mGluR7 and mGluR8 (Knoflach F. et al. (2001) Proc. Natl. Acad. Sci. USA, 98: 13402-13407; Johnson M. P. et al., (2002) Neuropharmacology, 43:799-808; O'Brien J. A. et al., (2003) Mol. Pharmacol., 64:731-740; Johnson M. P. et al, (2003) J. Med. Chem., 46:3189-3192; Marino M. J. et al., (2003) Proc. Natl. Acad. Sci. USA, 100: 13668-13673; Mitsukawa et al., (2005) Proc. Natl. Acad. Sci. USA, 102(51): 18712-18717; Wilson J. et al., (2005) Neuropharmacology, 49:278; for a review see Mutel V., (2002) Expert Opin. Ther. Patents, 12: 1-8; Kew J. N., (2004) Pharmacol. Ther., 104(3):233-244; Johnson M. P. et al., (2004) Biochem. Soc. Trans., 32:881-887; recently Ritzen A., Mathiesen, J. M. and Thomsen C, (2005) Basic Clin. Pharmacol. Toxicol., 97:202-213).

In particular molecules have been described as mGluR4 positive allosteric modulators (Maj et al., (2003) Neuropharmacology, 45:895-906; Mathiesen et al., (2003) British Journal of Pharmacology, 138: 1026-1030). It has been demonstrated that such molecules have been characterized in in vitro systems as well as in rat brain slices where they potentiated the effect of L-AP4 in inhibiting transmission at the striatopallidal synapse. These compounds do not activate the receptor by themselves (Marino et al., (2003) Proc. Nat. Acad. Sci. USA, 100: 13668-13673). Rather, they enable the receptor to produce a maximal response to a concentration of glutamate or the Group III orthosteric agonist L-AP4 which by itself induces a minimal response.

PHCCC (N-phenyl-7-(hydroxyimino)cyclopropa[6]chromen-la-carboxamide), a positive allosteric modulator of mGluR4 not active on other mGluRs (Maj et al., (2003) Neuropharmacology, 45:895-906), has been shown to be efficacious in animal models of Parkinson's disease thus representing a potential novel therapeutic approach for Parkinson's disease as well as for other motor disorders and disturbances (Marino et al., (2003) Proc. Nat. Acad. Sci. USA, 100: 13668-13673), neurodegeneration in Parkinson's disease (Marino et al., (2005) Curr. Topics Med. Chem., 5:885-895; Valenti et al., (2005) J. Pharmacol. Exp. Ther., 313: 1296-1304; Vernon et al., (2005) Eur. J. Neurosci., 22: 1799-1806, Battaglia et al., (2006) J. Neurosci., 26:7222-7229), and neurodegeneration in Alzheimer's disease or due to ischemic or traumatic insult (Maj et al., (2003) Neuropharmacology, 45:895-906).

PHCCC also has been shown to be active in an animal model of anxiety (Stachowicz et al., (2004) Eur. J. Pharmacol., 498: 153-156). Previously, ACPT-1 has been shown to produce a dose-dependent anti-conflict effect after intrahippocampal administration and anti-depressant-like effects in rats after intracerebroventricular administration (Tatarczynska et al., (2002) Pol. J. Pharmacol., 54(6):707-710). More recently, ACPT-1 has also been shown to have anxiolytic-like effects in the stress-induced hyperthermia, in the elevated-plus maze in mice and in the Vogel conflict test in rats when injected intraperitoneally (Stachowicz et al., (2009) Neuropharmacology, 57(3): 227-234).

Activation of mGluR4 receptors which are expressed in a- and F-cells in the islets of Langerhans inhibits glucagon secretion. Molecules which activate or potentiate the agonist activity of these receptors may be an effective treatment for hyperglycemia, one of the symptoms of type 2 diabetes (Uehara et al., (2004) Diabetes, 53:998-1006).

The [beta]-chemokine RANTES is importantly involved in neuronal inflammation and has been implicated in the pathophysiology of multiple sclerosis. Activation of Group III mGluRs with L-AP4 reduced the synthesis and release of RANTES in wild-type cultured astrocytes, whereas the ability of L-AP4 to inhibit RANTES was greatly decreased in astrocyte cultures from mGluR4 knockout mice (Besong et al., (2002) Journal of Neuroscience, 22:5403-541 1). These data suggest that positive allosteric modulators of mGluR4 may be an effective treatment for neuroinflammatory disorders of the central nervous system, including multiple sclerosis and related disorders.

Two different variants of the mGluR4 receptor are expressed in taste tissues and may function as receptors for the umami taste sensation (Monastyrskaia et al., (1999) Br. J Pharmacol., 128: 1027-1034; Toyono et al., (2002) Arch. Histol. Cytol., 65:91-96). Thus positive allosteric modulators of mGluR4 may be useful as taste agents, flavour agents, flavour enhancing agents or food additives.

There is anatomical evidence that the majority of vagal afferents innervating gastric muscle express group III mGluRs (mGluR4, mGluR6, mGluR7 and mGluR8) and actively transport receptors to their peripheral endings (Page et al., (2005) Gastroenterology, 128:402-10). Recently, it was shown that the activation of peripheral group III mGluRs inhibited vagal afferents mechanosensitivity in vitro which translates into reduced triggering of transient lower esophageal sphincter relaxations and gastroesophageal reflux in vivo (Young et al., (2008) Neuropharmacol, 54:965-975). Labelling for mGluR4 and mGluR8 was abundant in gastric vagal afferents in the nodose ganglion, at their termination sites in the nucleus tractus solitarius and in gastric vagal motoneurons. These data suggest that positive allosteric modulators of mGluR4 may be an effective treatment for gastroesophageal reflux disease (GERD) and lower esophageal disorders and gastro-intestinal disorders.

For groups III mGluRs, examples of allosteric modulators were so far described for the mGluR subtype 4 (mGluR4). PHCCC, MPEP and S1B1893 (Maj M et al., Neuropharmacology, 45(7), 895-903, 2003; Mathiesen J M et al., Br. J, Pharmacol. 138(6), 1026-30, 2003) were the first ones described in 2003. More recently, more potent positive allosteric modulators were reported in the literature (Niswender C M et al., Mol. Pharmacol. 74(5), 1345-58, 2008; Niswender C M et al., Bioorg. Med. Chem. Lett 18(20), 5626-30, 2008; Williams R et al., Bioorg. Med. Chem. Lett. 19(3), 962-6, 2009; Engers D W et al., J. Med. Chem. May 27 2009) and in two patent publications describing families of amido and heteroaromatic compounds (WO 2009/010454 and WO 2009/010455).

Numerous studies have already described the potential applications of mGluR modulators in neuroprotection (see Bruno V et al., J. Cereb. Blood Flow Metab., 21 (9), 1013-33, 2001 for review). For instance, antagonist compounds of group I mGluRs showed interesting results in animal models for anxiety and postischemic neuronal injury (Pile A et al., Neuropharmacology, 43(2), 181-7, 2002; Meli E et al., Pharmacol. Biochem. Behav., 73(2), 439-46, 2002), agonists of group II mGluRs showed good results in animal models for Parkinson and anxiety (Konieczny J et al., Naunyn-Schmlederbergs Arch. Pharmacol., 358(4), 500-2, 1998).

Group III mGluR modulators showed positive results in several animal models of schizophrenia (Paiucha-Poniewiera A et al., Neuropharmacology, 55(4), 517-24, 2008) and chronic pain (Goudet C et al., Pain, 137(1), 1 12-24, 2008; Zhang H M et al., Neuroscience, 158(2), 875-84, 2009).

Group III mGluR were also shown to exert the excitotoxic actions of homocysteine and homocysteic acid contributing to the neuronal pathology and immunosenescence that occur in Alzheimer Disease (Boldyrev A A and Johnson P, J. Alzheimers Dis. 1 (2), 219-28, 2007).

Moreover, group III mGluR modulators showed promising results in animal models of Parkinson and neurodegeneration (Conn J et al., Nat Rev. Neuroscience, 6(10), 787-98, 2005 for review; Vernon A C et al., J. Pharmacol. Exp. Then, 320(1), 397-409, 2007; Lopez S et al., Neuropharmacology, 55(4), 483-90, 2008; Vernon A C et al., Neuroreport, 19(4), 475-8, 2008). It was further demonstrated with selective ligands that the mGluR subtype implicated in these antiparkinsonian and neuroprotective effects was mGluR4 (Marino M J et al., Proc. Natl. Acad. Sci. USA 100(23), 13668-73, 2003; Battaglia G et al., J. Neurosci. 26(27), 7222-9, 2006; Niswender C M et al., Mol. Pharmacol. 74(5), 1345-58, 2008).

mGluR4 modulators were also shown to exert anxiolytic activity (Stachowicz K et al., Eur. J. Pharmacol., 498(1-3), 153-6, 2004) and anti-depressive actions (Palucha A et al., Neuropharmacology 46(2), 151-9, 2004; Klak K et al., Amino Acids 32(2), 169-72, 2006).

In addition, mGluR4 were also shown to be involved in glucagon secretion inhibition (Uehara S., Diabetes 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (Pessimissis N et al., Anticancer Res. 29(1), 371-7, 2009) or colorectal carcinoma (Chang H J et al., CIL Cancer Res. 11 (9), 3288-95, 2005) and its activation with PHCCC was shown to inhibit growth of medulloblastomas (lacoveili L et al., J. Neurosci. 26(32) 8388-97, 2006), mGluR4 modulators may therefore have also potential role for the treatment of cancers.

Finally, receptors of the umami taste expressed in taste tissues were shown to be variants of the rnGiuR4 receptor (Eschle B K., Neuroscience, 155(2), 522-9, 2008). As a consequence, mGluR4 modulators may also be useful as taste agents, flavour agents, flavour enhancing agents or food additives.

Further prior art documents are as follows:

Shetty B V et al. (J. Med. Chem. 1970, 13(5): 886-895) describe the synthesis and activity of certain (spiro)quinazolinesulfonamides.

Hirose N et al. (Chem Pharm Bull 1973, 21(5): 1005-1013) describe studies on spiro-cycloalkane-quinazolin derivatives.

U.S. Pat. No. 3,714,093 discloses spiro-heterocycloalkyl-quinazolinone derivatives.

Yamato M et al. (Chem Pharm Bull 1980, 28(9): 2623-2628) describe the reaction of spiro-piperidine-quinazolin derivatives with acid anhydrides.

Yamato M et al. (Chem Pharm Bull 1981, 29(12): 3494-3498) describe the synthesis and structure-activity relationship of spiro-isochroman-piperidine derivatives.

Takai H et al. (Chem Pharm Bull 1985, 33(3): 1116-1128) describes the synthesis of (spiro)2-oxoquinazoline derivatives as potential antihypertensive agents.

Yamato M et al. (Heterocycles 1987, 26(1): 191-197) describe the reaction of spiro-piperidine-quinazoline derivatives with acetic acid.

WO 2004/022554 discloses quinazolinone derivatives.

WO 2004/039780 discloses novel alkyne compounds having an MCH antagonistic affect and medicaments containing these compounds.

WO 2004/092169 discloses spiro-piperidine compounds and medicinal use thereof.

Mustazza C et al. (Chem Pharm Bull 2006, 54(5): 611-622) describe the synthesis and evaluation as NOP ligands of some spiro-piperidine-quinazoline derivatives.

Jitsuoka M et al. (Bioorg. Med. Chem. Let. 2008, 18: 5101-5106) describe the synthesis and evaluation of a spiro-isobenzofuranone class of histamine H3 receptor inverse agonists.

WO 2008/102749 discloses heterocyclic compounds.

WO 2009/127609 discloses spirocyclic derivatives as histone deacetylase inhibitors.

Wang X S et al. (J. Comb. Chem. 2010, 12: 417-421) describe the combinatorial synthesis of 2,2-disubstituted quinazolinone derivatives.

WO 2010/008521 discloses modulators of acetylcoenzyme A carboxylase and methods of use thereof.

WO 2010/094120 discloses novel spiro compounds useful as inhibitors of stearoyl-coenzyme A delta-9 desaturase.

Chen G et al. (Med. Chem. Commun. 2011, 2: 315-320) describe diphenylbutylpiperidine-based cell autophagy inducers.

EP 2 311 840 discloses spirocyclic derivatives as histone deacetylase inhibitors.

WO 2011/047481 discloses novel spiro compounds useful as inhibitors of stearoyl-coenzyme A delta-9 desaturase.

WO 2011/143444 discloses diphenylbutylpiperidine autophagy inducers.

Sharma M et al. (J. Org. Chem. 2012, 77: 929-937) describe a cyanuric chloride catalyzed mild protocol for the synthesis of biologically active spiro-quinazolinone derivatives.

The citation of any reference in this application is not an admission that the reference is relevant prior art to this application.

DESCRIPTION OF THE INVENTION

The present invention has the object to provide novel spiro-quinazolinone derivatives.

The object of the present invention has surprisingly been solved in one aspect by providing compounds of formula (I)

(I)

wherein:
W denotes N, O or CH, preferably N;
X denotes N or CH;
R1 denotes alkyl, cycloalkyl, cycloalkylalkyl, heterocyclyl, heterocyclylalkyl, aryl, arylalkyl, heteroaryl, heteroarylalkyl, which can optionally be substituted by one or more identical or different substituents T;
R2 denotes $(NY)_p$-alkyl, $(NY)_p$-cycloalkyl, $(NY)_p$-cycloalkylalkyl, $(NY)_p$-heterocyclyl, $(NY)_p$-heterocyclylalkyl, $(NY)_p$-aryl, $(NY)_p$-arylalkyl, $(NY)_p$-heteroaryl, $(NY)_p$-heteroarylalkyl, $(NY)_p$—C(O)-alkyl, $(NY)_p$—C(O)-cycloalkyl, $(NY)_p$—C(O)-alkyl-cycloalkyl, $(NY)_p$—C(O)-heterocyclyl, $(NY)_p$—C(O)-alkyl-heterocyclyl, $(NY)_p$—C(O)-aryl, $(NY)_p$—C(O)-alkyl-aryl, $(NY)_p$—C(O)-heteroaryl, $(NY)_p$—C(O)-alkyl-heteroaryl, $(NY)_p$—C(O)O-alkyl, $(NY)_p$—C(O)O-cycloalkyl, $(NY)_p$—C(O)O-alkyl-cycloalkyl, $(NY)_p$—C(O)O-heterocyclyl, $(NY)_p$—C(O)O-alkyl-heterocyclyl, $(NY)_p$—C(O)O-aryl, $(NY)$—C(O)O-alkyl-aryl, $(NY)_p$—C(O)O-heteroaryl, $(NY)_p$—C(O)O-alkyl-heteroaryl, $(NY)_p$—C(O)NH-alkyl, $(NY)_p$—C(O)NH-cycloalkyl, $(NY)_p$—C(O)NH-alkyl-cycloalkyl, $(NY)_p$—C(O)NH-heterocyclyl, $(NY)_p$—C(O)NH-alkyl-heterocyclyl, $(NY)_p$—C(O)NH-aryl, $(NY)_p$—C(O)NH-alkyl-aryl, $(NY)_p$—C(O)NH-heteroaryl, $(NY)_p$—C(O)NH-alkyl-heteroaryl, $(NY)_p$—S(O)$_2$-alkyl, $(NY)_p$—S(O)$_2$-cycloalkyl, $(NY)_p$—S(O)$_2$-alkyl-cycloalkyl, $(NY)_p$—S(O)$_2$-heterocyclyl, $(NY)_p$—S(O)$_2$-alkyl-heterocyclyl, $(NY)_p$—S(O)$_2$-aryl, $(NY)_p$—S(O)$_2$-alkyl-aryl, $(NY)_p$—S(O)$_2$-heteroaryl, $(NY)_p$—S(O)$_2$-alkyl-heteroaryl, which can optionally be substituted by one or more identical or different substituents T;
R3 if W is N or CH, R3 denotes H or alkyl, cycloalkyl, cycloalkylalkyl, heterocyclyl, heterocyclylalkyl, aryl, arylalkyl, heteroaryl, heteroarylalkyl; which can optionally be substituted by one or more identical or different substituents T;
if W is O, R3 is absent;
R4, R5, independently from each other denote H, alkyl, aryl,
R6, R7 heteroaryl, cycloalkyl, heterocyclyl, halogen, F, Cl, Br, I, OH, CN, NO$_2$, NYY, CF$_3$, OCF$_3$, O-alkyl, O-alkyl-heterocyclyl, O-alkyl-aryl, O-alkyl-heteroaryl, O-alkyl-NYY, O-alkyl-O-alkyl, C(O)OY, C(O)NY-alkyl-NYY, C(O)NYY, C(O)-alkyl, C(O)-heterocyclyl, S(O)$_2$—Y; whereby alkyl, heterocyclyl, aryl, heteroaryl can optionally be substituted by one or more identical or different substituents T;
T denotes independently from each other H, alkyl, halogen, F, Cl, Br, I, OH, CN, NO$_2$, NYY, CF$_3$, OCF$_3$, O-alkyl, O-alkyl-heterocyclyl, alkyl-NYY, O-alkyl-aryl, O-alkyl-heteroaryl, O-alkyl-NYY, O-alkyl-O-alkyl, C(O)OY, C(O)NY-alkyl-NYY, C(O)NYY, S(O)$_2$—Y, S-alkyl; or two adjacent substituents T can also form together with the atoms to which they are attached to cycloalkyl or heterocyclyl;
Y denotes independently from each other H, alkyl, cycloalkyl, cycloalkylalkyl, aryl, arylalkyl, heteroaryl, heteroarylalkyl, alkyl-O-alkyl;
n, m independently from each other denote 1 or 2;
p denotes independently from each other 0 if X is N or denotes independently from each other 1 if X is CH;
and the physiologically acceptable salts, solvates, tautomers and stereoisomers thereof, including mixtures thereof in all ratios.

In a preferred embodiment, a compound according to formula (I) is provided, wherein:

n, m both denote 2;
and the physiologically acceptable salts, solvates, tautomers and stereoisomers thereof, including mixtures thereof in all ratios.

In a preferred embodiment, a compound according to formula (I) is provided, wherein:
n, m both denote 1;
and the physiologically acceptable salts, solvates, tautomers and stereoisomers thereof, including mixtures thereof in all ratios.

In a preferred embodiment, a compound according to formula (I) and above embodiments is provided, wherein:
X denotes N;
p denotes 0;
and the physiologically acceptable salts, solvates, tautomers and stereoisomers thereof, including mixtures thereof in all ratios.

In a preferred embodiment, a compound according to formula (I) and above embodiments is provided, wherein:
X denotes CH;
p denotes 1;
and the physiologically acceptable salts, solvates, tautomers and stereoisomers thereof, including mixtures thereof in all ratios.

In a preferred embodiment, a compound according to formula (I) and above embodiments is provided, wherein:
R1 denotes alkyl, preferably methyl, ethyl or propyl, or cycloalkyl, preferably cyclopropyl, or aryl, preferably phenyl, or heteroaryl, preferably pyridyl, thiazolyl, benzimidazole or benzofuranyl; which can optionally be substituted by one or more identical or different substituents T;
and the physiologically acceptable salts, solvates, tautomers and stereoisomers thereof, including mixtures thereof in all ratios.

In a preferred embodiment, a compound according to formula (I) and above embodiments is provided, wherein:
R1 denotes methyl, ethyl, methoxy-ethyl, 1-methoxy-ethan-2-yl, methoxy-propyl, 1-methoxy-propan-3-yl, cyclopropyl, phenyl, methyl-phenyl, 1-methyl-phen-4-yl, 1-methyl-phen-3-yl, hydroxy-phenyl, 1-hydroxy-phen-2-yl, 1-hydroxy-phen-3-yl, 1-hydroxy-phen-4-yl, methoxy-phenyl, 1-methoxy-phen-4-yl, 1-methoxy-phen-3-yl, 1-methoxy-phen-2-yl, fluoro-phenyl, 1-fluoro-phen-4-yl, fluoro-methoxy-phenyl, bromo-phenyl, 1-bromo-phen-4-yl, cyano-phenyl, 1-cyano-phen-4-yl, 1-methoxy-2-fluoro-phen-4-yl, pyridyl, pyridin-3-yl, methoxy-pyridyl, 2-methoxy-pyridin-5-yl, thiazolyl, thiazol-2-yl, benzimidazolyl, benzimidazol-2-yl, pyrazolyl, pyrazol-3-yl, methyl-pyrazolyl, 1-methyl-3-pyrazol-3-yl, methyl-benzofuranyl, 2-methyl-benzofuran-5-yl, dimethyl-aminoethyl, 1,1-dimethylaminoethan-2-yl, dimethyl-aminopropyl, 1,1-dimethylaminopropan-3-yl, dimethyl-aminoethoxy-phenyl, 1,1-dimethyl-aminoethoxy-phen-4-yl, methoxy-ethoxy-phenyl, 2-methoxy-ethoxy-phen-4-yl, chloro-phenyl, 1-chloro-phen-4-yl, trifluoromethoxy-phenyl, 1-trifluoromethoxy-phen-4-yl, trifluoromethyl-phenyl, 1-trifluoromethyl-phen-4-yl, trifluoromethyl-chloro-phenyl, 1-trifluoromethyl-2-chloro-phen-4-yl, trifluoromethoxy-chloro-phenyl, 1-trifluoromethoxy-2-chloro-phen-4-yl, methyl-sulfonyl-phenyl, 1-methyl-sulfonyl-phen-4-yl, methyl-thio-phenyl, methyl-thio-phen-4-yl;
and the physiologically acceptable salts, solvates, tautomers and stereoisomers thereof, including mixtures thereof in all ratios.

In a preferred embodiment, a compound according to formula (I) and above embodiments is provided, wherein:
R2 denotes methyl, ethyl, propenyl, cyclopropylmethyl, phenylmethyl, phenylethyl, phenylpropyl, trifluoromethoxy-phenylmethyl, chloro-phenylmethyl, chloro-phenylethyl, difluoro-phenylmethyl, cyano-phenylmethyl, hydroxy-phenylmethyl, pyridylmethyl, fluoro-pyridylmethyl, fluoro-phenylmethyl, fluoro-phenylethyl, dimethyl-phenylmethyl, methyl-phenylmethyl, benzo[1,3]dioxole-methyl, methoxy-phenylmethyl, chloro-thiophenylmethyl, ethyl-phenylmethyl, dichloro-phenylmethyl, chloro-phenylethyl, chloro-phenylpropyl, difluoro-phenylethyl, methyl-pyrrolylmethyl, methyl-furanylmethyl, quinolinylmethyl, isoquinolinylmethyl, bromo-thiazolylmethyl, methyl-pyrazolylmethyl, difluoro-phenylpropyl, methyl-thiazolylmethyl, methyl-isooxazolylmethyl, [1,2,4]-oxadiazolylmethyl, methyl-imidazolylmethyl, imidazo-pyridylmethyl, fluoro-phenylmethyl, trifluoromethyl-phenylmethyl, nitro-phenylmethyl, phenylmethyloxy-phenylmethyl, naphthylmethyl, isobutyl-phenylmethyl, isopropyl-phenylmethyl, trifluoro-phenylmethyl, dichloro-phenyl-carbonyl, fluoro-phenyl-carbonyl, difluoro-phenyl-trifluoroethyl, fluoro-phenyl-trifluoroethyl, tert.-butyl-carbamate, difluoro-phenyl-methyl-amino, phenyl-methyl-amino, acetamide, trifluoro-acetamide, benzamide, phenylamino, methane-sulfonamide, benzene-sulfonamide, trifluoromethyl-benzene-sulfonamide, phenyl-urea, methyl-urea;
and the physiologically acceptable salts, solvates, tautomers and stereoisomers thereof, including mixtures thereof in all ratios.

In a preferred embodiment, a compound according to formula (I) and above embodiments is provided, wherein:
R3 if W is N or CH, denotes H;
and the physiologically acceptable salts, solvates, tautomers and stereoisomers thereof, including mixtures thereof in all ratios.

In another aspect, the object of the present invention has surprisingly been solved by providing a compound selected from the group consisting of:

| Compound No. | Chemical Structure |
|---|---|
| 1 | 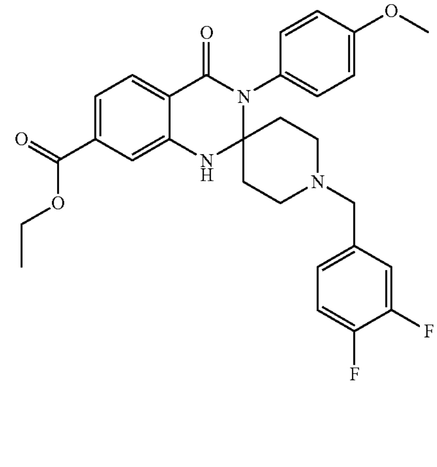 [SMILES: CCOC(=O)c1ccc2c(c1)NC1(CCN(Cc3ccc(F)c(F)c3)CC1)N(c1ccc(OC)cc1)C2=O] |

-continued
| Compound No. | Chemical Structure |
|---|---|
| 2 | 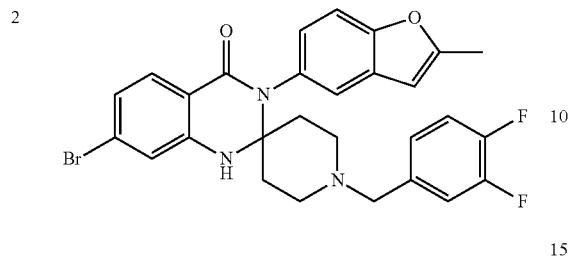 |
| 3 | 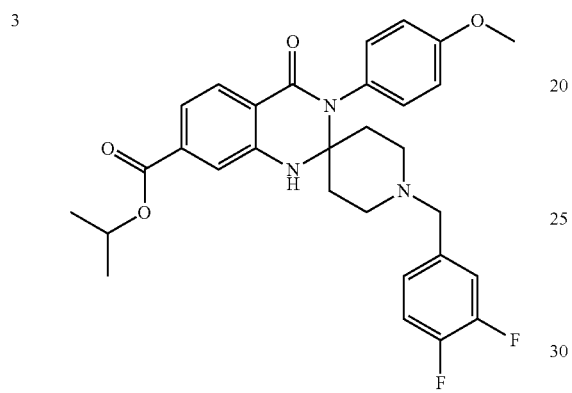 |
| 4 | 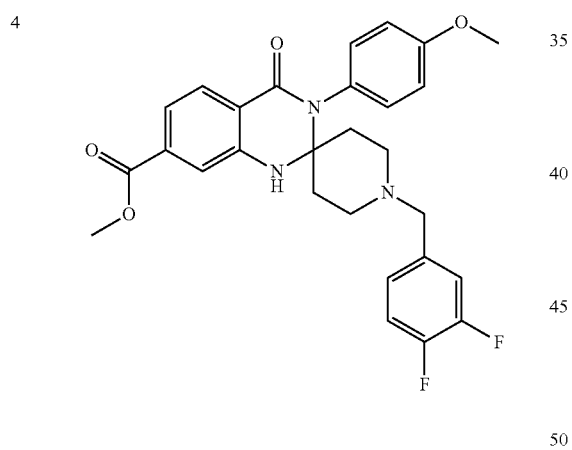 |
| 5 | 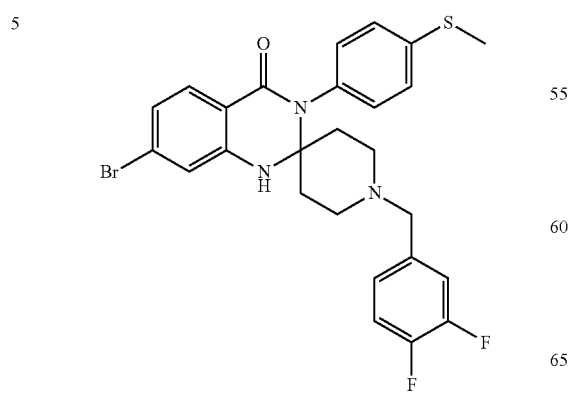 |
-continued
| Compound No. | Chemical Structure |
|---|---|
| 6 | 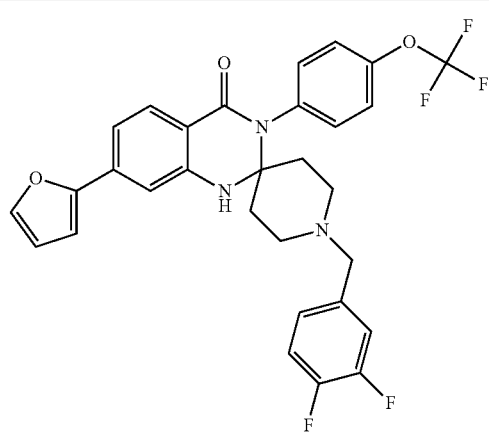 [SMILES: O=C1c2ccc(-c3ccco3)cc2NC2(CCN(Cc3ccc(F)c(F)c3)CC2)N1c1ccc(OC(F)(F)F)cc1] |
| 7 | 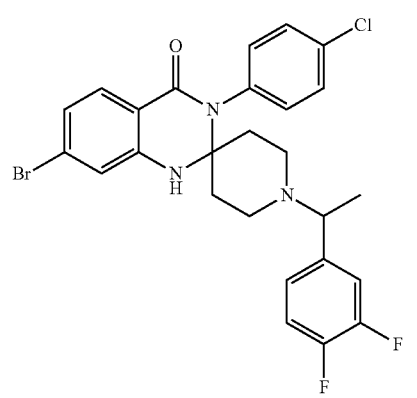 [SMILES: CC(c1ccc(F)c(F)c1)N1CCC2(CC1)Nc1cc(Br)ccc1C(=O)N2c1ccc(Cl)cc1] |
| 8 | 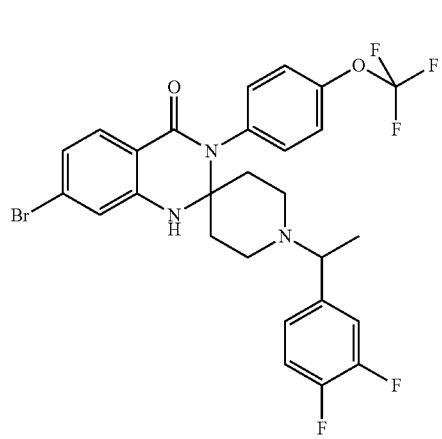 [SMILES: CC(c1ccc(F)c(F)c1)N1CCC2(CC1)Nc1cc(Br)ccc1C(=O)N2c1ccc(OC(F)(F)F)cc1] |
| 9 | 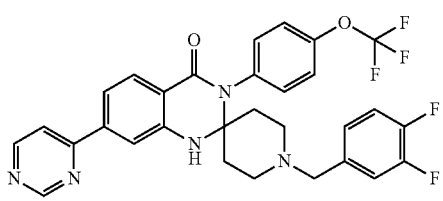 [SMILES: O=C1c2ccc(-c3ccncn3)cc2NC2(CCN(Cc3ccc(F)c(F)c3)CC2)N1c1ccc(OC(F)(F)F)cc1] |

| Compound No. | Chemical Structure |
|---|---|
| 10 | 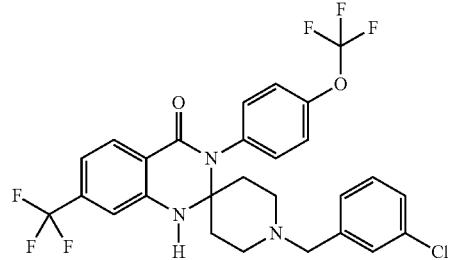 [SMILES: O=C1c2ccc(C(F)(F)F)cc2NC2(CCN(Cc3cccc(Cl)c3)CC2)N1c1ccc(OC(F)(F)F)cc1] |
| 11 | 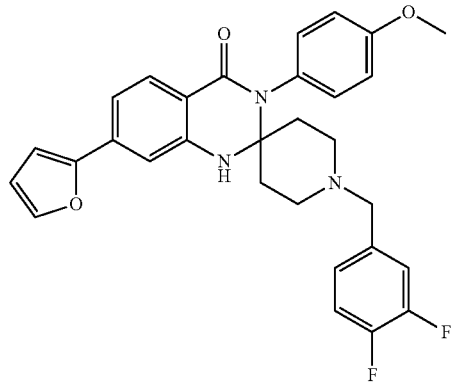 |
| 12 | 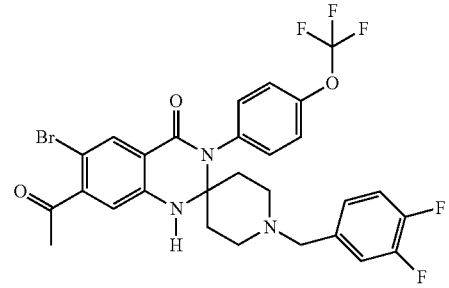 [SMILES: CC(=O)c1cc2c(cc1Br)C(=O)N(c1ccc(OC(F)(F)F)cc1)C1(CCN(Cc3ccc(F)c(F)c3)CC1)N2] |
| 13 | 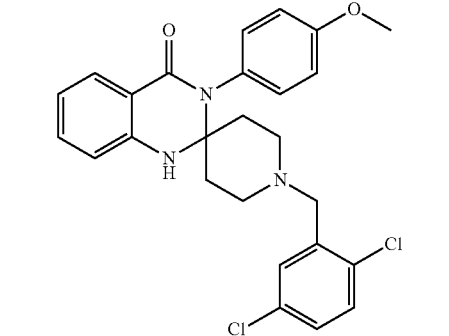 [SMILES: COc1ccc(N2C(=O)c3ccccc3NC23CCN(Cc2cc(Cl)ccc2Cl)CC3)cc1] |
| Compound No. | Chemical Structure |
|---|---|
| 14 | 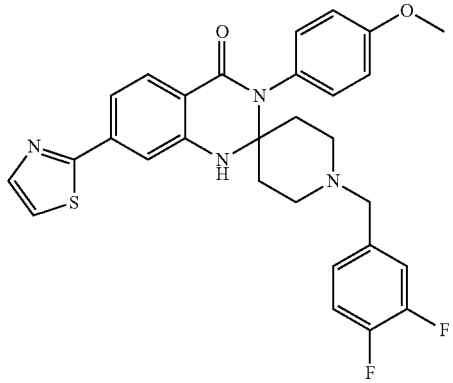 |
| 15 | 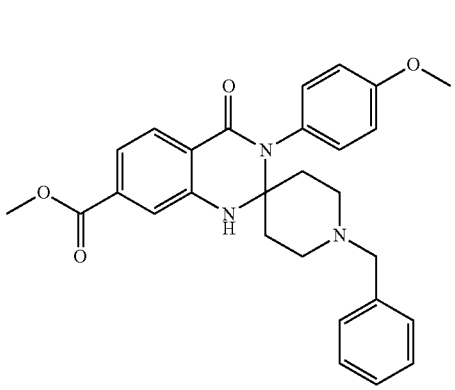 |
| 16 | 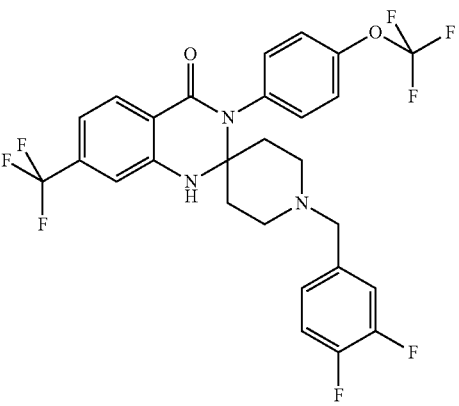 [SMILES: O=C1c2ccc(C(F)(F)F)cc2NC2(CCN(Cc3ccc(F)c(F)c3)CC2)N1c1ccc(OC(F)(F)F)cc1] |
| 17 | 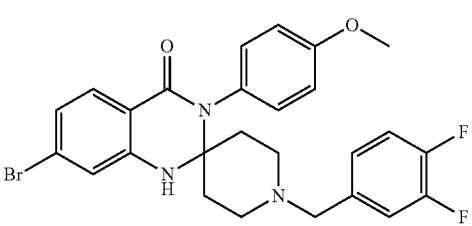 [SMILES: COc1ccc(N2C(=O)c3ccc(Br)cc3NC23CCN(Cc2ccc(F)c(F)c2)CC3)cc1] |

-continued
| Compound No. | Chemical Structure |
|---|---|
| 18 | 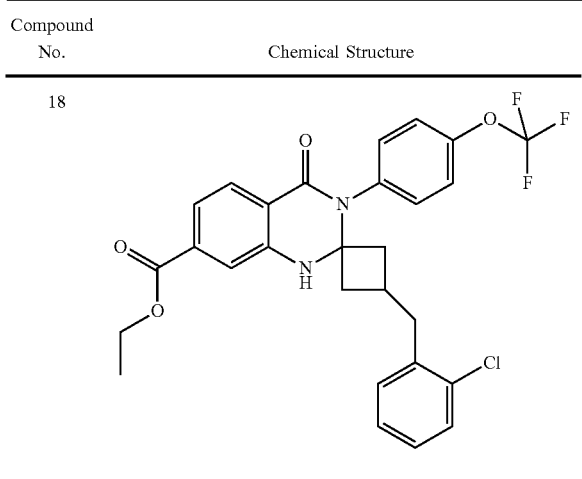 |
| 19 | 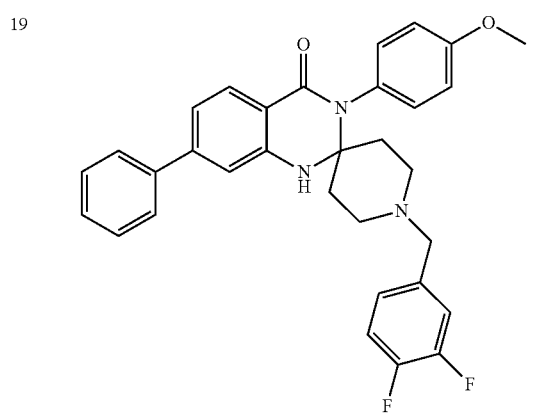 |
| 20 | 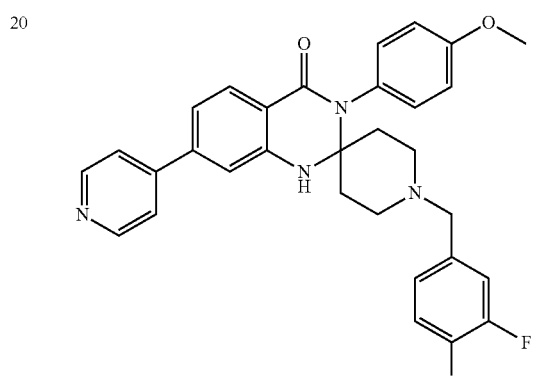 |
| 21 | 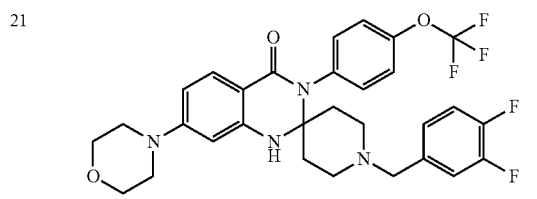 |
| 22 | 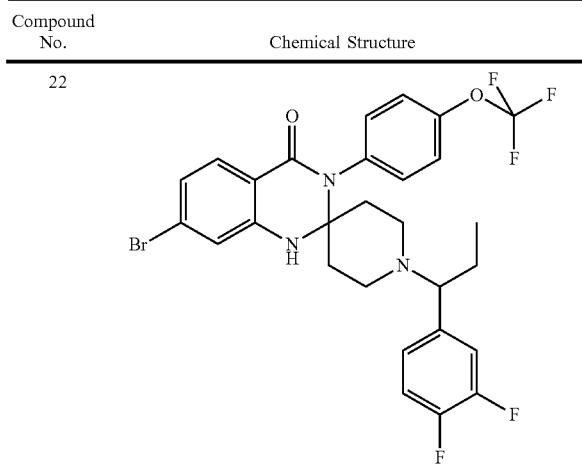 |
| 23 | 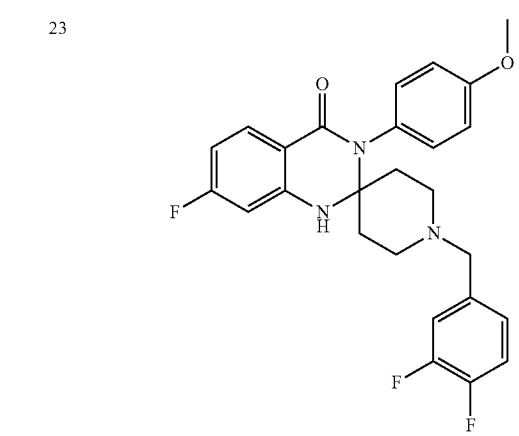 |
| 24 | 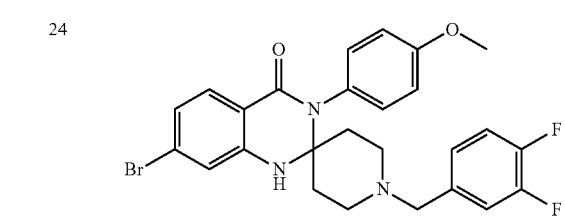 |
| 25 | 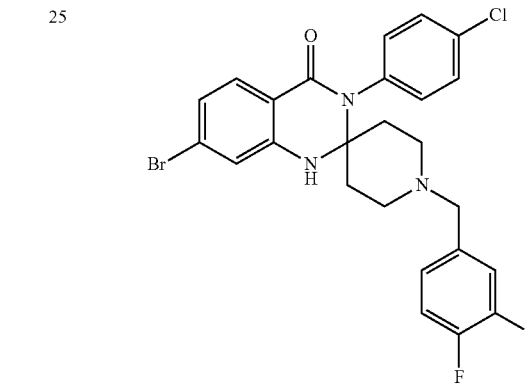 |

-continued
| Compound No. | Chemical Structure |
|---|---|
| 26 | 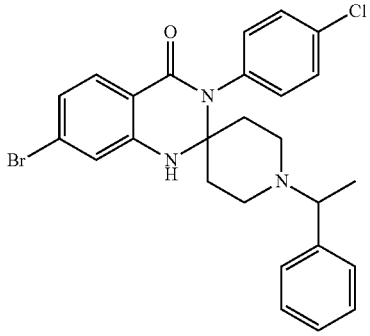 [SMILES: CC(c1ccccc1)N1CCC2(CC1)Nc1cc(Br)ccc1C(=O)N2c1ccc(Cl)cc1] |
| 27 | 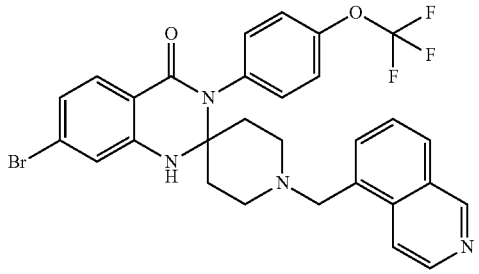 [SMILES: O=C1c2ccc(Br)cc2NC2(CCN(Cc3cccc4cnccc34)CC2)N1c1ccc(OC(F)(F)F)cc1] |
| 28 | 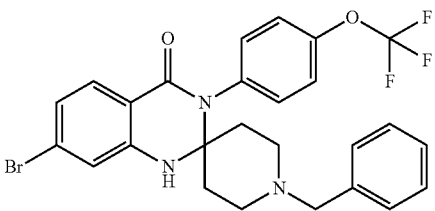 |
| 29 | 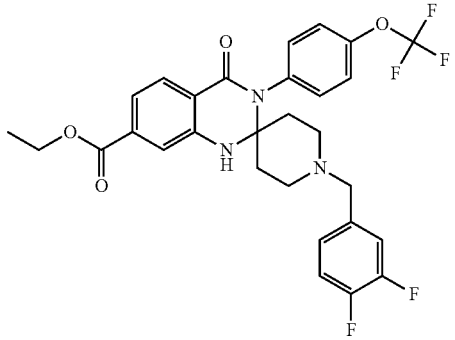 [SMILES: CCOC(=O)c1ccc2c(c1)NC1(CCN(Cc3ccc(F)c(F)c3)CC1)N(c1ccc(OC(F)(F)F)cc1)C2=O] |
| 30 | 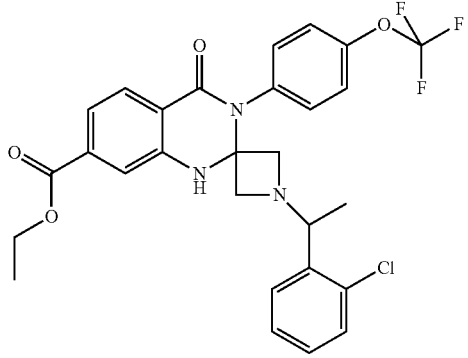 [SMILES: CCOC(=O)c1ccc2c(c1)NC1(CN(C(C)c3ccccc3Cl)C1)N(c1ccc(OC(F)(F)F)cc1)C2=O] |
-continued
| Compound No. | Chemical Structure |
|---|---|
| 31 | 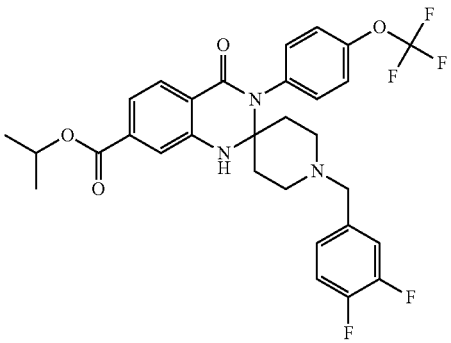 [SMILES: CC(C)OC(=O)c1ccc2c(c1)NC1(CCN(Cc3ccc(F)c(F)c3)CC1)N(c1ccc(OC(F)(F)F)cc1)C2=O] |
| 32 | 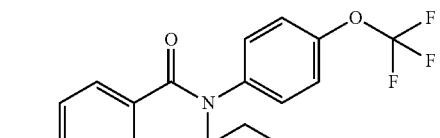 |
| 33 | 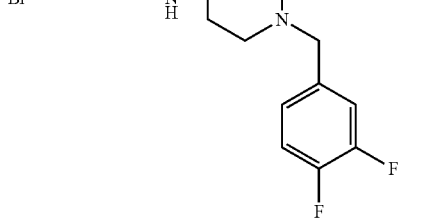 |
| 34 | 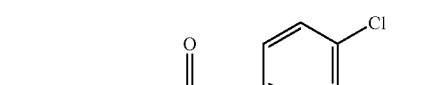 |

| Compound No. | Chemical Structure |
|---|---|
| 35 | (methyl ester-substituted quinazolinone spiro-azetidine with N-benzyl) |
| 36 | (methyl ester-substituted quinazolinone with 4-OCF3 phenyl, spiro-piperidine N-(3,4-difluorobenzyl)) |
| 37 | (7-Br quinazolinone with 4-(2-methoxyethoxy)phenyl, spiro-piperidine N-(3,4-difluorobenzyl)) |
| 38 | (7-Cl quinazolinone with 4-methoxyphenyl, spiro-piperidine N-(3-chlorobenzyl)) |
| 39 | (7-methoxy quinazolinone with 4-methoxyphenyl, spiro-piperidine N-(3,4-difluorobenzyl)) |
| 40 | (7-(pyridin-3-yl) quinazolinone with 4-methoxyphenyl, spiro-piperidine N-(3,4-difluorobenzyl)) |
| 41 | (7-(furan-2-yl) quinazolinone with 4-(methylthio)phenyl, spiro-piperidine N-(3,4-difluorobenzyl)) |
| 42 | (7-CF3 quinazolinone with 4-OCF3 phenyl, spiro-piperidine N-(3-cyanobenzyl)) |
| 43 | (7-Br quinazolinone with 4-OCF3 phenyl, spiro-piperidine N-(2,2,2-trifluoro-1-(3-fluorophenyl)ethyl)) |

| Compound No. | Chemical Structure |
|---|---|
| 44 | 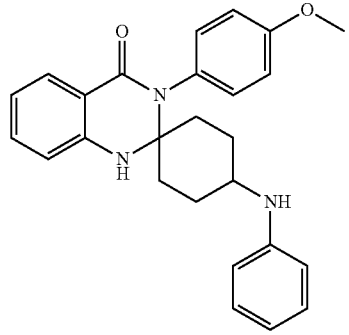 [SMILES: COc1ccc(N2C(=O)c3ccccc3NC23CCC(Nc2ccccc2)CC3)cc1] |
| 45 | 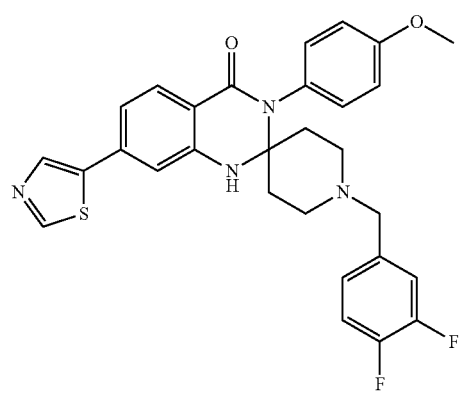 [SMILES: COc1ccc(N2C(=O)c3ccc(-c4cncs4)cc3NC23CCN(Cc2ccc(F)c(F)c2)CC3)cc1] |
| 46 | 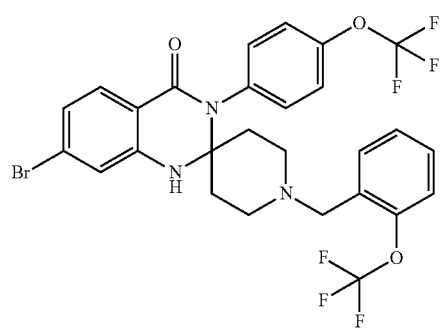 [SMILES: O=C1c2ccc(Br)cc2NC2(CCN(Cc3ccccc3OC(F)(F)F)CC2)N1c1ccc(OC(F)(F)F)cc1] |
| 47 | 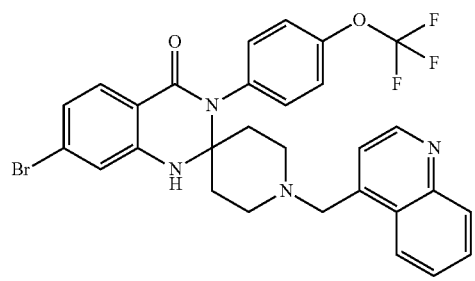 [SMILES: O=C1c2ccc(Br)cc2NC2(CCN(Cc3ccnc4ccccc34)CC2)N1c1ccc(OC(F)(F)F)cc1] |
| Compound No. | Chemical Structure |
|---|---|
| 48 | 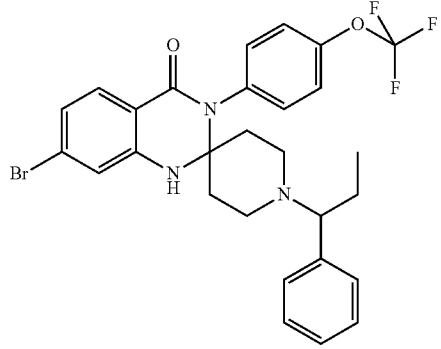 [SMILES: CCC(c1ccccc1)N1CCC2(CC1)Nc1cc(Br)ccc1C(=O)N2c1ccc(OC(F)(F)F)cc1] |
| 49 | 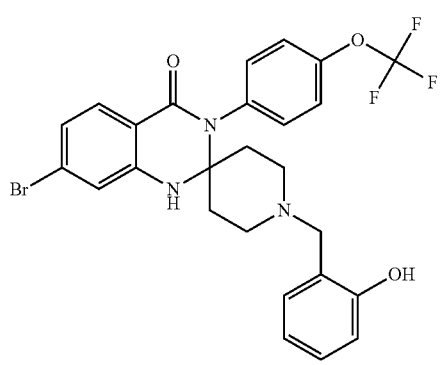 [SMILES: O=C1c2ccc(Br)cc2NC2(CCN(Cc3ccccc3O)CC2)N1c1ccc(OC(F)(F)F)cc1] |
| 50 | 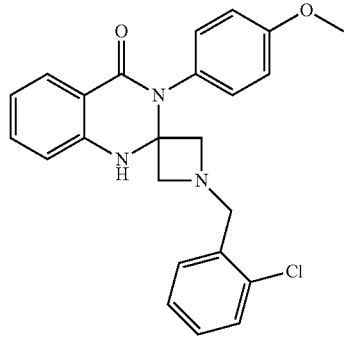 [SMILES: COc1ccc(N2C(=O)c3ccccc3NC23CN(Cc2ccccc2Cl)C3)cc1] |
| 51 | 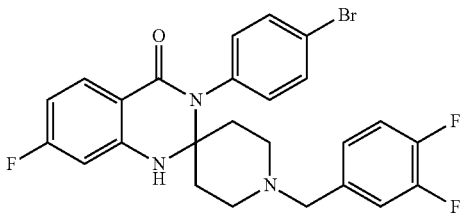 [SMILES: O=C1c2ccc(F)cc2NC2(CCN(Cc3ccc(F)c(F)c3)CC2)N1c1ccc(Br)cc1] |

TABLE-continued
| Compound No. | Chemical Structure |
|---|---|
| 52 | 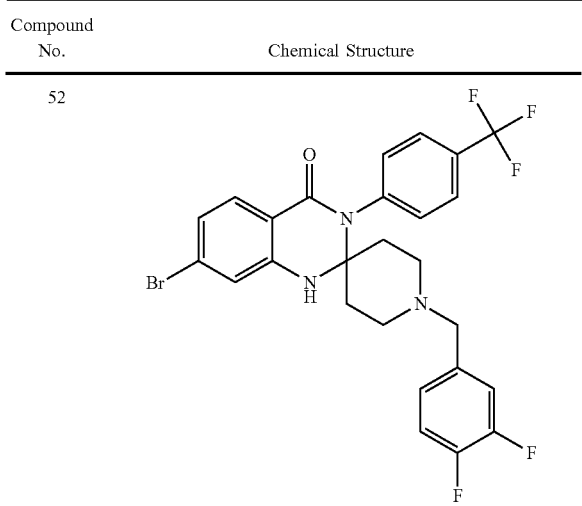 |
| 53 | 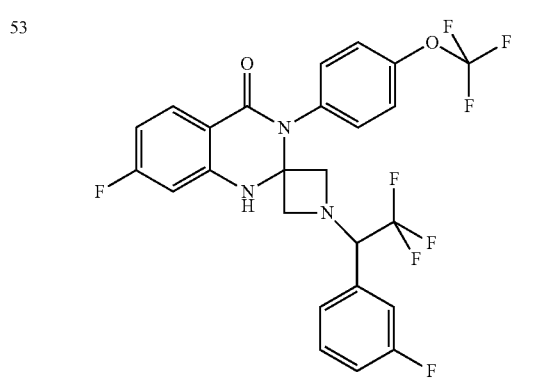 |
| 54 | 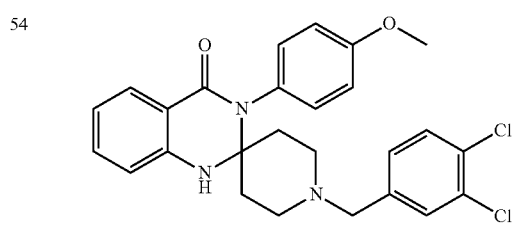 |
| 55 | 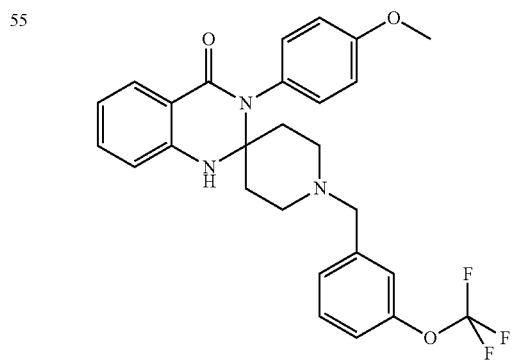 |
| Compound No. | Chemical Structure |
|---|---|
| 56 | 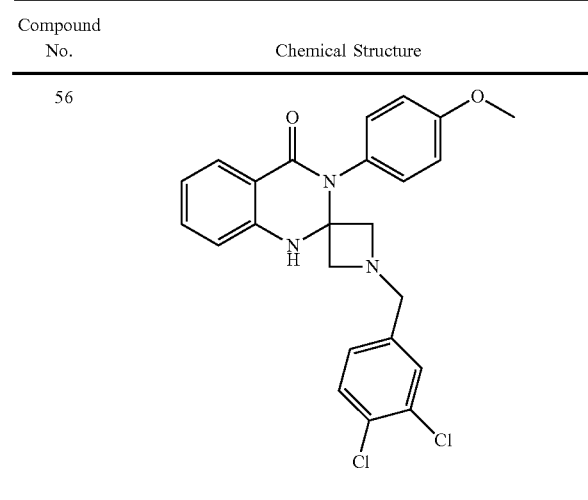 |
| 57 | 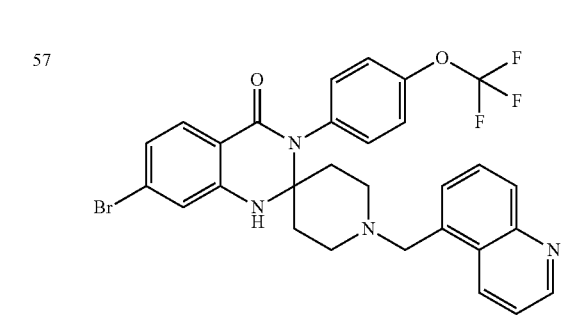 |
| 58 | 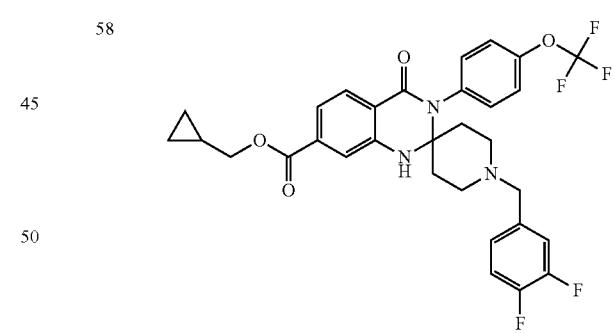 |
| 59 | 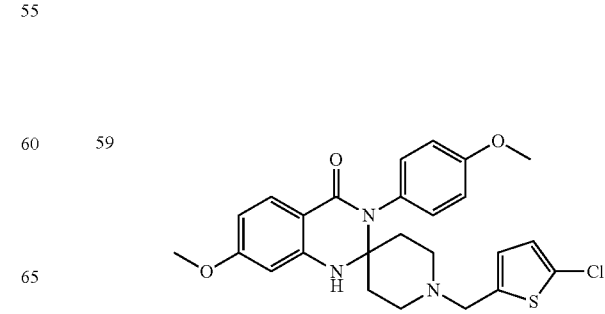 |

-continued

| Compound No. | Chemical Structure |
|---|---|
| 60 | 7-methyl, N-(4-methoxyphenyl), spiro-piperidine N-benzyl-3,4-difluoro |
| 61 | 7-bromo, N-(4-chlorophenyl), spiro-piperidine N-(1-phenylpropyl) |
| 62 | 7-chloro, N-(4-methoxyphenyl), spiro-piperidine N-(2-chlorobenzyl) |
| 63 | 7-ethyl, N-(4-methoxyphenyl), spiro-piperidine N-benzyl-3,4-difluoro |

| Compound No. | Chemical Structure |
|---|---|
| 64 | 7-fluoro, N-(4-chlorophenyl), spiro-piperidine N-benzyl-3,4-difluoro |
| 65 | N-(4-methoxyphenyl), spiro-azetidine N-(2-trifluoromethoxybenzyl) |
| 66 | N-(4-methoxyphenyl), spiro-piperidine N-(2-trifluoromethylbenzyl) |
| 67 | N-(4-methoxyphenyl), spiro-piperidine N-(2-trifluoromethoxybenzyl) |

-continued

| Compound No. | Chemical Structure |
|---|---|
| 68 | 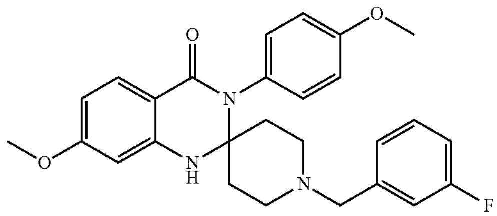 [SMILES: COc1ccc(N2C(=O)c3ccc(OC)cc3NC23CCN(Cc2cccc(F)c2)CC3)cc1] |
| 69 | 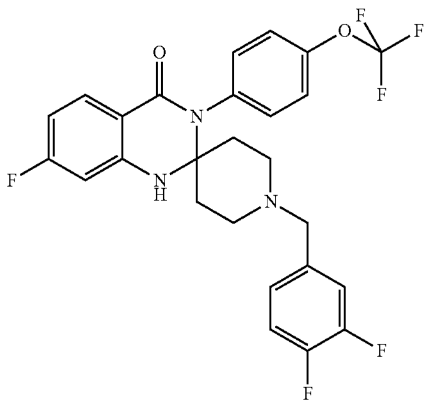 [SMILES: O=C1c2ccc(F)cc2NC2(CCN(Cc3ccc(F)c(F)c3)CC2)N1c1ccc(OC(F)(F)F)cc1] |
| 70 | 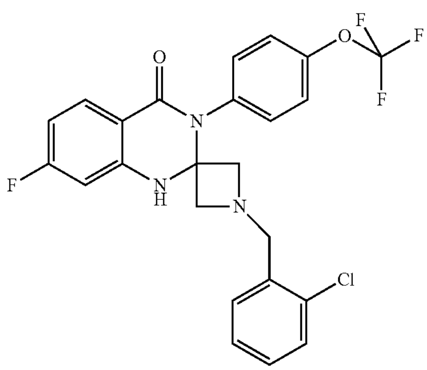 [SMILES: O=C1c2ccc(F)cc2NC2(CN(Cc3ccccc3Cl)C2)N1c1ccc(OC(F)(F)F)cc1] |
| 71 | 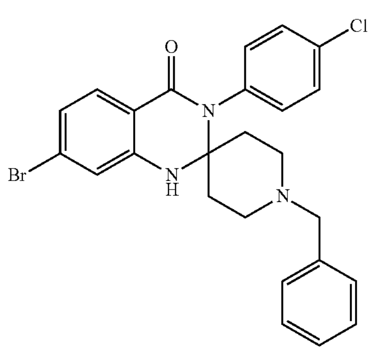 [SMILES: O=C1c2ccc(Br)cc2NC2(CCN(Cc3ccccc3)CC2)N1c1ccc(Cl)cc1] |

-continued

| Compound No. | Chemical Structure |
|---|---|
| 72 | 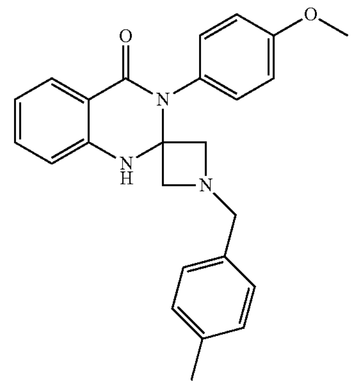 [SMILES: COc1ccc(N2C(=O)c3ccccc3NC23CN(Cc2ccc(C)cc2)C3)cc1] |
| 73 | 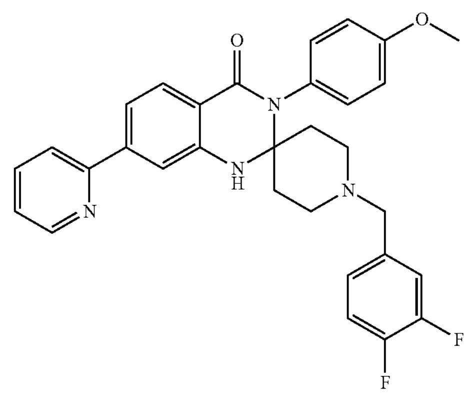 [SMILES: COc1ccc(N2C(=O)c3ccc(-c4ccccn4)cc3NC23CCN(Cc2ccc(F)c(F)c2)CC3)cc1] |
| 74 | 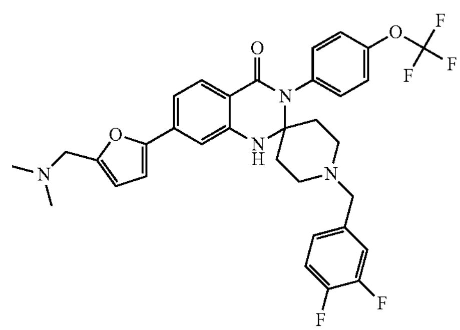 [SMILES: CN(C)Cc1ccc(-c2ccc3c(c2)NC2(CCN(Cc4ccc(F)c(F)c4)CC2)N(c2ccc(OC(F)(F)F)cc2)C3=O)o1] |
| 75 | 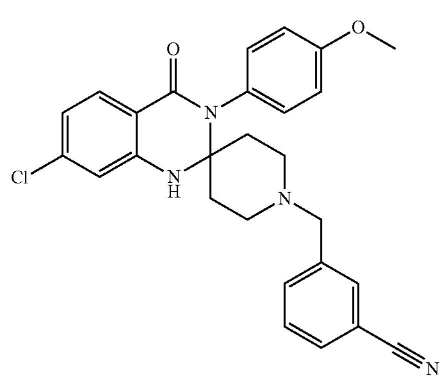 [SMILES: COc1ccc(N2C(=O)c3ccc(Cl)cc3NC23CCN(Cc2cccc(C#N)c2)CC3)cc1] |

-continued
| Compound No. | Chemical Structure |
|---|---|
| 76 | 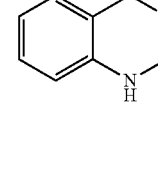 |
| 77 | 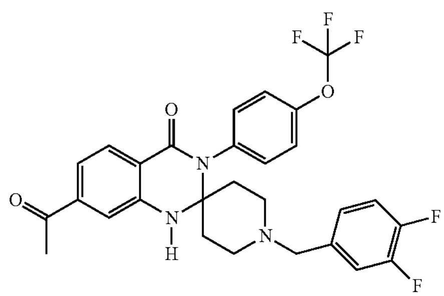 [SMILES: CC(=O)c1ccc2c(c1)NC1(CCN(Cc3ccc(F)c(F)c3)CC1)N(c1ccc(OC(F)(F)F)cc1)C2=O] |
| 78 | 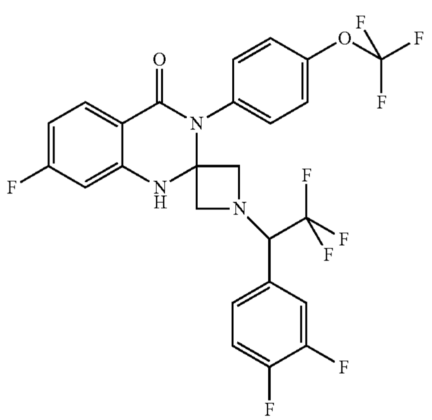 [SMILES: O=C1c2ccc(F)cc2NC2(CN(C(c3ccc(F)c(F)c3)C(F)(F)F)C2)N1c1ccc(OC(F)(F)F)cc1] |
| 79 | 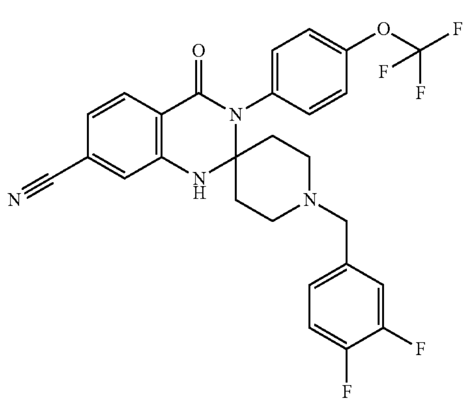 [SMILES: N#Cc1ccc2c(c1)NC1(CCN(Cc3ccc(F)c(F)c3)CC1)N(c1ccc(OC(F)(F)F)cc1)C2=O] |
-continued
| Compound No. | Chemical Structure |
|---|---|
| 80 | 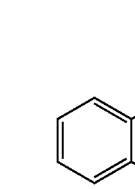 |
| 81 | 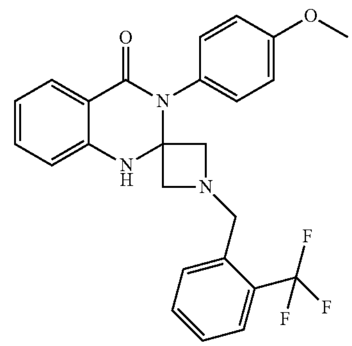 [SMILES: COc1ccc(N2C(=O)c3ccccc3NC23CN(Cc2ccccc2C(F)(F)F)C3)cc1] |
| 82 | 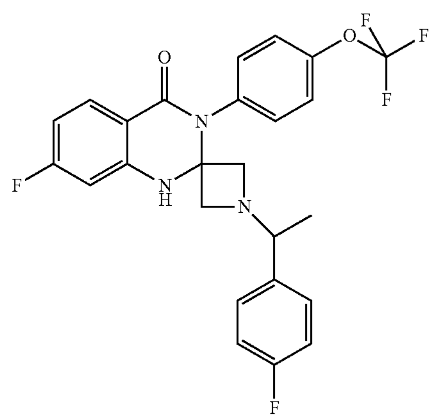 [SMILES: CC(c1ccc(F)cc1)N1CC2(C1)Nc1cc(F)ccc1C(=O)N2c1ccc(OC(F)(F)F)cc1] |
| 83 | 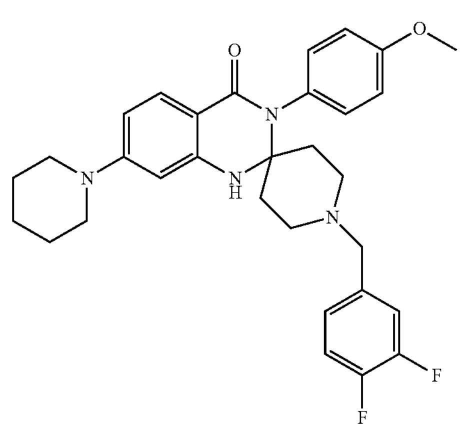 [SMILES: COc1ccc(N2C(=O)c3ccc(N4CCCCC4)cc3NC23CCN(Cc2ccc(F)c(F)c2)CC3)cc1] |

-continued
| Compound No. | Chemical Structure |
|---|---|
| 84 | 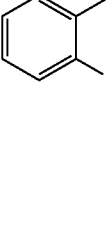 |
| 85 | 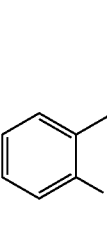 |
| 86 | 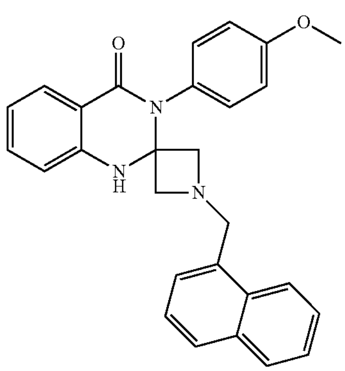 [SMILES: COc1ccc(N2C(=O)c3ccccc3NC23CN(Cc2cccc4ccccc24)C3)cc1] |
| 87 | 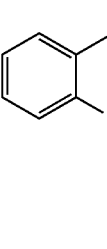 |
-continued
| Compound No. | Chemical Structure |
|---|---|
| 88 | 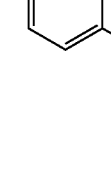 |
| 89 | 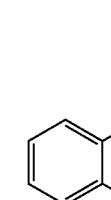 |
| 90 | 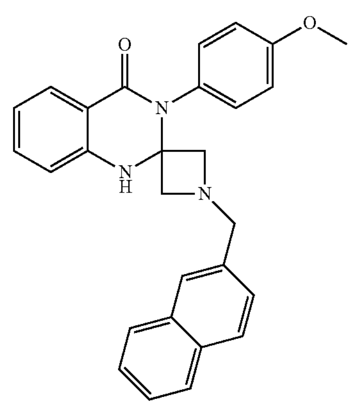 [SMILES: COc1ccc(N2C(=O)c3ccccc3NC23CN(Cc2ccc4ccccc4c2)C3)cc1] |
| 91 | 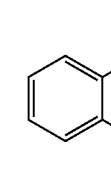 |

-continued

| Compound No. | Chemical Structure |
|---|---|
| 92 | 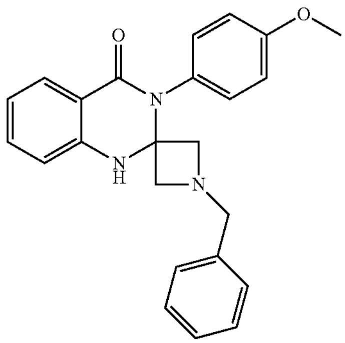 [SMILES: COc1ccc(N2C(=O)c3ccccc3NC23CN(Cc2ccccc2)C3)cc1] |
| 93 | 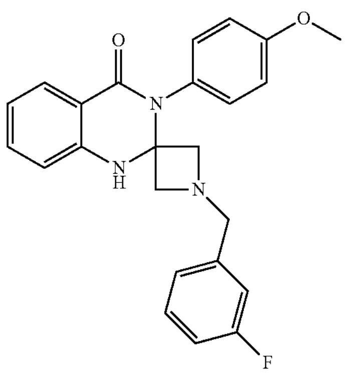 [SMILES: COc1ccc(N2C(=O)c3ccccc3NC23CN(Cc2cccc(F)c2)C3)cc1] |
| 94 | 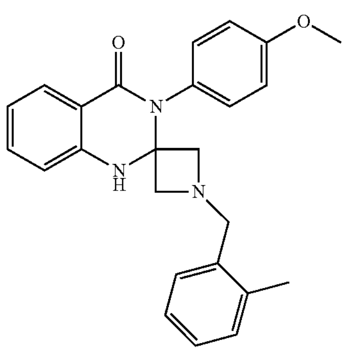 [SMILES: COc1ccc(N2C(=O)c3ccccc3NC23CN(Cc2ccccc2C)C3)cc1] |
| 95 | 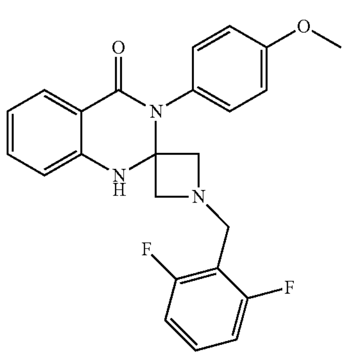 [SMILES: COc1ccc(N2C(=O)c3ccccc3NC23CN(Cc2c(F)cccc2F)C3)cc1] |

-continued

| Compound No. | Chemical Structure |
|---|---|
| 96 | 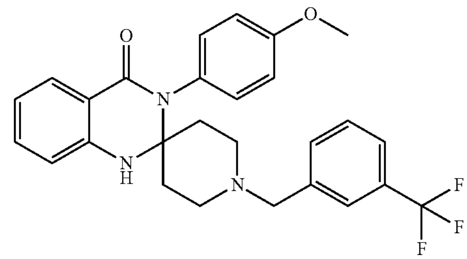 [SMILES: COc1ccc(N2C(=O)c3ccccc3NC23CCN(Cc2cccc(C(F)(F)F)c2)CC3)cc1] |
| 97 | 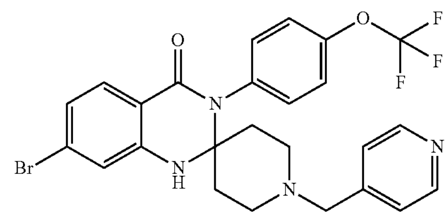 |
| 98 | 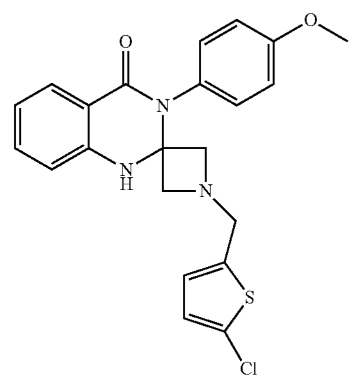 [SMILES: COc1ccc(N2C(=O)c3ccccc3NC23CN(Cc2ccc(Cl)s2)C3)cc1] |
| 99 | 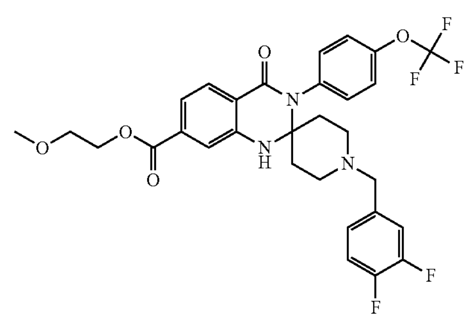 [SMILES: COCCOC(=O)c1ccc2c(c1)NC1(CCN(Cc3ccc(F)c(F)c3)CC1)N(c1ccc(OC(F)(F)F)cc1)C2=O] |
| 100 | 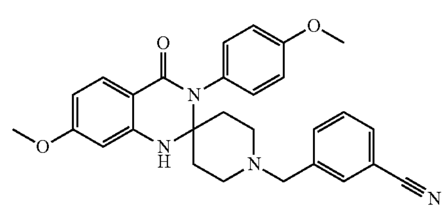 [SMILES: COc1ccc(N2C(=O)c3ccc(OC)cc3NC23CCN(Cc2cccc(C#N)c2)CC3)cc1] |

| Compound No. | Chemical Structure |
|---|---|
| 101 | 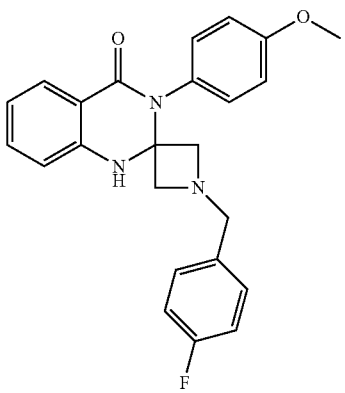 |
| 102 | 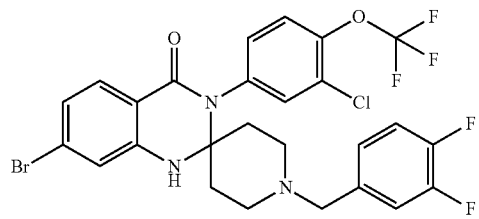 [SMILES: O=C1c2ccc(Br)cc2NC2(CCN(Cc3ccc(F)c(F)c3)CC2)N1c1ccc(OC(F)(F)F)c(Cl)c1] |
| 103 | 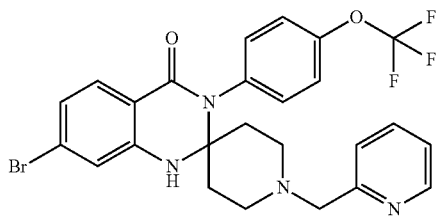 [SMILES: O=C1c2ccc(Br)cc2NC2(CCN(Cc3ccccn3)CC2)N1c1ccc(OC(F)(F)F)cc1] |
| 104 | 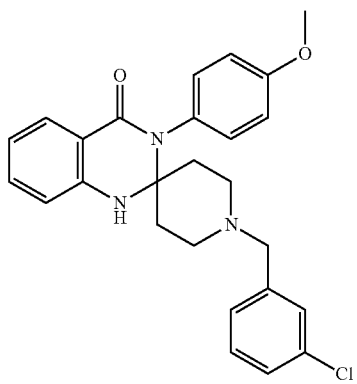 [SMILES: COc1ccc(N2C(=O)c3ccccc3NC23CCN(Cc2cccc(Cl)c2)CC3)cc1] |
| 105 | 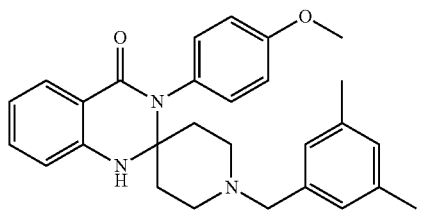 [SMILES: COc1ccc(N2C(=O)c3ccccc3NC23CCN(Cc2cc(C)cc(C)c2)CC3)cc1] |
| Compound No. | Chemical Structure |
|---|---|
| 106 | 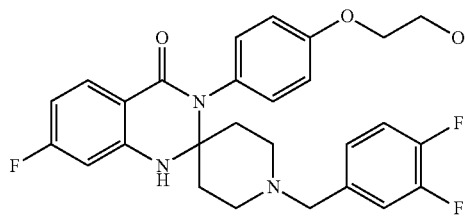 |
| 107 | 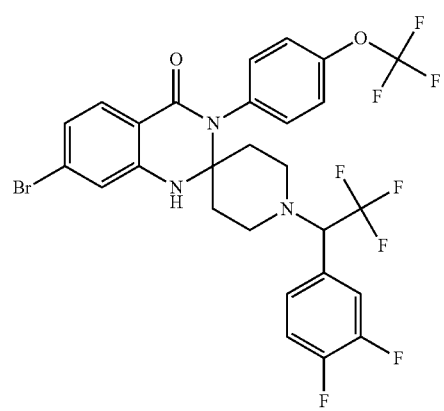 [SMILES: O=C1c2ccc(Br)cc2NC2(CCN(C(c3ccc(F)c(F)c3)C(F)(F)F)CC2)N1c1ccc(OC(F)(F)F)cc1] |
| 108 | 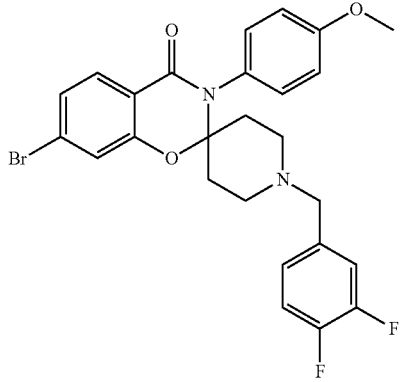 [SMILES: COc1ccc(N2C(=O)c3ccc(Br)cc3OC23CCN(Cc2ccc(F)c(F)c2)CC3)cc1] |
| 109 | |
| 110 | 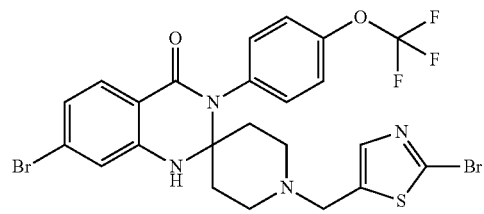 [SMILES: O=C1c2ccc(Br)cc2NC2(CCN(Cc3cnc(Br)s3)CC2)N1c1ccc(OC(F)(F)F)cc1] |

| Compound No. | Chemical Structure |
|---|---|
| 111 | 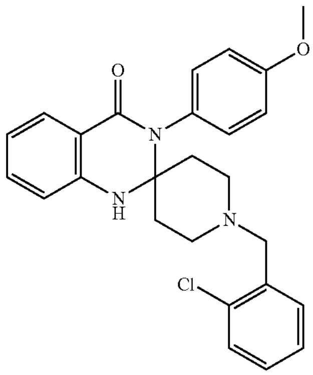 [SMILES: COc1ccc(N2C(=O)c3ccccc3NC23CCN(Cc2ccccc2Cl)CC3)cc1] |
| 112 | 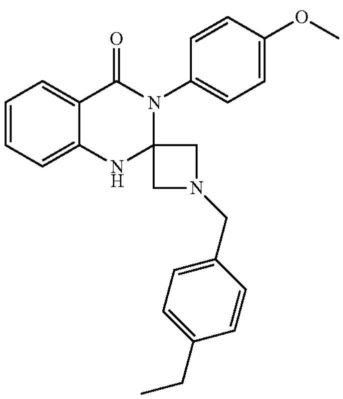 [SMILES: CCc1ccc(CN2CC3(C2)Nc2ccccc2C(=O)N3c2ccc(OC)cc2)cc1] |
| 113 | 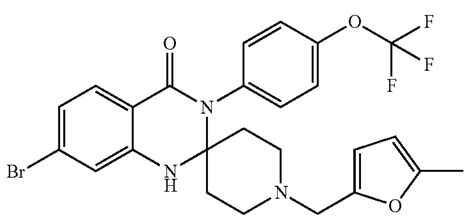 [SMILES: Cc1ccc(CN2CCC3(CC2)Nc2cc(Br)ccc2C(=O)N3c2ccc(OC(F)(F)F)cc2)o1] |
| 114 | 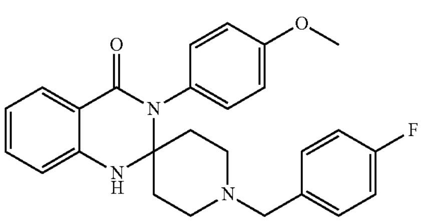 [SMILES: COc1ccc(N2C(=O)c3ccccc3NC23CCN(Cc2ccc(F)cc2)CC3)cc1] |
| 115 | 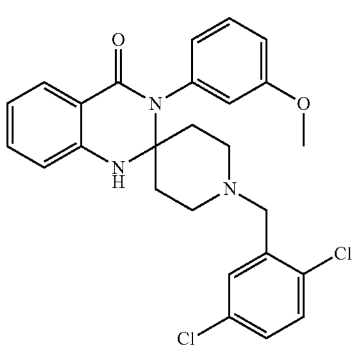 [SMILES: COc1cccc(N2C(=O)c3ccccc3NC23CCN(Cc2cc(Cl)ccc2Cl)CC3)c1] |
| 116 | |
| 117 | |
| 118 | |
| 119 | |
| 120 | |

-continued

| Compound No. | Chemical Structure |
|---|---|
| 121 | 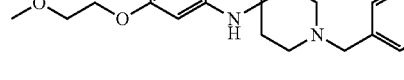 |
| 122 | 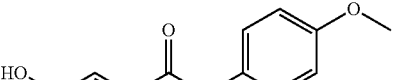 |
| 123 | 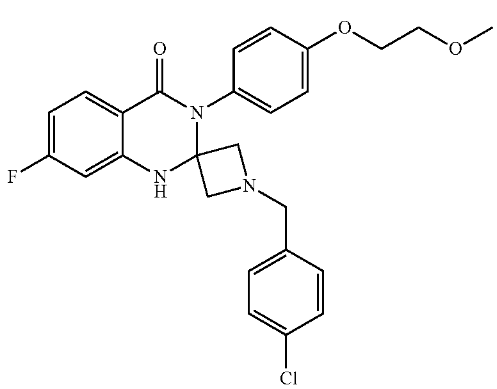 [SMILES: COCCOc1ccc(N2C(=O)c3ccc(F)cc3NC23CN(Cc2ccc(Cl)cc2)C3)cc1] |
| 124 | 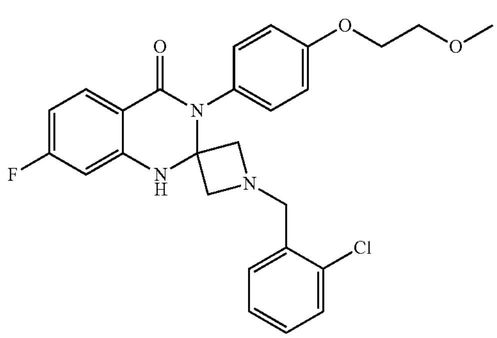 [SMILES: COCCOc1ccc(N2C(=O)c3ccc(F)cc3NC23CN(Cc2ccccc2Cl)C3)cc1] |
| 125 | 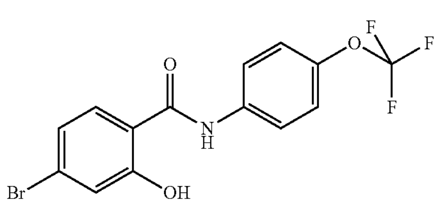 [SMILES: O=C(Nc1ccc(OC(F)(F)F)cc1)c1ccc(Br)cc1O] |

-continued

| Compound No. | Chemical Structure |
|---|---|
| 126 | 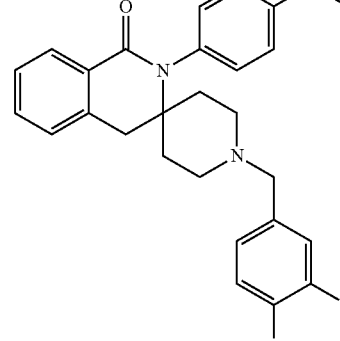 |
| 127 | 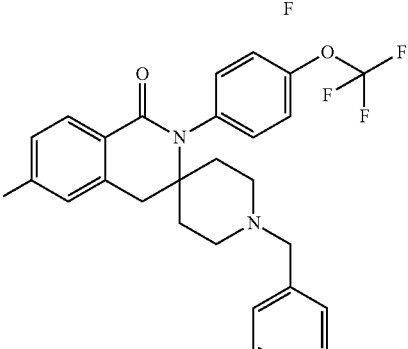 | and the physiologically acceptable salts, solvates, tautomers and stereoisomers thereof, including mixtures thereof in all ratios.

For the avoidance of doubt, if chemical name and chemical structure of the above illustrated compounds do not correspond by mistake, the chemical structure is regarded to unambigously define the compound.

All the above generically or explicitly disclosed compounds, including preferred subsets/embodiments of the herein disclosed formula (I) and Compounds 1 to 127, are hereinafter referred to as compounds of the (present) invention.

The nomenclature as used herein for defining compounds, especially the compounds according to the invention, is in general based on the rules of the IUPAC organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 10 carbon atoms, i.e. $C_1$-$C_{10}$-alkanyls, $C_2$-$C_{10}$-alkenyls and $C_2$-$C_{10}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—$CH_2CH=CH_2$; —$CH=CH-CH_3$, —$C(=CH_2)$—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—$CH_2$—C≡CH, —C≡C—$CH_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" or "heterocycle" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyyl radical. The bonding to the compounds of the general formula can be effected via any possible ring member of the heterocyyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl.

The term "aryl" for the purposes of this invention refers to a mono- or polycyclic aromatic hydrocarbon systems having 3 to 14, preferably 5 to 14, more preferably 5 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula can be effected via any possible ring member of the heteroaryl radical. Examples of suitable "heteroaryl" are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)—" group, wherein alkyl is as defined herein.

The term "alkoxyalkyl" for the purposes of this invention refers to a "alkyl-O-alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:

(i) Wermuth C G et al., Chapter 31: 671-696, The Practice of Medicinal Chemistry, Academic Press 1996;

(ii) Bundgaard H, Design of Prodrugs, Elsevier 1985; and (iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

There is furthermore intended that a compound of the invention includes isotope-labelled forms thereof. An isotope-labelled form of a compound of the invention is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the invention by well-known methods include isotopes of hydrogen, carbon, nitrogen, oxygen, phos-phorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the invention, a prodrug, thereof or a pharmaceutically acceptable salt of either which contains one or more of the above-mentioned isotopes and/or other isotopes of other atoms is intended to be part of the present invention. An isotope-labelled compound of the invention can be used in a number of beneficial ways. For example, an isotope-labelled compound of the invention into which, for example, a radioisotope, such as $^3$H or $^{14}$C, has been incorporated is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the invention has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the invention can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2$H) can also be incorporated into a compound of the invention for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the invention that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the invention with improved stability through resistance to such oxidative metabolism. Significant improvements in the pharmacokinetic profiles of compounds of the invention are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the invention which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective modulation, preferably positive allosteric modulation (agonistic activity) of metabotrobic glutamate receptor subtype-4 (mGluR4).

Due to their surprisingly strong and/or selective receptor modulation, the compounds of the invention can be advantageously administered at lower doses compared to other less potent or selective modulators of the prior art while still achieving equivalent or even superior desired biological effects. In addition, such a dose reduction may advantageously lead to less or even no medicinal adverse effects. Further, the high modulation selectivity of the compounds of the invention may translate into a decrease of undesired side effects on its own regardless of the dose applied.

The compounds of the invention being mGluR4 positive allosteric modulators generally have an half maximal effective concentration ($EC_{50}$) of less than about 100 μM, preferably less than about 10 μM, and most preferably less than about 1 μM.

The object of the present invention has surprisingly been solved in another aspect by providing the use of a compound of the invention for modulating metabotropic glutamate receptor subtype 4 (mGluR4) and/or altering glutamate level or glutamatergic signalling.

The terms "modulating, altering, modulation and/or alteration" are intended to refer for the purposes of the present invention to as follows: "partial or complete activating, stimulating, activation and/or stimulation". In this case, it is within the specialist knowledge of the average person skilled in the art to measure and determine such activating, stimulating, activation and/or stimulation by means of the usual methods of measurement and determination. Thus, a partial activating, stimulating, activation and/or stimulation, for example, can be measured and determined in relation to a complete activating, stimulating, activation and/or stimulation.

The object of the present invention has surprisingly been solved in another aspect by providing a process for manufacturing a compound of the invention, comprising the steps of:

(a) reacting a compound of formula (II)

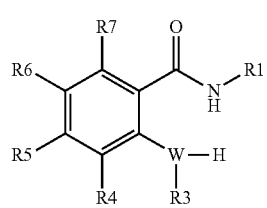

(II)

wherein

W, R1, R3, R4, R5, R6, R7 are as defined herein supra, with a compound of formula (III)

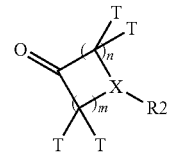

(III)

wherein

X, R2, T, n, m are as defined herein supra, to yield the compound of formula (I)

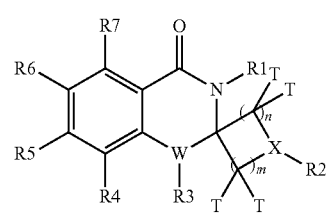

(I)

wherein

W, X, R1, R2, R3, R4, R5, R6, R7, T, n, m are as defined herein supra, or (b) reacting a compound of formula (IV)

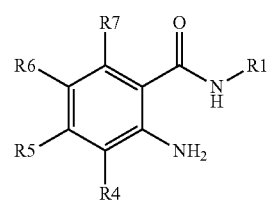

(IV)

wherein

R1, R4, R5, R6, R7 are as defined herein supra, with a compound of formula (III)

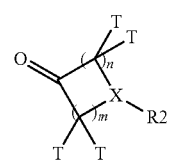

(III)

wherein

X, R2, T, n, m are as defined herein supra, to yield the compound of formula (I)

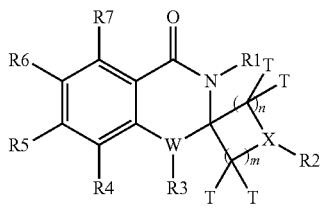

wherein
X, R1, R2, R4, R5, R6, R7, T, n, m are as defined herein supra and W is N and R3 is H;
or
(c) reacting a compound of formula (V)

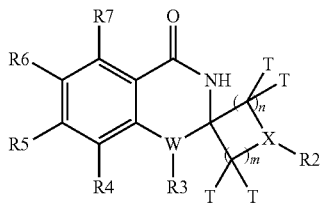

wherein
W, X, R2, R3, R4, R5, R6, R7, T, n, m are as defined herein supra,
with a compound of formula (VI)

Z—R1      (VI)

wherein
Z denotes halogen, boronic acid or a ester of boronic acid and
R1 is as defined herein supra,
to yield the compound of formula (I)

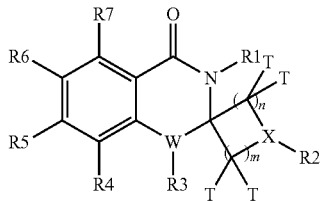

wherein
W, X, R1, R2, R3, R4, R5, R6, R7, T, n, m are as defined herein supra; and optionally
(d) converting a base or an acid of the compound of formula (I) into a salt thereof.

Some crude products were subjected to standard chromatography using solvent mixtures containing methanol, ethanol, isopropanol, ethyl acetate, n-hexane, cyclohexane, dichloromethane, n-heptane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions selected from the group consisting of: "condition which is affected or facilitated by the neuromodulatory effect of mGluR4 allosteric modulators, central nervous system disorders, addiction, tolerance or dependence, affective disorders, such as anxiety, agoraphobia, generalized anxiety disorder (GAD), obsessive-compulsive disorder (OCD), panic disorder, post-traumatic stress disorder (PTSD), social phobia, other phobias, substance-induced anxiety disorder, and acute stress disorder, mood disorders, bipolar disorders (I & II), cyclothymic disorder, depression, dysthymic disorder, major depressive disorder, and substance-induced mood disorder, psychiatric disease, such as psychotic disorders and attention-deficit/hyperactivity disorder, Parkinson's disease, and movement disorders such as bradykinesia, rigidity, dystonia, drug-induced parkinsonism, dyskinesia, tardive dyskinesia, L-DOPA-induced dyskinesia, dopamine agonist-induced dyskinesia, hyperkinetic movement disorders, Gilles de la Tourette syndrome, resting tremor, action tremor, akinesia, akinetic-rigid syndrome, akathisia, athetosis, asterixis, tics, postural instability, postencephalitic parkinsonism, muscle rigidity, chorea and choreaform movements, spasticity, myoclonus, hemiballismus, progressive supranuclear palsy, restless legs syndrome, and periodic limb movement disorder, cognitive disorders such as delirium, substance-induced persisting delirium, dementia, dementia due to HIV disease, dementia due to Huntington's disease, dementia due to Parkinson's disease, Parkinsonian-ALS demential complex, dementia of the Alzheimer's type, substance-induced persisting dementia, and mild cognitive impairment, neurological disorders such as neurodegeneration, neurotoxicity or ischemia such as stroke, spinal cord injury, cerebral hypoxia, intracranial hematoma, memory impairment, Alzheimer's disease, dementia, delirium tremens, other forms of neurodegeneration, neurotoxicity, and ischemia, inflammation and/or neurodegeneration resulting from traumatic brain injury, inflammatory central nervous system disorders, such as multiple sclerosis forms such as benign multiple sclerosis, relapsing-remitting multiple sclerosis, secondary progressive multiple sclerosis, primary progressive multiple sclerosis, and progressive-relapsing multiple sclerosis, migraine, epilepsy and tremor, temporal lobe epilepsy, epilepsy secondary to another disease or injury such as chronic encephalitis, traumatic brain injury, stroke or ischemia, medulloblastomas, inflammatory or neuropathic pain, metabolic disorders associated with glutamate dysfunction, type 2 diabetes, diseases or disorders of the retina, retinal degeneration or macular degeneration, diseases or disorders of the gastrointestinal tract including gastroesophageal reflux disease (GERD), lower esophageal sphincter diseases or disorders, diseases of gastrointestinal motility, colitis, Crohn's disease or irritable bowel syndrome (IBS), cancers." A corresponding use for the preparation of a medicament for the treatment and/or prophylaxis of the aforementioned conditions is intended to be comprised. A corresponding method of treatment administering at least one compound of the invention to a patient in need thereof is also intended to be comprised.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in the following:

levodopa, levodopa with selective extracerebral decarboxylase inhibitors, carbidopa, entacapone, COMT inhibitors, dopamine agonists, dopamine receptor agonists, apomorphine, anticholinergics, cholinergic agonists, butyrophenone neuroleptic agents, diphenylbutylpiperidine neuroleptic agents, heterocyclic dibenzazepine neuroleptic agents, indolone neuroleptic agents, phenothiazine neuroleptic agents, thioxanthene neuroleptic agents, NMDA receptor antagonists, MAO-B inhibitors, mGluR3 PAMs or agonists, mGluR4 PAMs or agonists, mGluR5 antagonist or A2A antagonists.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

NMR Spectra were acquired on a Varian $^{Unity}$Inova 400 MHz NMR spectrometer equipped with an Automation Triple Broadband (ATB) probe. The ATB probe was simultaneously tuned to $^1H$, $^{19}F$ and $^{13}C$. For typical $^1H$ NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to 1 second. Spectra were collected at 25° C. $^1H$ NMR Spectra are typically processed with 0.2 Hz line broadening and zero-filling to 131072 points prior to Fourier transformation.

Method A (Rapid LC): A Shimadzu Shim-pack XR-ODS, 3.0×30 mm, 2.2 μm, was used at a temperature of 50° C. and at a flow rate of 1.5 mL/min, 2 μL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient (II) hold for 0.8 min at 95% (B) (III) decrease from 95-15% (B) in a 0.1 min linear gradient (IV) hold from 0.29 min at 15% (B).

Method B (Polar Stop-Gap): An Agilent Zorbax Bonus RP, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold from 0.29 min at 5% (B).

Preparative HPLC was performed using a system controlled by Chromeleon software and consisting of two Varian PrepStar Model 218 Pumps, a Varian ProStar Model 320 UV/Vis detector, a SEDEX 55 ELSD detector, and a Gilson 215 liquid handler. Typical HPLC mobile phases consist of water and methanol. The standard column is a Varian Dynamax 21.4 mm diameter Microsorb Guard-8 C18 column.

The contents of all cited references are hereby incorporated by reference in their entirety. The invention is explained in more detail by means of the following examples without, however, being restricted thereto.

EXAMPLES

I. Synthesis of Selected Compounds of the Invention

The following compounds were synthesized and characterized. However, it lies in the knowledge of a person skilled in the art to prepare and characterize these compounds differently.

General Synthesis Scheme 1

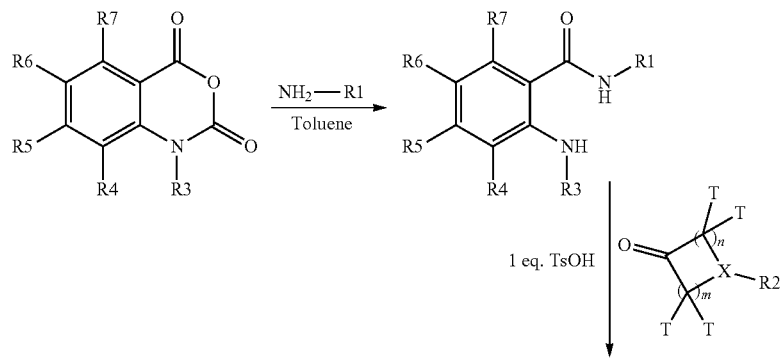

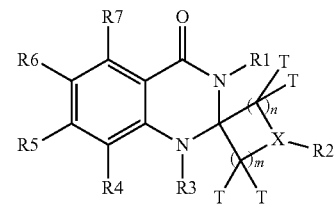

General Synthesis Scheme 2

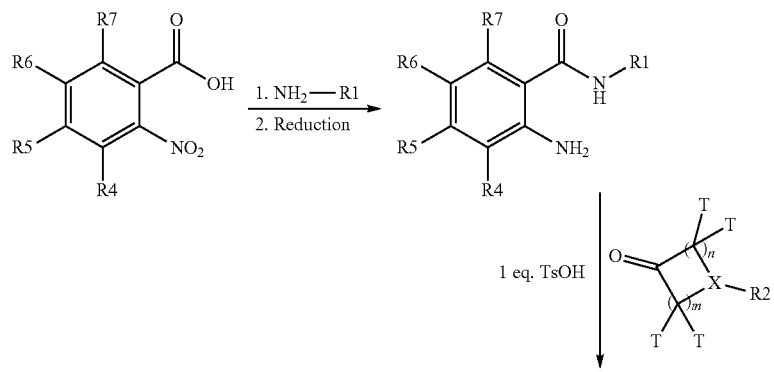

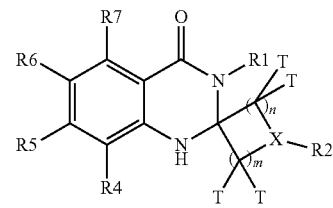

Example 1

Synthesis of Compound 66 (3'-(4-Methoxyphenyl)-1-(2-(trifluoromethyl)benzyl)-1'H-spiro[piperidine-4,2'-quinazolin]-4'(3'H)-one)

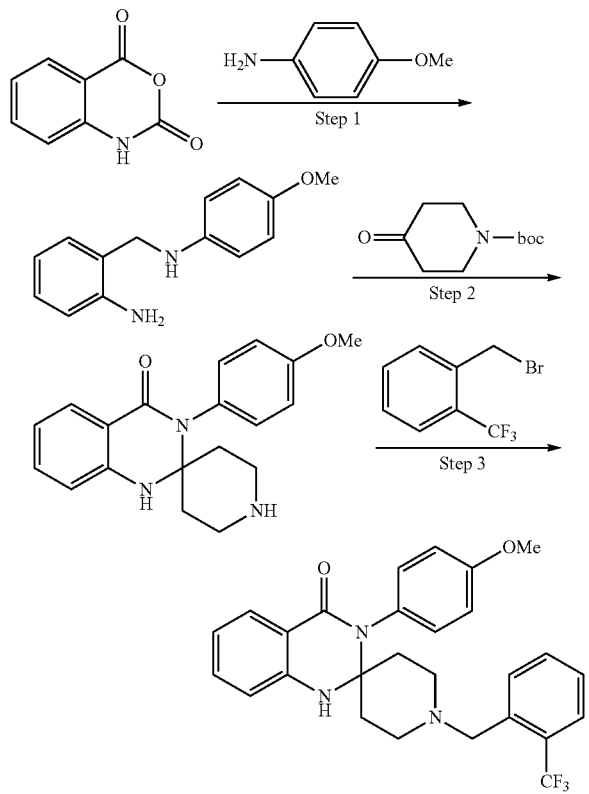

Step 1: To a 500-mL round bottom flask with magnetic stir bar under a nitrogen atmosphere at 25° C. was added isatoic anhydride (10.0 g, 61.4 mmol) and anhydrous toluene (200 mL). The p-anisidine (7.9 g, 64.5 mmol) was added and the reaction vessel was heated at 100-105° C. for 6 h. The reaction temperature was subsequently reduced to 85° C. with stirring overnight. Upon completion the material was purified via silica gel column using ethyl acetate/dichloromethane as the eluent to give 2-amino-N-(4-methoxyphenyl)-benzamide (9.59 g; 65%).

Step 2: To a 250-mL round bottom flask with magnetic stir bar under a nitrogen atmosphere at 25° C. was added 2-amino-N-(4-methoxy-phenyl)-benzamide (1.0 g, 4.17 mmol) and anhydrous toluene (20 mL). The 4-oxo-piperidine-1-carboxylic acid tert-butyl ester (0.83 g, 4.17 mmol) was added followed by toluene-4-sulfonic acid monohydrate (PTSA) (0.14 g, 0.83 mmol) and refluxed at 140° C. for 1 h. The reaction was cooled to 40° C. and another portion of PTSA (0.57 g, 3.3 mmol) was added. The reaction vessel was heated for another hour at 140° C. The reaction was cooled to room temperature and the solvent evaporated in vacuo. After washing the residue with ethyl acetate (2×10 mL), the material was re-dissolved in methanol and dried thoroughly in vacuo to give the tosylate salt of 3'-(4-methoxyphenyl)-1'H-spiro[piperidine-4,2'-quinazolin]-4'(3'H)-one (1.79 g; 87%).

Step 3:
To a 40-mL vial with magnetic stir bar under a nitrogen atmosphere at 25° C. was added the tosylate salt of 3'-(4-methoxyphenyl)-1'H-spiro[piperidine-4,2'-quinazolin]-4'(3'H)-one (0.12 g, 0.24 mmol) and acetonitrile (3 mL). Cesium carbonate (0.24 g, 0.73 mmol) was added followed by drop-wise addition of a solution of 2-trifluoromethylbenzyl bromide (0.06 g, 0.04 mL, 0.25 mmol) in acetonitrile (2 mL). The reaction mixture was stirred at 25° C. overnight. The reaction mixture was diluted with dichloromethane (15 mL) to which saturated aqueous $NaHCO_3$ (10 mL) was added. The layers were separated, and the aqueous layer was extracted with dichloromethane (3×10 mL). The combined organic phase was washed with brine (10 mL), dried over anhydrous sodium sulfate, filtered, and evaporated in vacuo. The resulting residue was purified via silica gel column using ethyl acetate/dichloromethane as the eluent to give title compound 3'-(4-methoxyphenyl)-1-(2-(trifluoromethyl)benzyl)-1'H-spiro[piperidine-4,2'-quinazolin]-4'(3'H)-one (75 mg; 65%); LCMS (ESI) 482 (M+H); $^1$H NMR (400 MHz, DMSO-$d_6$) δ ppm: 1.61 (td, J=12.7, 4.4 Hz, 2H), 1.95 (dd, J=12.4, 0.7 Hz, 2H), 2.40-2.47 (m, 2H), 2.54-2.61 (m, 2H), 3.62 (s, 2H), 3.80 (s, 3H), 6.71-6.77 (m, 1H), 6.92 (s, 1H), 6.96-7.02 (m, 2H), 7.06 (d, J=7.8 Hz, 1H), 7.09-7.14 (m, 2H), 7.33 (td, J=7.6, 1.6 Hz, 1H), 7.38-7.45 (m, 1H), 7.58-7.67 (m, 4H); $^{19}$F NMR (376 MHz, DMSO-$d_6$) δ ppm: −58.31 (br.s., 3F).

The following compounds were synthesized in an analogous manner:

Compound 67 (3'-(4-Methoxyphenyl)-1-(2-(trifluoromethoxy)benzyl)-1'H-spiro[piperidine-4,2'-quinazolin]-4'(3'H)-one); LCMS (ESI) 498 (M+H)

Compound 104 (1-(3-Chlorobenzyl)-3'-(4-methoxyphenyl)-1'H-spiro[piperidine-4,2'-quinazolin]-4'(3'H)-one); LCMS (ESI) 448 (M+H)

Compound 111 (1-(2-Chlorobenzyl)-3'-(4-methoxyphenyl)-1'H-spiro[piperidine-4,2'-quinazolin]-4'(3'H)-one); LCMS (ESI) 448 (M+H)

Compound 114 (1-(4-Fluorobenzyl)-3'-(4-methoxyphenyl)-1'H-spiro[piperidine-4,2'-quinazolin]-4'(3'H)-one); LCMS (ESI) 432 (M+H)

Compound 96 (3'-(4-Methoxyphenyl)-1-(3-(trifluoromethyl)benzyl)-1'H-spiro[piperidine-4,2'-quinazolin]-4'(3'H)-one); LCMS (ESI) 482 (M+H)

Compound 80 (1-(3,5-Difluorobenzyl)-3'-(4-methoxyphenyl)-1'H-spiro[piperidine-4,2'-quinazolin]-4'(3'H)-one); LCMS (ESI) 450 (M+H)

Compound 105 (1-(3,5-Dimethylbenzyl)-3'-(4-methoxyphenyl)-1'H-spiro[piperidine-4,2'-quinazolin]-4'(3'H)-one); LCMS (ESI) 442 (M+H)

Compound 109 (3'-(4-Methoxyphenyl)-1-(2-methylbenzyl)-1'H-spiro[piperidine-4,2'-quinazolin]-4'(3'H)-one); LCMS (ESI) 428 (M+H)

Compound 75 (3-((7'-Chloro-3'-(4-methoxyphenyl)-4'-oxo-3',4'-dihydro-1'H-spiro[piperidine-4,2'-quinazolin]-1-yl)methyl)benzonitrile); LCMS (ESI) 473 (M+H)

Compound 38 (7'-Chloro-1-(3-chlorobenzyl)-3'-(4-methoxyphenyl)-1'H-spiro[piperidine-4,2'-quinazolin]-4'(3'H)-one); LCMS (ESI) 482 (M+H)

Compound 62 (7'-Chloro-1-(2-chlorobenzyl)-3'-(4-methoxyphenyl)-1'H-spiro[piperidine-4,2'-quinazolin]-4'(3'H)-one); LCMS (ESI) 482 (M+H)

Compound 115 (1-(2,5-Dichlorobenzyl)-3'-(3-methoxyphenyl)-1'H-spiro[piperidine-4,2'-quinazolin]-4'(3'H)-one); LCMS (ESI) 482 (M+H)

Compound 116 (2-((3'-(4-Methoxyphenyl)-4'-oxo-3',4'-dihydro-1'H-spiro[piperidine-4,2'-quinazolin]-1-yl)methyl)benzonitrile); LCMS (ESI) 439 (M+H)

Compound 55 (3'-(4-Methoxyphenyl)-1-(3-(trifluoromethoxy)benzyl)-1'H-spiro[piperidine-4,2'-quinazolin]-4'(3'H)-one); LCMS (ESI) 498 (M+H)

Compound 13 (1-(2,5-Dichlorobenzyl)-3'-(4-methoxyphenyl)-1'H-spiro[piperidine-4,2'-quinazolin]-4'(3'H)-one); LCMS (ESI) 482 (M+H)

Compound 54 (1-(3,4-Dichlorobenzyl)-3'-(4-methoxyphenyl)-1'H-spiro[piperidine-4,2'-quinazolin]-4'(3'H)-one); LCMS (ESI) 482 (M+H); $^1$H NMR (400 MHz, DMSO-$d_6$) δ ppm: 1.58 (td, J=12.9, 4.5 Hz, 2H), 1.93 (d, J=12.2 Hz, 2H), 2.37 (t, J=11.8 Hz, 2H), 2.56 (d, J=11.8 Hz, 2H), 3.44 (s, 2H) 3.80 (s, 3H), 6.71-6.77 (m, 1H), 6.89 (s, 1H), 6.96-7.00 (m, 2H), 7.02 (d, J=7.8 Hz, 1H), 7.07-7.13 (m, 2H), 7.22 (dd, J=8.3, 1.9 Hz, 1H), 7.32 (ddd, J=8.3, 7.1, 1.6 Hz, 1H), 7.46 (d, J=1.9 Hz, 1H), 7.53 (d, J=8.2 Hz, 1H), 7.65 (dd, J=7.8, 1.4 Hz, 1H)

Compound 100 (3-((7'-Methoxy-3'-(4-methoxyphenyl)-4'-oxo-3',4'-dihydro-1'H-spiro[piperidine-4,2'-quinazolin]-1-yl)methyl)benzonitrile); LCMS (ESI) 469 (M+H)

Compound 68 (1-(3-Fluorobenzyl)-7'-methoxy-3'-(4-methoxyphenyl)-1'H-spiro[piperidine-4,2'-quinazolin]-4'(3'H)-one); LCMS (ESI) 462 (M+H)

Compound 39 (1-(3,4-Difluorobenzyl)-7'-methoxy-3'-(4-methoxyphenyl)-1'H-spiro[piperidine-4,2'-quinazolin]-4'(3'H)-one); LCMS (ESI) 480 (M+H); $^1$H NMR (400 MHz, DMSO-$d_6$) δ ppm: 1.56 (td, J=12.8, 4.4 Hz, 2H), 1.93 (d, J=12.0 Hz, 2H), 2.35 (td, J=11.7, 0.8 Hz, 2H), 2.56 (d, J=11.6 Hz, 2H), 3.42 (s, 2H), 3.77 (s, 3H), 3.79 (s, 3H), 6.32 (dd, J=8.7, 2.4 Hz, 1H), 6.57 (d, J=2.4 Hz, 1H), 6.91 (s, 1H), 6.94-6.99 (m, 2H), 7.03-7.10 (m, 3H), 7.25 (ddd, J=11.7, 8.0, 1.9 Hz, 1H), 7.32 (dt, J=10.8, 8.5 Hz, 1H), 7.56 (d, J=8.6 Hz, 1H); $^{19}$F NMR (376 MHz, DMSO-$d_6$) δ ppm: −141.82 (d, J=9.8 Hz, 1F), −139.78--139.47 (m, 1F)

Compound 59 (1-((5-Chlorothiophen-2-yl)methyl)-7'-methoxy-3'-(4-methoxyphenyl)-1'H-spiro[piperidine-4,2'-quinazolin]-4'(3'H)-one); LCMS (ESI) 484 (M+H); $^1$H NMR (400 MHz, DMSO-$d_6$) δ ppm: 1.55 (td, J=12.9, 4.1 Hz, 2H), 1.94 (d, J=12.1 Hz, 2H), 2.32-2.42 (m, 2H), 2.64 (d, J=11.9 Hz, 2H), 3.58 (s, 2H), 3.76 (s, 3H), 3.80 (s, 3H), 6.32 (dd, J=8.7, 2.4 Hz, 1H) 6.56 (d, J=2.4 Hz, 1H), 6.80 (d, J=3.7 Hz, 1H), 6.91 (d, J=3.7 Hz, 2H), 6.95-7.00 (m, 2H), 7.06-7.11 (m, 2H), 7.56 (d, J=8.67 Hz, 1H)

Compound 17 (7'-Bromo-1-(3,4-difluorobenzyl)-3'-(4-methoxyphenyl)-1'H-spiro[piperidine-4,2'-quinazolin]-4'(3'H)-one); LCMS (ESI) 528 (M+H); $^1$H NMR (400 MHz, DMSO-$d_6$) δ ppm: 1.58 (td, J=12.8, 4.3 Hz, 2H), 1.93 (d, J=12.4 Hz, 2H), 2.28-2.38 (m, 2H), 2.58 (d, J=12.1 Hz, 2H), 3.42 (s, 2H), 3.79 (s, 3H), 6.89 (dd, J=8.3, 1.9 Hz, 1H), 6.95-7.01 (m, 2H) 7.04-7.08 (m, 1H), 7.08-7.13 (m, 2H), 7.15 (s, 1H), 7.21-7.26 (m, 1H), 7.28 (d, J=1.8 Hz, 1H), 7.32 (dt, J=10.8, 8.5 Hz, 1H), 7.56 (d, J=8.3 Hz, 1H); $^{19}$F NMR (376 MHz, DMSO-$d_6$) δ ppm: −141.76 (d, J=9.4 Hz, 1F), −139.79--139.51 (m, 1F)

Example 2

Synthesis of Compound 28 (1-Benzyl-7'-bromo-3'-(4-(trifluoromethoxy)phenyl)-1'H-spiro[piperidine-4,2'-quinazolin]-4'(3'H)-one)

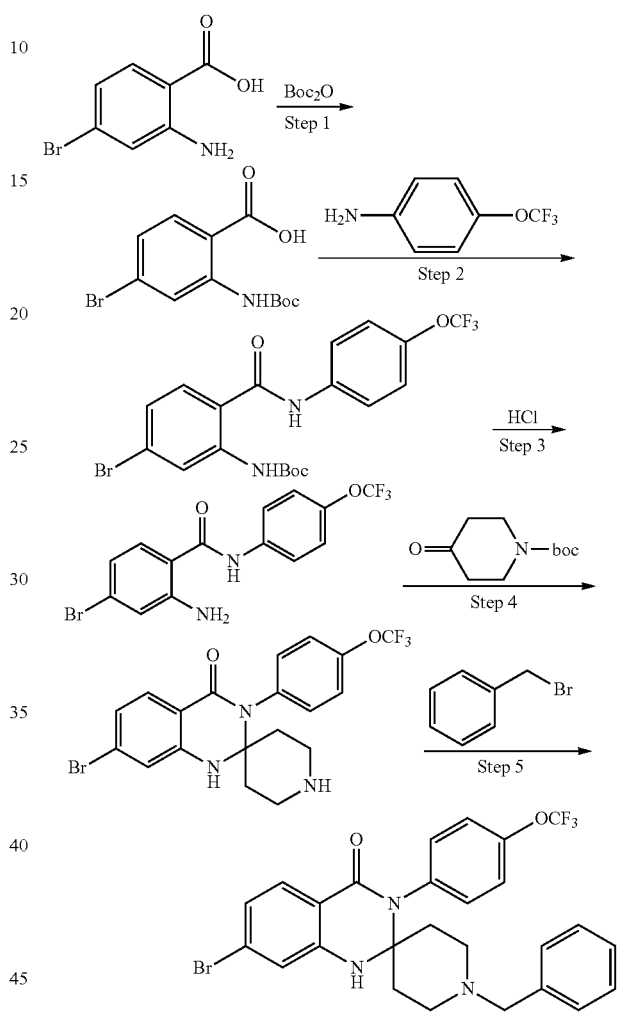

Step 1: To a 250-mL round bottom flask was added 2-amino-4-bromo-benzoic acid (2.5 g, 11.6 mmol) and anhydrous dimethyl formamide (45 mL). Triethylamine (4.8 mL, 34.7 mmol) was subsequently added followed by the di-tert-butyl dicarbonate (3.8 g, 17.4 mmol). The reaction mixture was stirred heated at 50° C. overnight. The reaction mixture was cooled to room temperature and poured into a flask containing water (150 mL). The resulting mixture was washed with ethyl acetate (2×10 mL). The aqueous phase was acidified to a pH range of 4-5 with 10% v/v aqueous HCl solution. The acidified mixture was extracted with dichloromethane (3×50 mL). The combined organic phase was washed with brine (15 mL), dried over anhydrous sodium sulfate, filtered, and evaporated in vacuo to give 4-bromo-2-tert-butoxycarbonylamino-benzoic acid (3.4 g; 94%) as beige solid.

Step 2: To a 200-mL round bottom flask was added 4-bromo-2-tert-butoxycarbonylamino-benzoic acid (2.05 g, 6.48 mmol) and anhydrous dimethyl formamide (40 mL).

Ethyl-(N',N'-dimethylamino)propylcarbodiimide (1.2 g, 1.4 mL, 7.8 mmol) was subsequently added followed by HOBt (1.05 g, 7.8 mmol). Stirring was continued for 30 minutes then 4-trifluoromethoxyaniline (1.2 g, 6.8 mmol) was added. Stirring was continued at 25° C. overnight. The reaction mixture was quenched by pouring into a flask containing water (150 mL) and stirred vigorously. The resulting mixture was extracted with ethyl acetate (3×50 mL). The combined organic phase was washed with water (15 mL), brine (15 mL), dried over anhydrous sodium sulfate, filtered, and evaporated in vacuo. The resulting residue was purified via silica gel column using ethyl acetate heptane as the eluent to give [5-bromo-2-(4-trifluoromethoxy-phenylcarbamoyl)-phenyl]-carbamic acid tert-butyl ester (1.56 g; 51%) as a light yellow solid.

Step 3: To a 40 mL vial was added [5-bromo-2-(4-trifluoromethoxy-phenylcarbamoyl)-phenyl]-carbamic acid tert-butyl ester (1.56 g, 3.29 mmol) and THF (5 mL). The reaction vial was cooled to 0° C. then 4M HCl in 1,4-dioxane (20 mL) was added with vigorous stirring. The mixture was stirred overnight and allowed to equilibrate to 25° C. The precipitate was collected by filtration and dried thoroughly in vacuo to give 2-amino-4-bromo-N-(4-trifluoromethoxy-phenyl)-benzamide (0.98 g; 79%) as an off-white solid.

Step 4: To a 250-mL round bottom flask was added the 2-amino-4-bromo-N-(4-trifluoromethoxy-phenyl)-benzamide (0.75 g, 2 mmol), anhydrous toluene (15 mL), and anhydrous THF (3 mL). The 4-oxo-piperidine-1-carboxylic acid tert-butyl ester (0.4 g, 2 mmol) was added along with toluene-4-sulfonic acid (PTSA) (0.69 g, 0.4 mmol). The flask was refluxed at 140° C. for 1 h. The flask was then cooled to 40° C. and another portion of PTSA (0.28 g, 1.6 mmol) was added. The flask was heated once again to 140° C. for 1 h. The flask was allowed to cool to room temperature and the contents filtered. After washing the residue with ethyl acetate (2×10 mL), the material was re-dissolved in ethyl acetate/methanol (4:1) and dried thoroughly in vacuo to give the tosylate salt of 7'-bromo-3'-(4-(trifluoromethoxy)phenyl)-1'H-spiro[piperidine-4,2'-quinazolin]-4'(3'H)-one (1.3 g; 103%) as a yellow solid.

Step 5: To a 40 mL vial was added the tosylate salt of 7'-bromo-3'-(4-(trifluoromethoxy)phenyl)-1'H-spiro[piperidine-4,2'-quinazolin]-4'(3'H)-one (80 mg, 0.12 mmol) and acetonitrile (3 mL). Cesium carbonate (0.12 g, 0.36 mmol) was added followed by drop-wise addition of a solution of benzyl bromide (22 mg, 20 µL, 0.13 mmol) in acetonitrile (2 mL). The reaction mixture was stirred at 25° C. overnight. The reaction mixture was evaporated in vacuo and the resulting residue was re-dissolved in dichloromethane (5 mL) to which saturated aqueous NaHCO$_3$ (5 mL) was added. The layers were separated, and the aqueous layer was extracted with dichloromethane (3×10 mL). The combined organic phase was washed with brine (5 mL), dried over anhydrous sodium sulfate, filtered, and evaporated in vacuo. The resulting residue was purified via silica gel column using ethyl acetate heptane as eluent to give title compound 1-benzyl-7'-bromo-3'-(4-(trifluoromethoxy)phenyl)-1'H-spiro[piperidine-4,2'-quinazolin]-4'(3'H)-one (43.9 mg; 66%); LCMS (ESI) 546 (M+H); $^1$H NMR (400 MHz, DMSO-d$_6$) δ ppm: 1.50-1.60 (m, 2H), 1.98 (d, J=12.3 Hz, 2H), 2.29-2.38 (m, 2H), 2.60 (d, J=11.8 Hz, 2H), 3.43 (s, 2H), 6.91 (dd, J=8.3, 1.9 Hz, 1H), 7.18-7.24 (m, 4H), 7.25-7.32 (m, 3H), 7.34-7.39 (m, 2H), 7.42-7.47 (m, 2H), 7.57 (d, J=8.3 Hz, 1H); $^{19}$F NMR (376 MHz, DMSO-d$_6$) δ ppm: −57.18 (br.s., 3F).

The following compounds were synthesized in an analogous manner:

Compound 32 (7'-Bromo-1-(3,4-difluorobenzyl)-3'-(4-(trifluoromethoxy)phenyl)-1'H-spiro[piperidine-4,2'-quinazolin]-4'(3'H)-one); LCMS (ESI) 515 (M+H); $^1$H NMR (400 MHz, CHLOROFORM-d) δ ppm: 7.81 (d, J=8.3 Hz, 1H), 7.17-7.37 (m, 4H), 7.02-7.15 (m, 3H), 7.00 (d, J=1.5 Hz, 1H), 6.95 (br.s., 1H), 4.72 (s, 1H), 3.43 (s, 2H), 2.77 (d, J=12.0 Hz, 2H), 1.97-2.27 (m, 4H), 1.79 (td, J=12.8, 4.3 Hz, 2H)

Compound 103 (7'-Bromo-1-(pyridin-2-ylmethyl)-3'-(4-(trifluoromethoxy)phenyl)-1'H-spiro[piperidine-4,2'-quinazolin]-4'(3'H)-one); LCMS (ESI) 549 (M+H)

Compound 8 (7'-Bromo-1-(1-(3,4-difluorophenyl)ethyl)-3'-(4-(trifluoromethoxy)phenyl)-1'H-spiro[piperidine-4,2'-quinazolin]-4'(3'H)-one); LCMS (ESI) 596 (M+H); $^1$H NMR (400 MHz, CHLOROFORM-d) δ ppm: 7.80 (d, J=8.3 Hz, 1H), 7.21-7.33 (m, 5H), 7.01-7.12 (m, 2H), 6.96 (d, J=1.6 Hz, 2H), 4.68 (s, 1H), 3.35 (q, J=6.6 Hz, 1H), 2.96 (d, J=11.6 Hz, 1H), 2.66 (d, J=12.3 Hz, 1H), 2.08-2.17 (m, 2H), 1.97-2.06 (m, 2H), 1.64-1.85 (m, 2H), 1.29 (d, J=6.7 Hz, 3H)

Compound 48 (7'-Bromo-1-(1-phenylpropyl)-3'-(4-(trifluoromethoxy)phenyl)-1'H-spiro[piperidine-4,2'-quinazolin]-4'(3'H)-one); LCMS (ESI) 574 (M+H). $^1$H NMR (400 MHz, CHLOROFORM-d) δ ppm: 7.78 (d, J=8.3 Hz, 1H), 7.20-7.36 (m, 8H), 7.16 (d, J=6.8 Hz, 2H), 7.00 (dd, J=8.3, 1.6 Hz, 1H), 6.86 (d, J=1.6 Hz, 1H), 4.63 (s, 1H), 3.19 (dd, J=9.2, 5.1 Hz, 1H), 2.96 (d, J=12.3 Hz, 1H), 2.74 (d, J=12.3 Hz, 1H), 2.04-2.15 (m, 2H), 1.80-2.03 (m, 4H), 1.62-1.75 (m, 2H), 0.70 (t, J=7.3 Hz, 3H)

Compound 118 (7'-Bromo-1-(pyridin-3-ylmethyl)-3'-(4-(trifluoromethoxy)phenyl)-1'H-spiro[piperidine-4,2'-quinazolin]-4'(3'H)-one); LCMS (ESI) 496 (M+H)

Compound 97 (7'-Bromo-1-(pyridin-4-ylmethyl)-3'-(4-(trifluoromethoxy)phenyl)-1'H-spiro[piperidine-4,2'-quinazolin]-4'(3'H)-one); LCMS (ESI) 547 (M+H)

Compound 22 (7'-Bromo-1-(1-(3,4-difluorophenyl)propyl)-3'-(4-(trifluoromethoxy)phenyl)-1'H-spiro[piperidine-4,2'-quinazolin]-4'(3'H)-one); LCMS (ESI) 610 (M+H); $^1$H NMR (400 MHz, CHLOROFORM-d) δ ppm: 7.79 (d, J=8.3 Hz, 1H), 7.21-7.33 (m, 5H), 7.07-7.15 (m, 1H), 6.97-7.05 (m, 2H), 6.85-6.93 (m, 2H), 4.63 (s, 1H), 3.13 (dd, J=9.0, 4.8 Hz, 1H), 2.96 (d, J=11.6 Hz, 1H), 2.67 (d, J=12.1 Hz, 1H), 2.05-2.15 (m, 2H), 1.76-2.03 (m, 4H), 1.59-1.71 (m, 2H), 0.69 (t, J=7.3 Hz, 3H)

Compound 46 (7'-Bromo-1-(2-(trifluoromethoxy)benzyl)-3'-(4-(trifluoromethoxy)phenyl)-1'H-spiro[piperidine-4,2'-quinazolin]-4'(3'H)-one); LCMS (ESI) 630 (M+H); $^1$H NMR (400 MHz, DMSO-d$_6$) δ ppm: 1.56 (td, J=12.9, 4.3 Hz, 2H), 1.99 (d, J=12.5 Hz, 2H), 2.42 (t, J=11.7 Hz, 2H), 2.60 (d, J=10.6 Hz, 2H), 3.52 (s, 2H), 6.92 (dd, J=8.3, 1.9 Hz, 1H), 7.24 (s, 1H), 7.27-7.31 (m, 1H), 7.31-7.33 (m, 1H), 7.34-7.38 (m, 4H), 7.45 (d, J=9.1 Hz, 3H), 7.57 (d, J=8.3 Hz, 1H); $^{19}$F NMR (376 MHz, DMSO-d$_6$) δ ppm: −57.24 (br.s., 3F), −56.43 (br.s., 3F)

Compound 24 (7'-Bromo-1-(3,4-difluorobenzyl)-3'-(3-fluoro-4-methoxyphenyl)-1'H-spiro[piperidine-4,2'-quinazolin]-4'(3'H)-one); LCMS (ESI) 546 (M+H); $^1$H NMR (400 MHz, DMSO-d$_6$) δ ppm: 7.56 (d, J=8.3 Hz, 1H), 7.22-7.37 (m, 3H), 7.12-7.22 (m, 3H), 7.04-7.10 (m, 1H), 6.98-7.03 (m, 1H), 6.90 (dd, J=8.3, 1.9 Hz, 1H), 3.88 (s, 3H), 3.43 (s, 2H), 2.59 (d, J=11.9 Hz, 2H), 2.28-2.38 (m, 2H), 1.95 (d, J=13.2 Hz, 2H), 1.59 (td, J=12.9, 4.5 Hz, 2H); $^{19}$F NMR (376 MHz, DMSO-d$_6$) δ ppm: −141.76 (d, J=9.8 Hz, 1F), −139.74--139.45 (m, 1F), −134.81 (br.s., 1F)

Compound 102 (7'-Bromo-3'-(3-chloro-4-(trifluoromethoxy)phenyl)-1-(3,4-difluorobenzyl)-1'H-spiro[piperidine-4,2'-quinazolin]-4'(3'H)-one); LCMS (ESI) 616 (M+H)

Compound 5 (7'-Bromo-1-(3,4-difluorobenzyl)-3'-(4-(methylthio)phenyl)-1'H-spiro[piperidine-4,2'-quinazolin]-4'(3'H)-one); LCMS (ESI) 544 (M+H); $^1$H NMR (400 MHz, DMSO-$d_6$) δ ppm: 7.82 (d, J=8.3 Hz, 1H), 7.32 (d, J=8.4 Hz, 2H), 7.01-7.16 (m, 5H), 6.91-7.01 (m, 2H), 4.72 (s, 1H), 3.42 (s, 2H), 2.75 (d, J=12.1 Hz, 2H), 2.52 (s, 3H), 2.01-2.18 (m, 4H), 1.76-1.88 (m, 2H)

Compound 10 (1-(3-Chlorobenzyl)-3'-(4-(trifluoromethoxy)phenyl)-7'-(trifluoromethyl)-1'H-spiro[piperidine-4,2'-quinazolin]-4'(3'H)-one); LCMS (ESI) 570 (M+H); $^1$H NMR (400 MHz, DICHLOROMETHANE-$d_2$) δ ppm: 8.01 (d, J=7.9 Hz, 1H), 7.31-7.37 (m, 2H), 7.24-7.31 (m, 3H), 7.19-7.24 (m, 2H), 7.10-7.17 (m, 3H), 3.45 (s, 2H), 2.71-2.83 (m, 2H), 2.18 (td, J=12.5, 2.1 Hz, 2H), 2.07 (d, J=10.9 Hz, 2H), 1.73-1.86 (m, 2H), 1.53 (s, 1H)

Example 3

Synthesis of Compound 27 (7'-Bromo-1-(isoquinolin-5-ylmethyl)-3'-(4-(trifluoromethoxy)phenyl)-1'H-spiro[piperidine-4,2'-quinazolin]-4'(3'H)-one)

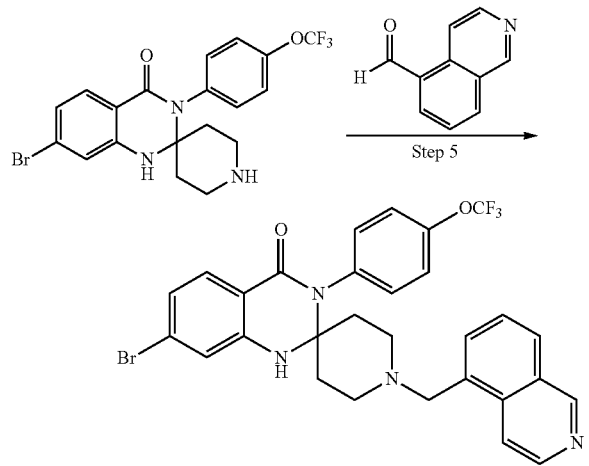

Prepared following the same procedure as example 2 until step 4.

Step 5: To a 40 mL vial was added the tosylate salt of 7'-bromo-3'-(4-(trifluoromethoxy)phenyl)-1'H-spiro[piperidine-4,2'-quinazolin]-4'(3'H)-one (75 mg, 0.12 mmol) and anhydrous methanol (3 mL). Triethylamine (19 µL, 0.14 mmol) was added and the mixture stirred at 25° C. for 15 minutes. Glacial acetic acid (2 drops) was then added followed by isoquinoline-5-carbaldehyde (20 mg, 0.13 mmol) and drop-wise addition of sodium cyanoborohydride solution (1M in THF) (0.27 mL, 0.27 mmol). The reaction was stirred at 25° C. overnight. The reaction was diluted with ethyl acetate (10 mL). The resulting mixture was then added drop-wise to a dilute mixture (~5% w/v) of aqueous sodium carbonate (10 mL). The layers were separated and the aqueous layer extracted with ethyl acetate (3×10 mL). The combined organicphase was washed with brine (10 mL), dried over anhydrous sodium sulfate, filtered, and evaporated in vacuo. The resulting residue was purified via silica gel column using ethyl acetate dichloromethane aseluent to give title compound 7'-bromo-1-(isoquinolin-5-ylmethyl)-3'-(4-(trifluoromethoxy)-phenyl)-1'H-spiro[piperidine-4,2'-quinazolin]-4'(3'H)-one (42 mg; 58%); LCMS (ESI) 597 (M+H); $^1$H NMR (400 MHz, DMSO-$d_6$) δ ppm: 1.52 (td, J=12.8, 4.4 Hz, 2H), 1.98 (d, J=12.0 Hz, 2H), 2.41-2.47 (m, 2H), 2.69 (d, J=10.8 Hz, 2H), 3.87 (s, 2H), 6.92 (dd, J=8.3, 1.9 Hz, 1H), 7.27 (s, 1H), 7.31-7.36 (m, 3H), 7.39-7.44 (m, 2H), 7.55-7.65 (m, 3H), 7.94 (d, J=6.0 Hz, 1H), 8.01 (d, J=7.7 Hz, 1H), 8.46 (d, J=5.9 Hz, 1H), 9.27 (s, 1H); $^{19}$F NMR (376 MHz, DMSO-$d_6$) δ ppm: −57.20 (br.s., 3F).

The following compounds were synthesized in an analogous manner:

Compound 120 (7'-Bromo-1-((1-methyl-1H-pyrrol-2-yl)methyl)-3'-(4-(trifluoromethoxy)phenyl)-1'H-spiro[piperidine-4,2'-quinazolin]-4'(3'H)-one); LCMS (ESI) 549 (M+H)

Compound 113 (7'-Bromo-1-((5-methylfuran-2-yl)methyl)-3'-(4-(trifluoromethoxy)phenyl)-1'H-spiro[piperidine-4,2'-quinazolin]-4'(3'H)-one); LCMS (ESI) 550 (M+H)

Compound 57 (7'-Bromo-1-(quinolin-5-ylmethyl)-3'-(4-(trifluoromethoxy)phenyl)-1'H-spiro[piperidine-4,2'-quinazolin]-4'(3'H)-one); LCMS (ESI) 597 (M+H); $^1$H NMR (400 MHz, DMSO-$d_6$) δ ppm: 1.49 (td, J=12.7, 4.25 Hz, 2H), 1.98 (d, J=12.2 Hz, 2H), 2.44 (t, J=11.7 Hz, 2H), 2.69 (d, J=12.5 Hz, 2H), 3.88 (s, 2H), 6.92 (dd, J=8.3, 1.9 Hz, 1H), 7.27 (s, 1H), 7.30-7.35 (m, 3H), 7.38-7.43 (m, 2H), 7.43-7.50 (m, 2H), 7.57 (d, J=8.3 Hz, 1H), 7.66 (dd, J=8.5, 7.0 Hz, 1H), 7.91 (d, J=8.4 Hz, 1H), 8.53 (dd, J=8.5, 0.7 Hz, 1H), 8.86 (dd, J=4.2, 1.6 Hz, 1H); $^{19}$F NMR (376 MHz, DMSO-$d_6$) δ ppm: −57.20 (br.s., 3F)

Compound 47 (7'-Bromo-1-(quinolin-4-ylmethyl)-3'-(4-(trifluoromethoxy)phenyl)-1'H-spiro[piperidine-4,2'-quinazolin]-4'(3'H)-on); LCMS (ESI) 597 (M+H); 1H NMR (400 MHz, DMSO-$d_6$) δ ppm: 1.58 (td, J=13.1, 4.3 Hz, 2H), 1.97-2.04 (m, 2H), 2.47 (br.s., 1H), 2.53 (br.s., 1H), 2.71 (d, J=12.0 Hz, 2H), 3.93 (s, 2H), 6.93 (dd, J=8.3, 1.9 Hz, 1H), 7.29 (s, 1H), 7.33 (d, J=1.9 Hz, 1H), 7.34-7.38 (m, 2H), 7.40 (d, J=4.3 Hz, 1H), 7.42-7.45 (m, 2H), 7.54-7.60 (m, 2H), 7.72 (ddd, J=8.3, 6.9, 1.3 Hz, 1H), 8.00 (dd, J=8.4, 0.7 Hz, 1H), 8.15 (dd, J=8.4, 0.7 Hz, 1H), 8.80 (d, J=4.3 Hz, 1H); $^{19}$F NMR (376 MHz, DMSO-$d_6$) δ ppm: −57.18 (br.s., 3F)

Compound 110 (7'-Bromo-1-((2-bromothiazol-5-yl)methyl)-3'-(4-(trifluoromethoxy)phenyl)-1'H-spiro[piperidine-4,2'-quinazolin]-4'(3'H)-one); LCMS (ESI) 632 (M+H)

Compound 49 (7'-Bromo-1-(2-hydroxybenzyl)-3'-(4-(trifluoromethoxy)phenyl)-1'H-spiro[piperidine-4,2'-quinazolin]-4'(3'H)-one); LCMS (ESI) 562 (M+H); $^1$H NMR (400 MHz, METHANOL-$d_4$) δ ppm: 7.66 (d, J=8.3 Hz, 1H), 7.29-7.48 (m, 4H), 7.15-7.27 (m, 1H), 7.09 (t, J=7.7 Hz, 1H), 6.92-7.04 (m, 2H), 6.63-6.85 (m, 3H), 3.68 (s, 2H), 2.83 (d, J=12.2 Hz, 2H), 2.48 (t, J=11.9 Hz, 2H), 2.16 (d, J=12.1 Hz, 2H), 1.80 (td, J=13.1, 4.3 Hz, 2H)

Compound 42 (3-((4'-Oxo-3'-(4-(trifluoromethoxy)phenyl)-7'-(trifluoromethyl)-3',4'-dihydro-1'H-spiro[piperidine-4,2'-quinazolin]-1-yl)methyl)benzonitrile); LCMS (ESI) 561 (M+H); $^1$H NMR (400 MHz, DICHLOROMETHANE-$d_2$) δ ppm: 8.01 (d, J=8.5 Hz, 1H), 7.66 (td, J=1.6, 0.8 Hz, 1H), 7.55-7.60 (m, 2H), 7.50-7.55 (m, 1H), 7.48-7.50 (m, 1H), 7.37-7.43 (m, 2H), 7.32-7.37 (m, 2H), 7.26-7.31 (m, 2H), 7.13 (s, 2H), 3.50 (s, 3H), 2.66-2.79 (m, 3H), 2.22 (td, J=12.5, 2.0 Hz, 3H), 2.07 (d, J=11.0 Hz, 3H), 1.80 (td, J=12.9, 4.5 Hz, 3H)

Example 4

Synthesis of Compound 122 (1-(3,4-Difluorobenzyl)-6'-hydroxy-3'-(4-methoxyphenyl)-1'H-spiro[piperidine-4,2'-quinazolin]-4'(3'H)-one)

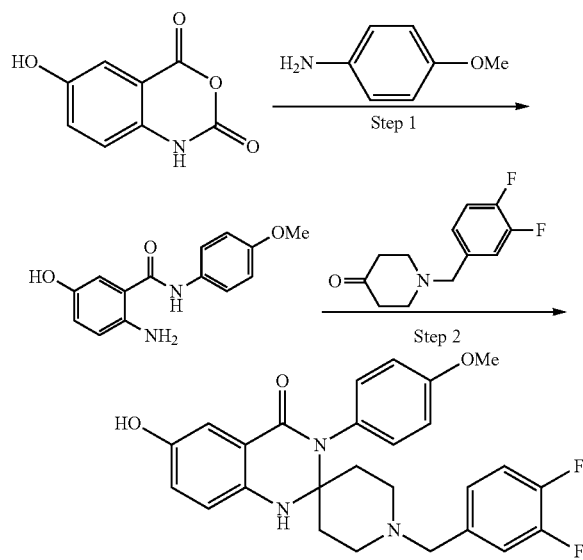

Step 1: Prepared following the same procedure as example 1, step 1 to give 2-amino-5-hydroxy-N-(4-methoxy-phenyl)-benzamide (215 mg; 15%); LCMS (ESI) 562 (M+H); ¹H NMR (400 MHz, DMSO-d₆) δ ppm: 9.89 (s, 1H), 8.66 (s, 1H), 7.58-7.64 (m, 2H), 6.99 (d, J=2.7 Hz, 1H), 6.86-6.92 (m, 2H), 6.73 (dd, J=8.7, 2.7 Hz, 1H), 6.61 (d, J=8.7 Hz, 1H), 5.59 (br.s., 2H), 3.73 (s, 3H).

Step 2: A round bottom flask was charged with 2-amino-5-hydroxy-N-(4-methoxy-phenyl)-benzamide (0.22 g, 0.83 mmol), 1-(3,4-difluoro-benzyl)-piperidin-4-one (207 mg, 0.92 mmol), para-toluene sulphonic acid mono hydrate (0.03 g, 0.17 mmol) and toluene (10 mL). The mixture was heated at 140° C. bath temperature for 2 h which formed a precipitate. The mixture was cooled, the solvent evaporated in vacuo and the residue was dissolved in DCM and a saturated aqueous solution of sodium bicarbonate. The aqueous phase was extracted with DCM, the combined organic phase was washed with brine, dried over anhydrous sodium sulfate, filtered, and evaporated in vacuo. The residue purified via silica gel column using ethyl acetate/dichloromethane as eluent to give title compound 1-(3,4-difluorobenzyl)-6'-hydroxy-3'-(4-methoxyphenyl)-1'H-spiro[piperidine-4,2'-quinazolin]-4'(3'H)-one (152 mg; 39%) as a light orange solid; LCMS (ESI) 466 (M+H); ¹H NMR (400 MHz, DMSO-d₆) δ ppm: 8.91 (s, 1H), 7.31 (dt, J=10.8, 8.4 Hz, 1H), 7.24 (ddd, J=11.6, 8.0, 1.9 Hz, 1H), 7.02-7.11 (m, 4H), 6.95-7.01 (m, 2H), 6.86-6.90 (m, 1H), 6.80-6.85 (m, 1H), 6.20 (s, 1H), 3.79 (s, 3H), 3.40 (s, 2H), 2.54 (br.s., 2H), 2.32 (t, J=11.4 Hz, 2H), 1.90 (d, J=12.2 Hz, 2H), 1.54 (td, J=12.8, 4.2 Hz, 2H); ¹⁹F NMR (376 MHz, DMSO-d₆) δ ppm: −141.83 (d, J=9.2 Hz, 1F) −139.88-−139.43 (m, 1F).

The following compounds were synthesized in an analogous manner:

Compound 25 (7'-Bromo-3'-(4-chlorophenyl)-1-(3,4-difluorobenzyl)-1'H-spiro[piperidine-4,2'-quinazolin]-4'(3'H)-one); LCMS (ESI) 532 (M+H)

Compound 71 (1-Benzyl-7'-bromo-3'-(4-chlorophenyl)-1'H-spiro[piperidine-4,2'-quinazolin]-4'(3'H)-one); LCMS (ESI) 496 (M+H)

Compound 36 (Methyl 1-(3,4-difluorobenzyl)-4'-oxo-3'-(4-(trifluoromethoxy)phenyl)-3',4'-dihydro-1'H-spiro[piperidine-4,2'-quinazoline]-7'-carboxylate); LCMS (ESI) 562 (M+H); ¹H NMR (400 MHz, DMSO-d₆) δ ppm: 7.68-7.82 (m, 2H), 7.42-7.49 (m, 2H), 7.36-7.41 (m, 2H), 7.20-7.34 (m, 4H), 7.07 (br.s., 1H), 3.87 (s, 3H), 3.43 (s, 2H), 2.58 (d, J=11.6 Hz, 2H), 2.28-2.45 (m, 2H), 1.90-2.06 (m, 2H), 1.46-1.68 (m, 2H)

Compound 51 (3'-(4-Bromophenyl)-1-(3,4-difluorobenzyl)-7'-fluoro-1'H-spiro[piperidine-4,2'-quinazolin]-4'(3'H)-one); LCMS (ESI) 516 (M+H); ¹H NMR (400 MHz, DMSO-d₆) δ ppm: 7.70 (dd, J=8.7, 6.7 Hz, 1H), 7.61-7.67 (m, 2H), 7.22-7.37 (m, 3H), 7.16-7.21 (m, 2H), 7.04-7.10 (m, 1H), 6.81 (dd, J=11.0, 2.5 Hz, 1H), 6.55 (td, J=8.7, 2.5 Hz, 1H), 3.43 (s, 2H), 2.59 (d, J=11.9 Hz, 2H), 2.34 (t, J=11.5 Hz, 2H), 1.97 (d, J=12.5 Hz, 2H), 1.57 (td, J=12.8, 4.4 Hz, 2H); ¹⁹F NMR (376 MHz, DMSO-d₆) δ ppm: −141.76 (d, J=7.9 Hz, 1F) −139.73-−139.47 (m, 1F) −106.75 (br.s., 1F)

Compound 2 (7'-Bromo-1-(3,4-difluorobenzyl)-3'-(2-methylbenzofuran-5-yl)-1'H-spiro[piperidine-4,2'-quinazolin]-4'(3'H)-one); LCMS (ESI) 552 (M+H); ¹H NMR (400 MHz, DMSO-d₆) δ ppm: 7.57 (d, J=8.3 Hz, 1H), 7.52 (d, J=8.5 Hz, 1H), 7.37 (d, J=2.0 Hz, 1H), 7.26-7.34 (m, 2H), 7.23 (ddd, J=11.7, 8.0, 1.9 Hz, 1H), 7.18 (s, 1H), 7.03-7.07 (m, 1H), 6.99-7.03 (m, 1H), 6.90 (dd, J=8.3, 1.9 Hz, 1H), 6.59-6.62 (m, 1H), 3.41 (s, 2H), 2.53-2.60 (m, 2H), 2.47 (d, J=0.8 Hz, 3H), 2.28-2.39 (m, 2H), 1.97 (t, J=11.3 Hz, 2H), 1.54-1.68 (m, 2H); ¹⁹F NMR (376 MHz, DMSO-d₆) δ ppm: −141.81 (d, J=9.2 Hz, 1F) −139.81-−139.53 (m, 1F)

Example 5

Synthesis of Compound 1 (Ethyl 1-(3,4-difluorobenzyl)-3'-(4-methoxyphenyl)-4'-oxo-3',4'-dihydro-1'H-spiro[piperidine-4,2'-quinazoline]-7'-carboxylate)

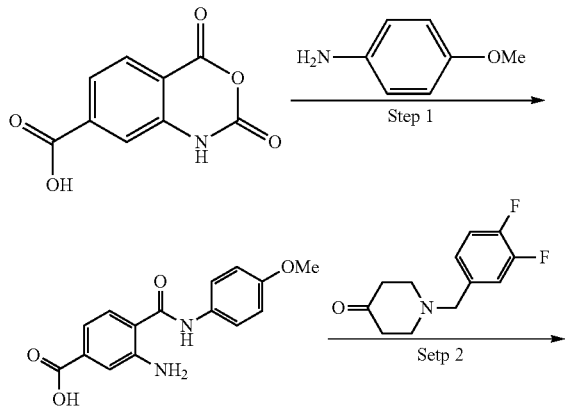

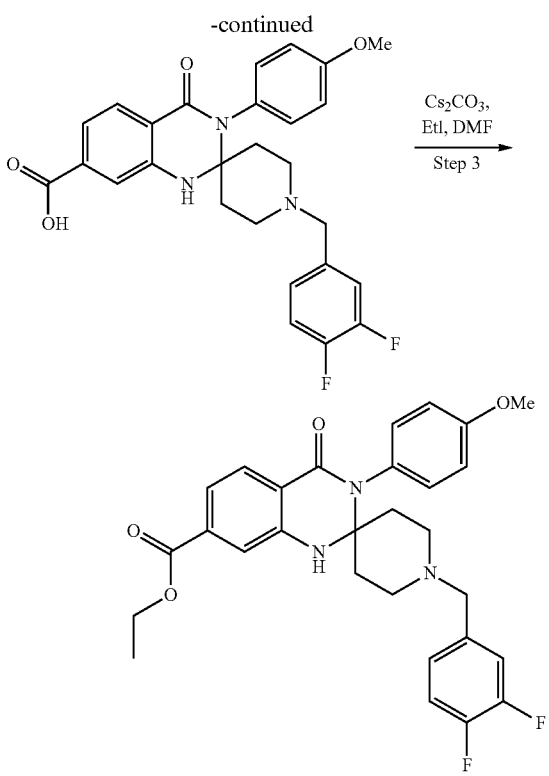

Step 1 and 2: Prepared following the same procedure as example 4, step 1 and 2, to give 1-(3,4-difluorobenzyl)-3'-(4-methoxyphenyl)-4'-oxo-3',4'-dihydro-1'H-spiro[piperidine-4,2'-quinazoline]-7'-carboxylic acid (115 mg; 47%) as a white solid; LCMS (ESI) 494 (M+H). Step 3: A scintillation vial was charged with 1-(3,4-difluorobenzyl)-3'-(4-methoxyphenyl)-4'-oxo-3',4'-dihydro-1'H-spiro[piperidine-4,2'-quinazoline]-7'-carboxylic acid (123 mg, 0.25 mmol), cesium carbonate (242 mg, 0.75 mmol), dimethyl formamide (5 mL) and ethyl iodide (40 mg, 0.25 mmol). The reaction mixture was stirred at room temperature overnight. The reaction was poured into water (50 mL), extracted with ethyl acetate (3×50 mL), the combined organic phase washed with LiCl (aq) (50 mL), dried over anhydrous sodium sulfate, filtered and the solvent was evaporated under reduced pressure. The crude material was purified by chromatography using heptane/ethyl acetate (0-100%) as eluent to give title compound ethyl 1-(3,4-difluorobenzyl)-3'-(4-methoxyphenyl)-4'-oxo-3',4'-dihydro-1'H-spiro[piperidine-4,2'-quinazoline]-7'-carboxylate (19 mg; 14%) as a white solid; LCMS (ESI) 522 (M+H); $^1$H NMR (400 MHz, CHLOROFORM-d) δ ppm: 8.03 (d, J=8.1 Hz, 1H), 7.55 (dd, J=8.1, 1.2 Hz, 1H), 7.49 (s, 1H), 7.15 (d, J=8.8 Hz, 2H), 7.03-7.12 (m, 2H), 6.98 (d, J=8.8 Hz, 3H), 4.79 (s, 1H), 4.40 (q, J=7.1 Hz, 2H), 3.85 (s, 3H), 3.43 (s, 2H), 2.75 (d, J=11.9 Hz, 2H), 2.16 (t, J=11.8 Hz, 2H), 2.05 (d, J=12.1 Hz, 2H), 1.80-1.90 (m, 2H), 1.42 (t, J=7.1 Hz, 3H).

The following compounds were synthesized in an analogous manner:

Compound 3 (Isopropyl 1-(3,4-difluorobenzyl)-3'-(4-methoxyphenyl)-4'-oxo-3',4'-dihydro-1'H-spiro[piperidine-4,2'-quinazoline]-7'-carboxylate); LCMS (ESI) 536 (M+H); $^1$H NMR (400 MHz, CHLOROFORM-d) δ ppm: 7.54 (dd, J=8.1, 1.3 Hz, 1H), 7.47 (s, 1H), 7.15 (d, J=8.8 Hz, 2H), 7.03-7.13 (m, 2H), 6.97 (d, J=8.8 Hz, 3H), 5.27 (spt, J=6.3 Hz, 1H), 4.78 (s, 1H), 3.85 (s, 3H), 3.43 (s, 2H), 2.71-2.78 (m, 3H), 2.47 (t, J=6.1 Hz, 1H), 2.16 (t, J=11.8 Hz, 2H), 2.03 (br.s., 2H), 1.80-1.90 (m, 2H), 1.40 (d, J=6.2 Hz, 5H)

Compound 4 (Methyl 1-(3,4-difluorobenzyl)-3'-(4-methoxyphenyl)-4'-oxo-3',4'-dihydro-1'H-spiro[piperidine-4,2'-quinazoline]-7'-carboxylate); LCMS (ESI) 508 (M+H); $^1$H NMR (400 MHz, CHLOROFORM-d) δ ppm: 8.03 (d, J=8.1 Hz, 1H), 7.54 (dd, J=8.1, 1.3 Hz, 1H), 7.49 (s, 1H), 7.03-7.17 (m, 4H), 6.98 (d, J=8.8 Hz, 3H), 5.31 (s, 1H), 4.79 (s, 1H), 3.94 (s, 3H), 3.85 (s, 3H), 3.42 (s, 2H), 2.75 (d, J=12.0 Hz, 2H), 2.15 (t, J=11.8 Hz, 2H), 2.04 (d, J=9.7 Hz, 2H), 1.80-1.90 (m, 2H)

Compound 15 (Methyl 1-benzyl-3'-(4-methoxyphenyl)-4'-oxo-3',4'-dihydro-1'H-spiro[piperidine-4,2'-quinazoline]-7'-carboxylate); LCMS (ESI) 472 (M+H); H NMR (400 MHz, CHLOROFORM-d) δ ppm: 8.02 (d, J=8.1 Hz, 1H), 7.53 (dd, J=8.1, 1.2 Hz, 1H), 7.49 (s, 1H), 7.19-7.37 (m, 5H), 7.14 (d, J=8.7 Hz, 2H), 6.96 (d, J=8.8 Hz, 2H), 4.83 (s, 1H), 3.76-4.04 (m, 6H), 3.47-3.54 (m, 2H), 2.79 (d, J=12.1 Hz, 2H), 2.14 (t, J=11.9 Hz, 2H), 2.04 (d, J=12.2 Hz, 2H), 1.75-1.91 (m, 2H)

Compound 29 (Ethyl 1-(3,4-difluorobenzyl)-4'-oxo-3'-(4-(trifluoromethoxy)phenyl)-3',4'-dihydro-1'H-spiro[piperidine-4,2'-quinazoline]-7'-carboxylate); LCMS (ESI) 576 (M+H); $^1$H NMR (400 MHz, METHANOL-d$_4$) δ ppm: 7.86 (d, J=8.2 Hz, 1H), 7.69 (d, J=1.1 Hz, 1H), 7.27-7.51 (m, 5H), 7.10-7.24 (m, 2H), 7.07 (br.s., 1H), 4.38 (q, J=7.1 Hz, 2H), 3.48 (s, 2H), 2.71 (d, J=12.0 Hz, 2H), 2.40 (t, J=11.8 Hz, 2H), 2.11 (d, J=12.3 Hz, 2H), 1.79 (td, J=12.9, 4.3 Hz, 2H), 1.41 (t, J=7.1 Hz, 3H)

Compound 31 (Isopropyl 1-(3,4-difluorobenzyl)-4'-oxo-3'-(4-(trifluoromethoxy)phenyl)-3',4'-dihydro-1'H-spiro[piperidine-4,2'-quinazoline]-7'-carboxylate); LCMS (ESI) 590 (M+H); $^1$H NMR (400 MHz, METHANOL-d$_4$) δ ppm: 7.85 (d, J=8.2 Hz, 1H), 7.68 (d, J=1.2 Hz, 1H), 7.31-7.49 (m, 5H), 7.11-7.27 (m, 2H), 7.07 (br.s., 1H), 5.23 (dt, J=12.5, 6.2 Hz, 1H), 3.49 (s, 2H), 2.71 (d, J=12.1 Hz, 2H), 2.40 (t, J=11.7 Hz, 2H), 2.11 (d, J=12.3 Hz, 2H), 1.79 (td, J=12.9, 4.2 Hz, 2H), 1.39 (d, J=6.2 Hz, 6H)

Compound 58 (Cyclopropylmethyl 1-(3,4-difluorobenzyl)-4'-oxo-3'-(4-(trifluoromethoxy)phenyl)-3',4'-dihydro-1'H-spiro[piperidine-4,2'-quinazoline]-7'-carboxylate); LCMS (ESI) 602 (M+H); $^1$H NMR (400 MHz, METHANOL-d$_4$) δ ppm: 7.87 (d, J=8.2 Hz, 1H), 7.71 (d, J=1.2 Hz, 1H), 7.29-7.50 (m, 5H), 7.11-7.26 (m, 2H), 7.08 (d, J=3.8 Hz, 1H), 4.17 (d, J=7.3 Hz, 2H), 3.49 (s, 2H), 2.71 (d, J=12.1 Hz, 2H), 2.41 (t, J=11.7 Hz, 2H), 2.11 (d, J=12.2 Hz, 2H), 1.80 (td, J=12.9, 4.3 Hz, 2H), 0.83-0.92 (m, 1H), 0.52-0.71 (m, 2H), 0.27-0.47 (m, 2H)

Compound 99 (2-Methoxyethyl 1-(3,4-difluorobenzyl)-4'-oxo-3'-(4-(trifluoromethoxy)phenyl)-3',4'-dihydro-1'H-spiro[piperidine-4,2'-quinazoline]-7'-carboxylate); LCMS (ESI) 606 (M+H); $^1$H NMR (400 MHz, METHANOL-d$_4$) δ ppm: 7.87 (d, J=8.2 Hz, 1H), 7.70 (d, J=1.1 Hz, 1H), 7.31-7.52 (m, 5H), 7.11-7.27 (m, 2H), 7.07 (br.s., 1H), 4.37-4.54 (m, 2H), 3.67-3.82 (m, 2H), 3.49 (s, 2H), 3.43 (s, 3H), 2.71 (d, J=12.0 Hz, 2H), 2.41 (t, J=11.7 Hz, 2H), 2.11 (d, J=12.1 Hz, 2H), 1.80 (td, J=12.9, 4.4 Hz, 2H)

Example 6

Synthesis of Compound 56 (1-(3,4-Dichlorobenzyl)-3'-(4-methoxyphenyl)-1'H-spiro[azetidine-3,2'-quinazolin]-4'(3'H)-one)

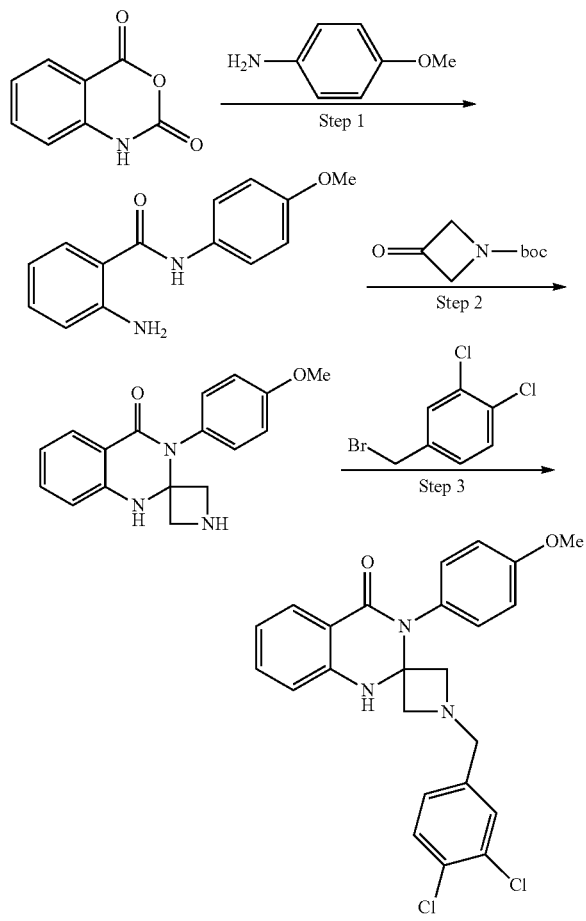

Step 1: Prepared following the same procedure as example 1, step 1. Step 2: A round bottom flask was charged with 2-amino-N-(4-methoxy-phenyl)-benzamide (1.45 g, 6.0 mmol), 3-oxo-azetidine-1-carboxylic acid tert-butyl ester (1.0 g, 6.0 mmol), para-toluene sulphonic acid mono hydrate (1.1 g, 6.0 mmol) and toluene (30 mL). The mixture was heated at 140° C. bath temperature for 1 h which formed a precipitate. The mixture was cooled, filtered, and the precipitate was suspended in ethyl acetate, filtered and dried under vacuum to give the tosylate salt of 3'-(4-methoxyphenyl)-1'H-spiro[azetidine-3,2'-quinazolin]-4'(3'H)-one (2.0 g; 71%); LCMS (ESI) 296 (M+H); $^1$H NMR (400 MHz, METHANOL-$d_4$) δ ppm: 7.81-7.85 (m, 1H), 7.71 (d, J=8.2 Hz, 2H), 7.46-7.51 (m, 1H), 7.30-7.35 (m, 2H), 7.24 (d, J=8.1 Hz, 2H), 7.11-7.15 (m, 2H), 6.97-7.03 (m, 2H), 4.42 (d, J=12.8 Hz, 2H), 4.22 (d, J=12.9 Hz, 2H), 3.87 (s, 3H), 2.37 (s, 3H).

Step 3: A scintillation vial was charged with the tosylate salt of 3'-(4-methoxyphenyl)-1'H-spiro[azetidine-3,2'-quinazolin]-4'(3'H)-one (117 mg, 0.25 mmol), cesium carbonate (243 mg, 0.75 mmol) and dry acetonitrile (2.5 mL). To this mixture was added 4-bromomethyl-1,2-dichloro-benzene (60 mg, 0.25 mmol). The reaction was allowed 3 h at room temperature. It was then diluted with dichloromethane (30 mL), added to saturated NaHCO$_3$ (aq) (30 mL), and extracted with dichloromethane (3×30 mL). The combined organic phase was dried over anhydrous sodium sulfate, filtered and the solvent was evaporated under reduced pressure. The material was purified by chromatography using heptane/ethyl acetate (0-50%) as eluent to give title compound 1-(3,4-dichlorobenzyl)-3'-(4-methoxyphenyl)-1'H-spiro[azetidine-3,2'-quinazolin]-4'(3'H)-one (84 mg; 74%); LCMS (ESI) 454 (M+H); $^1$H NMR (400 MHz, CHLOROFORM-d) δ ppm: 7.94 (d, J=7.6 Hz, 1H), 7.31-7.41 (m, 2H), 7.25 (d, J=1.6 Hz, 1H), 7.14 (d, J=8.8 Hz, 2H), 6.90-7.02 (m, 4H), 6.84 (d, J=8.0 Hz, 1H), 5.32 (br.s., 1H), 3.88 (s, 3H), 3.45 (d, J=8.3 Hz, 2H), 3.41 (s, 2H), 3.18 (d, J=8.5 Hz, 2H).

The following compounds were synthesized in an analogous manner:

Compound 92 (1-Benzyl-3'-(4-methoxyphenyl)-1'H-spiro[azetidine-3,2'-quinazolin]-4'(3'H)-one); LCMS (ESI) 386 (M+H)

Compound 84 (1-(2-Fluorobenzyl)-3'-(4-methoxyphenyl)-1'H-spiro[azetidine-3,2'-quinazolin]-4'(3'H)-one); LCMS (ESI) 404 (M+H)

Compound 93 (1-(3-Fluorobenzyl)-3'-(4-methoxyphenyl)-1'H-spiro[azetidine-3,2'-quinazolin]-4'(3'H)-one); LCMS (ESI) 404 (M+H)

Compound 101 (1-(4-Fluorobenzyl)-3'-(4-methoxyphenyl)-1'H-spiro[azetidine-3,2'-quinazolin]-4'(3'H)-one); LCMS (ESI) 404 (M+H)

Compound 76 (1-(3-Chlorobenzyl)-3'-(4-methoxyphenyl)-1'H-spiro[azetidine-3,2'-quinazolin]-4'(3'H)-one); LCMS (ESI) 420 (M+H)

Compound 112 (1-(4-Ethylbenzyl)-3'-(4-methoxyphenyl)-1'H-spiro[azetidine-3,2'-quinazolin]-4'(3'H)-one); LCMS (ESI) 414 (M+H)

Compound 98 (1-((5-Chlorothiophen-2-yl)methyl)-3'-(4-methoxyphenyl)-1'H-spiro[azetidine-3,2'-quinazolin]-4'(3'H)-one); LCMS (ESI) 426 (M+H)

Compound 94 (3'-(4-Methoxyphenyl)-1-(2-methylbenzyl)-1'H-spiro[azetidine-3,2'-quinazolin]-4'(3'H)-one); LCMS (ESI) 400 (M+H)

Compound 89 (3'-(4-Methoxyphenyl)-1-(3-methylbenzyl)-1'H-spiro[azetidine-3,2'-quinazolin]-4'(3'H)-one); LCMS (ESI) 400 (M+H)

Compound 72 (3'-(4-Methoxyphenyl)-1-(4-methylbenzyl)-1'H-spiro[azetidine-3,2'-quinazolin]-4'(3'H)-one); LCMS (ESI) 400 (M+H)

Compound 81 (3'-(4-Methoxyphenyl)-1-(2-(trifluoromethyl)benzyl)-1'H-spiro[azetidine-3,2'-quinazolin]-4'(3'H)-one); LCMS (ESI) 464 (M+H)

Compound 50 (1-(2-Chlorobenzyl)-3'-(4-methoxyphenyl)-1'H-spiro[azetidine-3,2'-quinazolin]-4'(3'H)-one); LCMS (ESI) 420 (M+H); $^1$H NMR (400 MHz, CHLOROFORM-d) δ ppm: 3.25-3.31 (m, 2H), 3.49-3.55 (m, 2H), 3.59 (s, 2H), 3.87 (s, 3H), 5.43 (br.s., 1H), 6.83 (d, J=8.0 Hz, 1H), 6.92 (td, J=7.6, 0.7 Hz, 1H), 6.95-7.01 (m, 2H), 7.12-7.22 (m, 5H), 7.28-7.33 (m, 1H), 7.33-7.40 (m, 1H) 7.94 (dd, J=7.8, 1.2 Hz, 1H)

Compound 85 (1-(4-Chlorobenzyl)-3'-(4-methoxyphenyl)-1'H-spiro[azetidine-3,2'-quinazolin]-4'(3'H)-one); LCMS (ESI) 420 (M+H)

Compound 86 (3'-(4-Methoxyphenyl)-1-(naphthalen-1-ylmethyl)-1'H-spiro[azetidine-3,2'-quinazolin]-4'(3'H)-one); LCMS (ESI) 436 (M+H)

Compound 90 (3'-(4-Methoxyphenyl)-1-(naphthalen-2-ylmethyl)-1'H-spiro[azetidine-3,2'-quinazolin]-4'(3'H)-one); LCMS (ESI) 436 (M+H)

Compound 95 (1-(2,6-Difluorobenzyl)-3'-(4-methoxyphenyl)-1'H-spiro[azetidine-3,2'-quinazolin]-4'(3'H)-one); LCMS (ESI) 422 (M+H)

Compound 65 (3'-(4-Methoxyphenyl)-1-(2-(trifluoromethoxy)benzyl)-1'H-spiro[azetidine-3,2'-quinazolin]-4'(3'H)-one); LCMS (ESI) 470 (M+H); H NMR (400 MHz, CHLOROFORM-d) δ ppm: 3.21-3.27 (m, 2H), 3.46-3.51 (m, 2H), 3.54 (s, 2H), 3.87 (s, 3H), 5.36 (s, 1H), 6.80-6.84 (m, 1H), 6.89-6.95 (m, 1H), 6.95-7.01 (m, 2H), 7.11-7.24 (m, 4H), 7.25-7.30 (m, 2H), 7.33-7.40 (m, 1H), 7.94 (dd, J=7.81, 1.56 Hz, 1H)

Compound 35 (Methyl 1-benzyl-3'-(4-methoxyphenyl)-4'-oxo-3',4'-dihydro-1'H-spiro[azetidine-3,2'-quinazoline]-7'-carboxylate); LCMS (ESI) 444 (M+H); H NMR (CHLOROFORM-d) δ ppm: 7.99 (d, J=8.0 Hz, 1H), 7.40-7.59 (m, 2H), 7.21-7.29 (m, 3H), 7.07-7.19 (m, 4H), 7.00 (d, J=8.8 Hz, 2H), 5.53 (s, 1H), 3.82-3.98 (m, 6H), 3.36-3.48 (m, 4H), 3.16 (d, J=8.9 Hz, 2H)

Compound 119 (3'-(4-Methoxyphenyl)-1-(2,4,6-trifluorobenzyl)-1'H-spiro[azetidine-3,2'-quinazolin]-4'(3'H)-one); LCMS (ESI) 440 (M+H)

Compound 124 (1-(2-Chlorobenzyl)-7'-fluoro-3'-(4-(2-methoxyethoxyl)phenyl)-1'H-spiro[azetidine-3,2'-quinazolin]-4'(3'H)-one); LCMS (ESI) 482 (M+H); $^1$H NMR (400 MHz, DMSO-$d_6$) δ ppm: 8.02 (s, 1H), 7.70 (t, J=7.5 Hz, 1H), 7.39-7.31 (m, 1H), 7.28-7.18 (m, 4H), 7.18-7.11 (m, 1H), 7.02 (d, J=8.3 Hz, 2H), 6.68 (d, J=10.6 Hz, 1H), 6.59 (t, J=8.7 Hz, 1H), 4.19-4.12 (m, 2H), 3.73-3.67 (m, 2H), 3.54 (s, 2H), 3.45 (d, J=8.2 Hz, 2H), 3.39 (d, J=8.3 Hz, 2H), 3.33 (s, 3H)

Compound 123 (1-(4-Chlorobenzyl)-7'-fluoro-3'-(4-(2-methoxyethoxyl)phenyl)-1'H-spiro[azetidine-3,2'-quinazolin]-4'(3'H)-one); LCMS (ESI) 482 (M+H); H NMR (400 MHz, DMSO-$d_6$) δ ppm: 8.02 (s, 1H), 7.69 (dd, J=8.6, 6.5 Hz, 1H), 7.29 (d, J=8.4 Hz, 2H), 7.18 (d, J=8.8 Hz, 2H), 7.11 (d, J=8.3 Hz, 2H), 7.02 (d, J=8.8 Hz, 2H), 6.69 (dd, J=10.7, 2.4 Hz, 1H), 6.58 (td, J=8.7, 2.4 Hz, 1H), 4.20-4.12 (m, 2H), 3.74-3.66 (m, 2H), 3.42 (s, 2H), 3.34 (s, 3H), 3.32 (s, 4H)

Example 7

Synthesis of Compound 26 (7'-Bromo-3'-(4-chlorophenyl)-1-(1-phenylethyl)-1'H-spiro[piperidine-4,2'-quinazolin]-4'(3'H)-one)

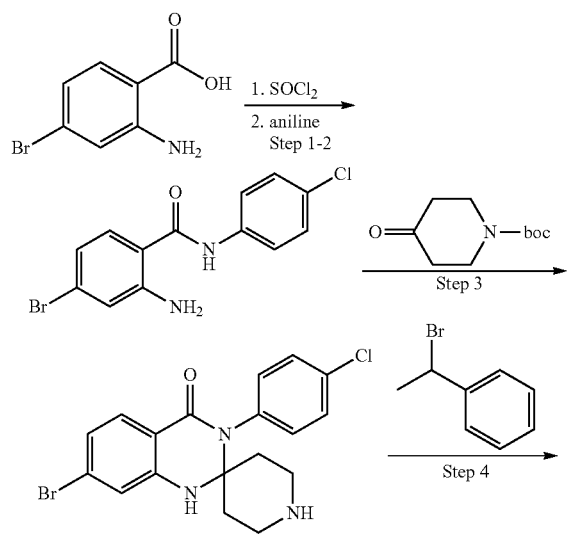

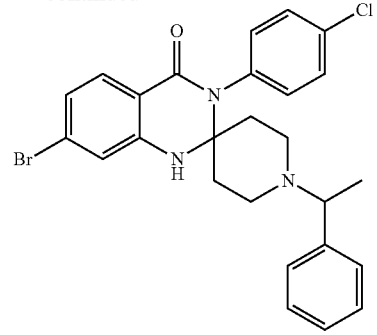

Step 1-2: A round bottom flask was charged with the 2-amino-4-bromo-benzoic acid (864 mg, 4.0 mmol), thionyl chloride (10 mL) and catalytic dimethyl formamide (1 drop). The reaction was heated at 80° C. for 1 h, cooled and the solvent was evaporated under reduced pressure. The resulting oil was dissolved in dichloromethane (5 mL). A separate round bottom flask equipped was charged with pyridine (948 mg, 12 mmol), 4-chloro-phenylamine (508 mg, 4.0 mmol) and dichloromethane and was cooled to 0° C. To this mixture, the acyl chloride was added dropwise and the reaction allowed to warm to room temperature over 1 h. It was added to saturated NaHCO$_3$ (aq) (50 mL), extracted with dichloromethane (3×50 mL), dried over anhydrous sodium sulfate, filtered and the solvent was evaporated under reduced pressure. The material was purified by chromatography using heptane/ethyl acetate (0-50%) as eluent to give 2-amino-4-bromo-N-(4-chloro-phenyl)-benzamide (910 mg; 70%) as a white solid; LCMS (ESI) 325 (M+H); $^1$H NMR (400 MHz, CHLOROFORM-d) δ ppm: 7.66 (br.s., 1H), 7.52 (d, J=8.8 Hz, 2H), 7.32-7.37 (m, 1H), 7.31 (d, J=8.4 Hz, 1H), 6.90 (d, J=1.8 Hz, 1H), 6.83 (dd, J=8.4, 1.8 Hz, 1H), 5.62 (brs, 1H).

Step 3: A round bottom flask was charged with 2-amino-4-bromo-N-(4-chloro-phenyl)-benzamide (650 mg, 2.0 mmol), 4-oxo-piperidine-1-carboxylic acid tert-butyl ester (398 mg, 2.0 mmol), para-toluene sulphonic acid mono hydrate (380 mg, 2.0 mmol) and toluene (20 mL). The mixture was heated at 140° C. for 1 h which formed a precipitate. The mixture was cooled, filtered, and the precipitate was suspended in ethyl acetate, filtered and dried under vacuum to give 7'-bromo-3'-(4-chlorophenyl)-1'H-spiro[piperidine-4,2'-quinazolin]-4'(3'H)-one tosylate salt (1.0 g; 85%) as a white solid; LCMS (ESI) 406 (M+H).

Step 4: A scintillation vial was charged with 7'-bromo-3'-(4-chlorophenyl)-1'H-spiro[piperidine-4,2'-quinazolin]-4'(3'H)-one tosylate salt (116 mg, 0.2 mmol), cesium carbonate (195 mg, 0.6 mmol) and dry acetonitrile (4 mL). To this mixture was added (1-bromo-ethyl)-benzene (93 mg, 0.4 mmol). The reaction was heated at 50° C. for 2 h then diluted with dichloromethane (30 mL), added to saturated NaHCO$_3$ (aq) (30 mL), and extracted with dichloromethane (3×30 mL). The combined organic phase was dried over anhydrous sodium sulfate and the solvent was evaporated under reduced pressure. The material was purified by chromatography using heptane/ethyl acetate (0-40%) as eluent to give title compound 7'-bromo-3'-(4-chlorophenyl)-1-(1-phenylethyl)-1'H-spiro[piperidine-4,2'-quinazolin]-4'(3'H)-one as a white solid (77 mg; 76%); LCMS (ESI) 511 (M+H); $^1$H NMR (400 MHz, CHLOROFORM-d) δ ppm: 7.77 (d, J=8.3 Hz, 1H), 7.67 (brs, 2H), 7.52 (br.s., 1H), 7.43 (br.s., 3H), 7.31 (d, J=6.7 Hz, 2H), 7.19 (d, J=7.5 Hz, 1H), 7.05-7.14 (m, 2H), 6.19 (br.s., 1H), 4.52 (br.s., 1H), 3.69 (br.s., 2H), 3.53

(br.s., 1H), 3.03 (br.s., 1H), 2.86 (br.s., 1H), 2.48 (br.s., 1H), 2.34 (d, J=13.4 Hz, 1H), 2.15 (d, J=15.3 Hz, 1H), 1.89 (d, J=6.0 Hz, 3H).

The following compounds were synthesized in an analogous manner:

Compound 52 (7'-Bromo-1-(3,4-difluorobenzyl)-3'-(4-(trifluoromethyl)phenyl)-1'H-spiro[piperidine-4,2'-quinazolin]-4'(3'H)-one); LCMS (ESI) 566 (M+H); $^1$H NMR (400 MHz, CHLOROFORM-d) δ ppm: 7.82 (d, J=8.4 Hz, 1H), 7.74 (d, J=8.3 Hz, 2H), 7.36 (d, J=8.1 Hz, 2H), 7.03-7.15 (m, 3H), 7.01 (d, J=1.6 Hz, 1H), 6.95 (br.s., 1H), 4.74 (s, 1H), 3.43 (s, 2H), 2.77 (d, J=12.0 Hz, 2H), 1.93-2.31 (m, 4H), 1.67-1.87 (m, 2H)

Compound 7 (7'-Bromo-3'-(4-chlorophenyl)-1-(1-(3,4-difluorophenyl)ethyl)-1'H-spiro[piperidine-4,2'-quinazolin]-4'(3'H)-one); LCMS (ESI) 546 (M+H); $^1$H NMR (400 MHz, CHLOROFORM-d) δ ppm: 7.80 (d, J=8.3 Hz, 1H), 7.41-7.48 (m, 2H), 7.00-7.20 (m, 5H), 6.95 (d, J=1.6 Hz, 2H), 4.67 (s, 1H), 3.34 (q, J=6.6 Hz, 1H), 2.95 (d, J=11.8 Hz, 1H), 2.64 (d, J=12.3 Hz, 1H), 1.93-2.16 (m, 4H), 1.80 (td, J=13.1, 4.4 Hz, 1H), 1.69 (td, J=12.9, 4.4 Hz, 1H), 1.28 (d, J=6.7 Hz, 3H)

Compound 23 (1-(3,4-Difluorobenzyl)-7'-fluoro-3'-(4-methoxyphenyl)-1'H-spiro[piperidine-4,2'-quinazolin]-4'(3'H)-one); LCMS (ESI) 468 (M+H); H NMR (400 MHz, CHLOROFORM-d) δ ppm: 1.78-1.89 (m, 2H), 2.06 (d, J=11.6 Hz, 2H), 2.14 (t, J=11.7 Hz, 2H), 2.71-2.80 (m, 2H), 3.42 (s, 2H), 3.85 (s, 3H), 4.78 (s, 1H), 6.47 (dd, J=9.8, 2.3 Hz, 1H), 6.59 (td, J=8.7, 2.1 Hz, 1H), 6.92-6.99 (m, 3H), 7.03-7.11 (m, 2H), 7.11-7.16 (m, 2H), 7.97 (dd, J=8.6, 6.4 Hz, 1H)

Compound 64 (3'-(4-Chlorophenyl)-1-(3,4-difluorobenzyl)-7'-fluoro-1'H-spiro[piperidine-4,2'-quinazolin]-4'(3'H)-one); LCMS (ESI) 472 (M+H); $^1$H NMR (400 MHz, (400 MHz, CHLOROFORM-d) δ ppm: 1.57 (td, J=12.8, 4.2 Hz, 2H), 1.97 (d, J=12.7 Hz, 2H), 2.34 (t, J=11.6 Hz, 2H), 2.59 (d, J=11.7 Hz, 2H), 3.43 (s, 2H), 6.55 (td, J=8.7, 2.5 Hz, 1H), 6.81 (dd, J=11.0, 2.5 Hz, 1H), 7.08 (d, J=4.3 Hz, 1H), 7.21-7.37 (m, 5H), 7.47-7.54 (m, 2H), 7.70 (dd, J=8.7, 6.7 Hz, 1H)

Compound 69 (1-(3,4-Difluorobenzyl)-7'-fluoro-3'-(4-(trifluoromethoxy)phenyl)-1'H-spiro[piperidine-4,2'-quinazolin]-4'(3'H)-one); LCMS (ESI) 522 (M+H); $^1$H NMR (400 MHz, CHLOROFORM-d) δ ppm: 7.96 (dd, J=8.6, 6.4 Hz, 1H), 7.24-7.33 (m, 6H), 7.04-7.13 (m, 2H), 6.96 (d, J=4.0 Hz, 1H), 6.59-6.65 (m, 1H), 6.49 (dd, J=9.7, 2.2 Hz, 1H), 4.78 (s, 1H), 3.44 (s, 2H), 2.78 (d, J=12.0 Hz, 2H), 2.05-2.20 (m, 3H), 1.80 (td, J=12.8, 4.4 Hz, 2H)

Compound 61 (7'-Bromo-3'-(4-chlorophenyl)-1-(1-phenylpropyl)-1'H-spiro[piperidine-4,2'-quinazolin]-4'(3'H)-one); LCMS (ESI) 524 (M+H); $^1$H NMR (400 MHz, CHLOROFORM-d) δ ppm: 7.78 (d, J=8.3 Hz, 1H), 7.42 (dt, J=5.7, 2.7 Hz, 2H), 7.32 (q, J=6.7 Hz, 3H), 7.11-7.19 (m, 4H), 6.99 (dd, J=8.3, 1.3 Hz, 1H), 6.84-6.87 (m, 1H), 4.63 (s, 1H), 3.17 (dd, J=9.0, 5.1 Hz, 1H), 2.95 (d, J=12.1 Hz, 1H), 2.72 (d, J=11.5 Hz, 1H), 2.03-2.14 (m, 2H), 1.78-1.99 (m, 4H), 1.63-1.73 (m, 2H), 0.70 (t, J=7.3 Hz, 3H)

Compound 33 (7'-Bromo-3'-(4-chlorophenyl)-1-(1-(3,4-difluorophenyl)propyl)-1'H-spiro[piperidine-4,2'-quinazolin]-4'(3'H)-one); LCMS (ESI) 560 (M+H); $^1$H NMR (400 MHz, CHLOROFORM-d) δ ppm: 7.79 (d, J=8.3 Hz, 1H), 7.41-7.47 (m, 2H), 7.07-7.19 (m, 3H), 6.97-7.04 (m, 2H), 6.91 (d, J=1.6 Hz, 2H), 4.60 (s, 1H), 3.12 (dd, J=8.9, 4.8 Hz, 1H), 2.95 (d, J=11.8 Hz, 1H), 2.66 (d, J=12.1 Hz, 1H), 2.04-2.14 (m, 2H), 1.77-2.00 (m, 4H), 1.57-1.72 (m, 2H), 0.69 (t, J=7.3 Hz, 3H)

Example 8

Synthesis of Compound 16 (1-(3,4-Difluorobenzyl)-3'-(4-(trifluoromethoxy)phenyl)-7'-(trifluoromethyl)-1'H-spiro[piperidine-4,2'-quinazolin]-4'(3'H)-one)

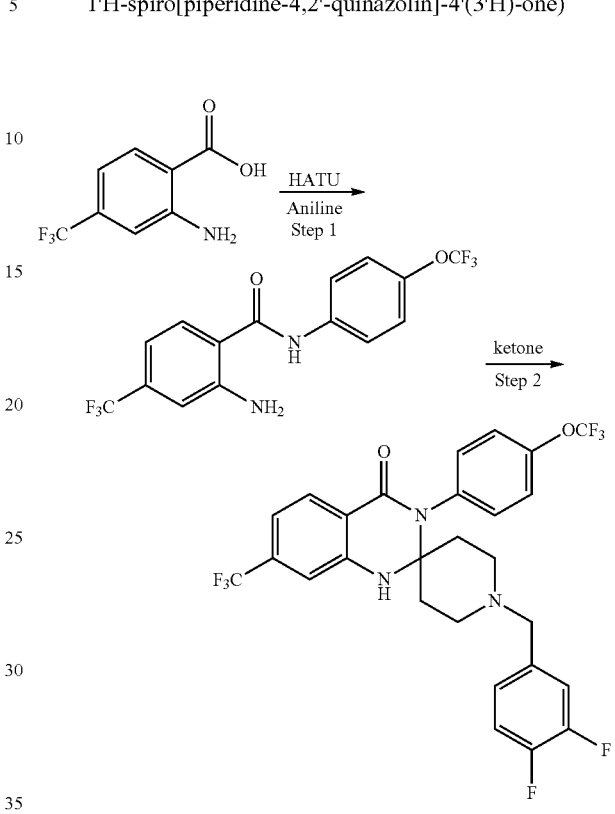

Step 1: A scintillation vial was charged 2-amino-4-trifluoromethyl-benzoic acid (410 mg, 2.0 mmol), 4-trifluoromethoxy-phenylamine (531 mg, 3.0 mmol), diisopropylethylamine (1.0 mL, 6.0 mmol) and dry dimethyl formamide (10 mL). To this mixture was added HATU (760 mg, 2.0 mmol) and the reaction was stirred at room temperature overnight. The reaction mixture was poured into water and the precipitate was filtered, washed with water and dried under vacuum to give 2-amino-N-(4-trifluoromethoxy-phenyl)-4-trifluoromethyl-benzamide (65 mg; 90%) as a white solid; LCMS (ESI) 365 (M+H); $^1$H NMR (CHLOROFORM-d) δ: 7.77 (br.s., 1H), 7.62 (d, J=8.9 Hz, 1H), 7.57 (d, J=8.2 Hz, 1H), 7.24 (s, 2H), 6.92-7.00 (m, 1H), 5.70 (br.s., 1H).

Step 2: A round bottom flask was charged with 2-amino-N-(4-trifluoromethoxy-phenyl)-4-trifluoromethyl-benzamide (110 mg, 0.3 mmol), 1-(3,4-Difluoro-benzyl)-piperidin-4-one (68 mg, 0.3 mmol), para-toluene sulphonic acid mono hydrate (6 mg, 0.03 mmol) and toluene (10 mL). The reaction mixture was heated at 140° C. bath temperature for 4 h. The reaction was cooled, diluted with ethyl acetate, added to sat. $Na_2CO_3$ (aq), the phases were separated and the aqueous phase was extracted with ethyl acetate dried over anhydrous sodium sulfate, filtered and the solvent was evaporated under reduced pressure. The material was purified by chromatography using heptane/ethyl acetate as eluent to give title compound 1-(3,4-difluorobenzyl)-3'-(4-(trifluoromethoxy)phenyl)-7'-(trifluoromethyl)-1'H-spiro[piperidine-4,2'-quinazolin]-4'(3'H)-one (140 mg; 82%) as a white solid; LCMS (ESI) 572 (M+H); $^1$H NMR (400 MHz, CHLOROFORM-d) δ ppm: 8.07 (d, J=8.1 Hz, 1H), 7.30-

7.35 (m, 2H), 7.25-7.29 (m, 3H), 7.03-7.18 (m, 4H), 6.92-6.98 (m, 1H), 4.87 (s, 1H), 3.44 (s, 2H), 2.79 (d, J=12.2 Hz, 2H), 2.17 (t, J=11.7 Hz, 2H), 2.08 (d, J=12.0 Hz, 2H), 1.82 (td, J=12.8, 4.4 Hz, 2H).

Example 9

Synthesis of Compound 60 (1(-(3,4-Difluorobenzyl)-3'-(4-methoxyphenyl)-7'-methyl-1'H-spiro[piperidine-4,2'-quinazolin]-4'(3'H)-one)

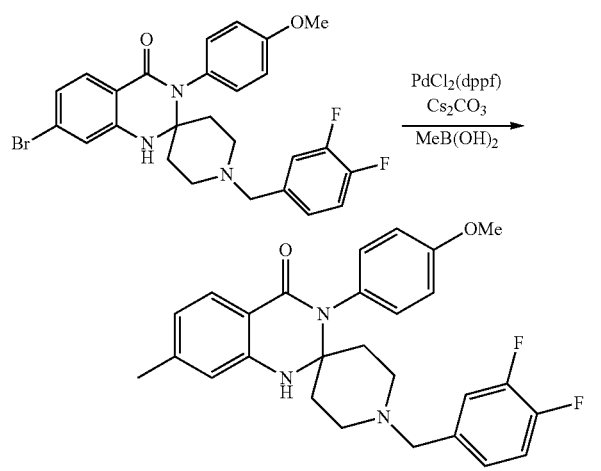

7'-bromo-1-(3,4-difluorobenzyl)-3'-(4-methoxyphenyl)-1'H-spiro[piperidine-4,2'-quinazolin]-4'(3'H)-one, compound 17, (50 mg, 0.094 mmol) and methylboronic acid (11 mg, 0.189 mmol) were taken in sealed tube. Dioxane (3 mL) and water (0.5 mL) were added to the reaction mixture, followed by Pd(dppf)Cl$_2$ (4 mg, 0.004 mmol) and cesium carbonate (92 mg, 0.283 mmol). The reaction mixture was heated at 70° C. for 20 h. The reaction was cooled to room temperature, diluted with water (5 mL), brine (5 mL) and ethyl acetate (50 mL). The organic layer was separated and aqueous layer was extracted with ethyl acetate (50 mL). The combined organic phase was dried over anhydrous sodium sulfate, filtered and concentrated under reduced pressure. The residue was purified by chromatography using ethyl acetate/dichloromethane (0%-80%) as eluent to give title compound 1-(3,4-difluorobenzyl)-3'-(4-methoxyphenyl)-7'-methyl-1'H-spiro[piperidine-4,2'-quinazolin]-4'(3'H)-one (31 mg; 71%) as a white solid; LCMS (ESI) 464 (M+H); $^1$H NMR (400 MHz, CHLOROFORM-d) δ ppm: 1.76-1.89 (m, 2H), 2.00-2.22 (m, 4H), 2.34 (s, 3H), 2.67-2.79 (m, 2H), 3.42 (s, 2H), 3.85 (s, 3H), 4.59 (s, 1H), 6.60 (s, 1H), 6.73 (d, J=7.9 Hz, 1H), 6.91-7.00 (m, 3H), 7.02-7.19 (m, 4H), 7.85 (d, J=7.9 Hz, 1H).

The following compounds were synthesized in an analogous manner:

Compound 63 (1-(3,4-Difluorobenzyl)-7'-ethyl-3'-(4-methoxyphenyl)-1'H-spiro[piperidine-4,2'-quinazolin]-4'(3'H)-one); LCMS (ESI) 478 (M+H); $^1$H NMR (400 MHz, CHLOROFORM-d) δ ppm: 1.26 (t, J=7.6 Hz, 3H), 1.76-1.89 (m, 2H), 2.02-2.21 (m, 4H), 2.64 (q, J=7.6 Hz, 2H), 2.69-2.78 (m, 2H), 3.42 (s, 2H), 3.85 (s, 3H), 4.60 (s, 1H), 6.62 (d, J=0.9 Hz, 1H), 6.76 (dd, J=8.0, 1.4 Hz, 1H), 6.92-7.00 (m, 3H), 7.01-7.19 (m, 4H), 7.88 (d, J=8.0 Hz, 1H)

Compound 19 (1-(3,4-Difluorobenzyl)-3'-(4-methoxyphenyl)-7'-phenyl-1'H-spiro[piperidine-4,2'-quinazolin]-4'(3'H)-one); LCMS (ESI) 526 (M+H); $^1$H NMR (400 MHz, CHLOROFORM-d) δ ppm: 1.86 (td, J=12.8, 4.3 Hz, 2H), 2.06-2.23 (m, 4H), 2.76 (dt, J=11.9, 2.1 Hz, 2H), 3.86 (s, 3H), 3.43 (s, 2H), 4.73 (s, 1H), 6.92-7.02 (m, 4H), 7.03-7.13 (m, 2H), 7.13-7.19 (m, 3H), 7.37-7.43 (m, 1H), 7.44-7.50 (m, 2H), 7.59-7.65 (m, 2H), 8.03 (d, J=8.1 Hz, 1H)

Example 10

Synthesis of Compound 121 (1-(3,4-Difluorobenzyl)-7'-(2-methoxyethoxy)-3'-(4-(trifluoromethoxy)phenyl)-1'H-spiro[piperidine-4,2'-quinazolin]-4'(3'H)-one)

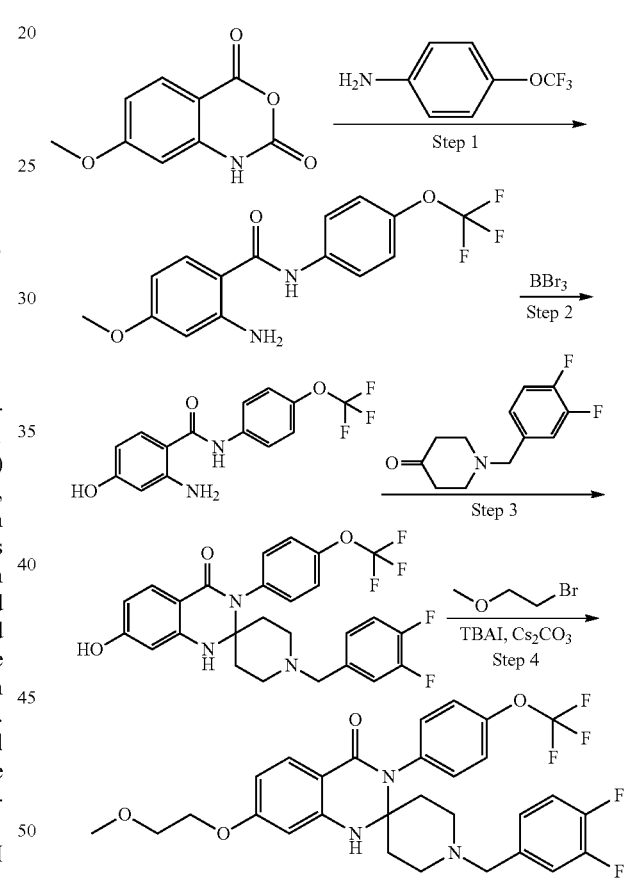

Step 1: Prepared following the same procedure as example 1 step 1 to give 2-amino-4-hydroxy-N-(4-trifluoromethoxy-phenyl)-benzamide (79 mg; 66%); H NMR (400 MHz, DMSO-d$_6$) δ ppm: 9.85 (s, 1H), 9.65 (s, 1H), 7.75-7.81 (m, 2H), 7.54 (d, J=8.8 Hz, 1H), 7.30 (d, J=8.3 Hz, 2H), 6.49 (s, 2H), 6.12 (d, J=2.4 Hz, 1H), 6.03 (dd, J=8.7, 2.4 Hz, 1H); $^{19}$F NMR (376 MHz, DMSO-d$_6$) δ ppm: −57.45 (br.s., 3 F).

Step 2: To a scintillation vial was added 2-amino-4-methoxy-N-(4-trifluoromethoxy-phenyl)-benzamide (0.13 g, 0.39 mmol) and dry dichloromethane (3 mL). The reaction vial was cooled to 0° C. after which a solution of boron tribromide (1.16 mL, 1.16 mmol) was added drop-wise slowly. The reaction was allowed to warm to room temperature over 96 h. The reaction was then re-cooled to 0° C. and quenched with 10 mL of saturated aqueous sodium bicarbonate solution. The resulting mixture was extracted with ethyl acetate. The combined organic phase was washed with water and brine, dried over anhydrous sodium sulfate, filtered and evaporated in vacuo. The residue was purified by chromatography using heptanes/ethyl acetate (0%-50%) as eluent to give 2-amino-4-hydroxy-N-(4-trifluoromethoxyphenyl)-benzamide (79 mg; 66%) as a beige solid; $^1$H NMR (400 MHz, DMSO-$d_6$) δ ppm: 9.85 (s, 1H), 9.65 (s, 1H), 7.75-7.81 (m, 2H), 7.54 (d, J=8.8 Hz, 1H), 7.30 (d, J=8.3 Hz, 2H), 6.49 (s, 2H), 6.12 (d, J=2.4 Hz, 1H), 6.03 (dd, J=8.7, 2.4 Hz, 1H); $^{19}$F NMR (376 MHz, DMSO-$d_6$) δ ppm: −57.44 (br.s., 3 F).

Step 3: Prepared following the same procedure as example 4 step 3 to give 1-(3,4-difluorobenzyl)-7'-hydroxy-3'-(4-(trifluoromethoxy)phenyl)-1'H-spiro[piperidine-4,2'-quinazolin]-4'(3'H)-one (47 mg; 36%); LCMS (ESI) 520 (M+H); $^1$H NMR (400 MHz, DMSO-$d_6$) δ ppm: 9.88 (s, 1H), 7.48 (d, J=8.5 Hz, 1H), 7.42 (d, J=8.1 Hz, 2H), 7.21-7.36 (m, 4H), 7.03-7.09 (m, 1H), 6.84 (s, 1H), 6.40 (d, J=2.2 Hz, 1H), 6.19 (dd, J=8.5, 2.2 Hz, 1H), 3.42 (s, 2H), 2.53-2.60 (m, 2H), 2.31-2.41 (m, 2H), 1.96 (d, J=12.4 Hz, 2H), 1.47-1.58 (m, 2H); $^{19}$F NMR (376 MHz, DMSO-$d_6$) δ ppm: −141.93--141.70 (m, 1F) −139.76--139.53 (m, 1F) −57.18 (br.s., 3 F).

Step 4: A round bottom flask was charged with 1-(3,4-difluorobenzyl)-7'-hydroxy-3'-(4-(trifluoromethoxy)phenyl)-1'H-spiro[piperidine-4,2'-quinazolin]-4'(3'H)-one (21 mg, 0.04 mmol) and dry dimethyl formamide (3 mL). 1-Bromo-2-methoxy-ethane (4.8 μL, 6.8 mg, 0.05 mmol) was added, followed by tetrabutylammonium iodide (18.1 mg, 0.05 mmol) and cesium carbonate (53 mg, 0.16 mmol) and the reaction mixture was heated at 60° C. for 16 h. The reaction was cooled to room temperature, diluted with water (10 mL) and ethyl acetate (10 mL). The organic layer was separated, washed with water and brined, dried over anhydrous sodium sulfate, filtered and concentrated in vacuo. The residue was purified by chromatography using ethyl acetate/dichloromethane as eluent to give title compound 1-(3,4-difluorobenzyl)-7'-(2-methoxyethoxy)-3'-(4-(trifluoromethoxy)phenyl)-1'H-spiro[piperidine-4,2'-quinazolin]-4'(3'H)-one (13 mg; 56%) as a light yellow solid; LCMS (ESI) 578 (M+H); $^1$H NMR (400 MHz, DMSO-$d_6$) δ ppm: 7.56 (d, J=8.6 Hz, 1H), 7.41-7.46 (m, 2H), 7.30-7.36 (m, 3H), 7.21-7.30 (m, 1H), 7.03-7.09 (m, 1H), 6.97 (s, 1H), 6.58 (d, J=2.4 Hz, 1H), 6.35 (dd, J=8.7, 2.4 Hz, 1H), 4.07-4.12 (m, 2H), 3.65-3.69 (m, 2H), 3.42 (s, 2H), 3.32 (s, 3H), 2.55-2.61 (m, 2H), 2.31-2.40 (m, 2H), 1.98 (d, J=12.1 Hz, 2H), 1.49-1.59 (m, 2H); $^{19}$F NMR (376 MHz, DMSO-$d_6$) δ ppm: −141.97--141.69 (m, 1F) −139.81--139.50 (m, 1F) −57.18 (br.s., 3F).

Example 11

Synthesis of Compound 83 (1-(3,4-Difluorobenzyl)-3'-(4-methoxyphenyl)-7'-(piperidin-1-yl)-1'H-spiro[piperidine-4,2'-quinazolin]-4'(3'H)-one)

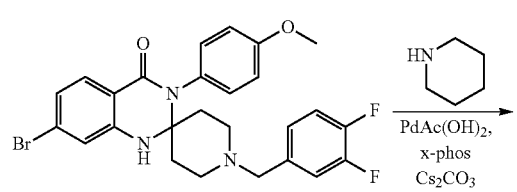

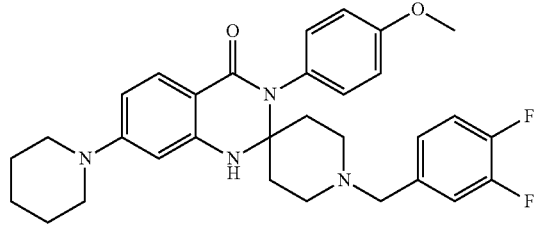

A sealed tube was charged with 7'-bromo-1-(3,4-difluorobenzyl)-3'-(4-methoxyphenyl)-1'H-spiro[piperidine-4,2'-quinazolin]-4'(3'H)-one, compound 17, (50 mg, 0.09 mmol), piperidine (14 μL, 0.14 mmol), dicyclohexyl-(2',4',6'-triisopropyl-biphenyl-2-yl)-phosphane (14 mg, 0.03 mmol), cesium carbonate (93 mg, 0.28 mmol) and then dioxane was added to the reaction mixture. Nitrogen gas was bubbled through the reaction mixture for 2 min, and palladium(II) acetate (4.3 mg, 0.02 mmol) was added. The reaction mixture was further degassed with nitrogen for 2 min before the tube was sealed and the reaction mixture was heated at 90° C. for 6 h. The reaction mixture was cooled, diluted with water, brine and ethyl acetate. The organic layer was separated and the aqueous layer was reextracted with ethyl acetate. The combined organic phase was dried over anhydrous sodium sulfate, filtered and evaporated in vacuo. The residue was purified by chromatography using ethyl acetate/dichloromethane (0%-80%) as eluent to give title compound 1-(3,4-difluorobenzyl)-3'-(4-methoxyphenyl)-7'-(piperidin-1-yl)-1'H-spiro[piperidine-4,2'-quinazolin]-4'(3'H)-one as pale yellow solid (25 mg; 50%); LCMS (ESI) 533 (M+H).

The following compound was synthesized in an analogous manner:

Compound 21 (1-(3,4-Difluorobenzyl)-7'-morpholino-3'-(4-(trifluoromethoxy)phenyl)-1'H-spiro[piperidine-4,2'-quinazolin]-4'(3'H)-one); LCMS (ESI) 589 (M+H); $^1$H NMR (400 MHz, DMSO-$d_6$) δ ppm: 7.49 (d, J=8.8 Hz, 1H), 7.42 (d, J=8.2 Hz, 2H), 7.21-7.36 (m, 4H), 7.06 (ddd, J=6.5, 4.3, 2.2 Hz, 1H), 6.76 (s, 1H), 6.49 (d, J=2.2 Hz, 1H), 6.42 (dd, J=8.8, 2.3 Hz, 1H), 3.71-3.76 (m, 4H), 3.42 (s, 2H), 3.16-3.22 (m, 4H), 2.57 (d, J=12.1 Hz, 2H), 2.31-2.40 (m, 2H), 1.97 (d, J=11.9 Hz, 2H), 1.47-1.58 (m, 2H); $^{19}$F NMR (376 MHz, DMSO-$d_6$) δ ppm: −141.90--141.66 (m, 1F) −139.73--139.51 (m, 1F) −57.18 (br.s., 3F)

Example 12

Synthesis of Compound 40 (1-(3,4-Difluorobenzyl)-3'-(4-methoxyphenyl)-7'-(pyridin-3-yl)-1'H-spiro[piperidine-4,2'-quinazolin]-4'(3'H)-one)

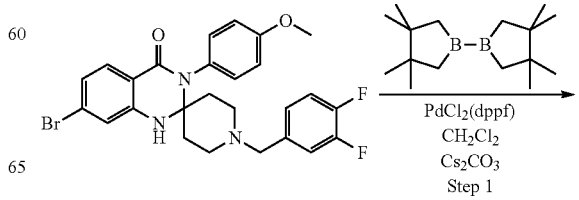

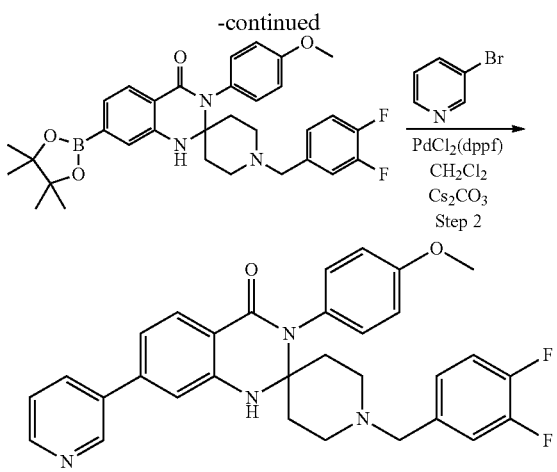

Step 1: A scintillation vial was charged with 7'-bromo-1-(3,4-difluorobenzyl)-3'-(4-methoxyphenyl)-1'H-spiro[piperidine-4,2'-quinazolin]-4'(3'H)-one, compound 17, (264 mg, 0.50 mmol), 4,4,5,5,4',4',5',5'-octamethyl-[2,2']bi[[1,3,2]dioxaborolanyl](127 mg, 0.50 mmol), potassium acetate (245 mg, 2.50 mmol) and dioxane (10 mL). The mixture was degassed with nitrogen and then PdCl$_2$(dppf).CH$_2$Cl$_2$ (41 mg, 0.05 mmol) was added and the mixture was further degassed and then heated at 90° C. for 18 h. The solvent was evaporated and the residue dissolved in DCM and water. The aqueous phase was extracted with DCM, dried over anhydrous sodium sulfate, filtered and evaporated in vacuo. The residue was purified by chromatography using heptane/ethyl acetate (0%-100%) as eluent to give 1-(3,4-difluorobenzyl)-3'-(4-methoxyphenyl)-7'-(4,4,5,5-tetramethyl-1,3,2-dioxaborolan-2-yl)-1'H-spiro[piperidine-4,2'-quinazolin]-4'(3'H)-one (189 mg; 66%); LCMS (ESI) 576 (M+H); $^1$H NMR (400 MHz, CHLOROFORM-d) δ ppm: 7.95 (d, J=7.7 Hz, 1H), 7.34 (d, J=7.7 Hz, 1H), 7.23 (s, 1H), 7.15 (d, J=8.7 Hz, 2H), 7.02-7.12 (m, 2H), 6.96 (d, J=8.7 Hz, 3H), 4.64 (s, 1H), 3.85 (s, 3H), 3.40 (s, 2H), 2.72 (d, J=12.5 Hz, 2H), 2.01-2.17 (m, 4H), 1.77-1.87 (m, 2H), 1.37 (s, 11H).

Step 2: A scintillation vial was charged with 1-(3,4-difluorobenzyl)-3'-(4-methoxyphenyl)-7'-(4,4,5,5-tetramethyl-1,3,2-dioxaborolan-2-yl)-1'H-spiro[piperidine-4,2'-quinazolin]-4'(3'H)-one (29 mg, 0.05 mmol), 3-bromopyridine (16 mg, 0.10 mmol), PdCl$_2$(dppf).CH$_2$Cl$_2$ (4 mg, 0.01 mmol) cesium carbonate (49 mg, 0.15 mmol), water (1 mL) and dioxane (3 mL). The reaction mixture was degassed with nitrogen for 10 min and heated at 80° C. for 30 min. The reaction mixture was cooled, concentrated under reduced pressure and the residue was dissolved in DCM and water. The phases were separated and the aqeuous was further extracted with DCM. The combined organic phase was dried over anhydrous sodium sulfate, filtered and evaporated in vacuo. The residue was purified by chromatography using dichloromethane/dichloromethane/methanol/ammonia (95:4.5:0.5) (0%-50%) as eluent to give title compound 1-(3,4-difluorobenzyl)-3'-(4-methoxyphenyl)-7'-(pyridin-3-yl)-1'H-spiro[piperidine-4,2'-quinazolin]-4'(3'H)-one (20 mg; 76%); LCMS (ESI) 527 (M+H); $^1$H NMR (400 MHz, CHLOROFORM-d) δ ppm: 8.88 (d, J=1.7 Hz, 1H), 8.08 (d, J=8.0 Hz, 1H), 7.90 (dd, J=8.0, 1.8 Hz, 1H), 7.40 (dd, J=7.8, 4.9 Hz, 1H), 7.17 (d, J=8.8 Hz, 2H), 7.02-7.14 (m, 3H), 6.92-7.01 (m, 4H), 4.81 (s, 1H), 3.86 (s, 3H), 3.43 (s, 2H), 2.77 (d, J=11.9 Hz, 2H), 2.19 (t, J=12.2 Hz, 2H), 2.10 (d, J=12.3 Hz, 2H), 1.82-1.93 (m, 2H).

The following compounds were synthesized in an analogous manner:

Compound 73 (1-(3,4-Difluorobenzyl)-3'-(4-methoxyphenyl)-7'-(pyridin-2-yl)-1'H-spiro[piperidine-4,2'-quinazolin]-4'(3'H)-one)

Compound 20 (1-(3,4-Difluorobenzyl)-3'-(4-methoxyphenyl)-7'-(pyridin-4-yl)-1'H-spiro[piperidine-4,2'-quinazolin]-4'(3'H)-one); LCMS (ESI) 527 (M+H); $^1$H NMR (400 MHz, CHLOROFORM-d) δ ppm: 8.70 (d, J=6.0 Hz, 2H), 8.08 (d, J=8.1 Hz, 1H), 7.52 (d, J=6.0 Hz, 2H), 7.14-7.19 (m, 3H), 7.02-7.13 (m, 3H), 6.92-7.01 (m, 3H), 4.80 (s, 1H), 3.86 (s, 3H), 3.43 (s, 2H), 2.77 (d, J=11.9 Hz, 2H), 2.18 (t, J=12.3 Hz, 2H), 2.10 (d, J=12.5 Hz, 2H), 1.87 (td, J=12.8, 4.3 Hz, 2H)

Compound 11 (1-(3,4-Difluorobenzyl)-7'-(furan-2-yl)-3'-(4-methoxyphenyl)-1'H-spiro[piperidine-4,2'-quinazolin]-4'(3'H)-one); LCMS (ESI) 516 (M+H); $^1$H NMR (400 MHz, CHLOROFORM-d) δ ppm: 7.97 (d, J=8.2 Hz, 1H), 7.51 (d, J=1.3 Hz, 1H), 7.21 (dd, J=8.2, 1.4 Hz, 1H), 7.11-7.18 (m, 3H), 7.03-7.11 (m, 2H), 6.97 (d, J=8.8 Hz, 3H), 6.76 (d, J=3.3 Hz, 1H), 6.52 (dd, J=3.3, 1.8 Hz, 1H), 4.73 (s, 1H), 3.85 (s, 3H), 3.43 (s, 2H), 2.75 (d, J=12.0 Hz, 2H), 2.18 (t, J=11.7 Hz, 2H), 2.08 (d, J=12.1 Hz, 2H), 1.84 (td, J=12.8, 4.2 Hz, 2H)

Compound 6 (1-(3,4-Difluorobenzyl)-7'-(furan-2-yl)-3'-(4-(trifluoromethoxy)phenyl)-1'H-spiro[piperidine-4,2'-quinazolin]-4'(3'H)-one); LCMS (ESI) 570 (M+H); $^1$H NMR (400 MHz, CHLOROFORM-d) δ ppm: 1.77 (d, J=4.3 Hz, 2H), 2.10 (d, J=11.6 Hz, 2H), 2.20 (s, 2H), 2.74 (d, J=12.0 Hz, 2H), 3.43 (s, 2H), 4.87 (s, 1H), 6.54 (dd, J=3.4, 1.8 Hz, 1H), 6.80 (d, J=3.4 Hz, 1H), 6.93-7.02 (m, 1H), 7.03-7.24 (m, 4H), 7.25-7.38 (m, 4H), 7.55 (d, J=1.3 Hz, 1H), 7.88 (d, J=8.1 Hz, 1H)

Compound 14 (1-(3,4-Difluorobenzyl)-3'-(4-methoxyphenyl)-7'-(thiazol-2-yl)-1'H-spiro[piperidine-4,2'-quinazolin]-4'(3'H)-one); LCMS (ESI) 533 (M+H); $^1$H NMR (400 MHz, CHLOROFORM-d) δ ppm: 8.03 (d, J=8.1 Hz, 1H), 7.92 (d, J=3.2 Hz, 1H), 7.51-7.54 (m, 1H), 7.40-7.45 (m, 2H), 7.16 (d, J=8.8 Hz, 2H), 7.02-7.13 (m, 2H), 6.98 (d, J=8.8 Hz, 3H), 4.84 (s, 1H), 3.86 (s, 3H), 3.42 (s, 2H), 2.76 (d, J=12.1 Hz, 2H), 2.04-2.21 (m, 4H), 1.85 (td, J=12.8, 4.2 Hz, 2H)

Compound 45 (1-(3,4-Difluorobenzyl)-3'-(4-methoxyphenyl)-7'-(thiazol-5-yl)-1'H-spiro[piperidine-4,2'-quinazolin]-4'(3'H)-one); LCMS (ESI) 533 (M+H); $^1$H NMR (400 MHz, CHLOROFORM-d) δ ppm: 8.81 (s, 1H), 8.16 (s, 1H), 8.01 (d, J=8.1 Hz, 1H), 7.02-7.18 (m, 5H), 6.92-7.02 (m, 4H), 4.78 (s, 1H), 3.86 (s, 3H), 3.44 (s, 2H), 2.77 (d, J=12.0 Hz, 2H), 2.19 (t, J=11.8 Hz, 2H), 2.04-2.12 (m, 2H), 1.86 (td, J=12.9, 4.2 Hz, 2H)

Compound 41 (1-(3,4-Difluorobenzyl)-7'-(furan-2-yl)-3'-(4-(methylthio)phenyl)-1'H-spiro[piperidine-4,2'-quinazolin]-4'(3'H)-one); LCMS (ESI) 532 (M+H); $^1$H NMR (400 MHz, DICHLOROMETHANE-d$_2$) δ ppm: 1.81 (dd, J=12.8, 4.3 Hz, 2H), 2.07 (d, J=11.7 Hz, 2H), 2.18 (t, J=11.7 Hz, 2H), 2.53 (s, 3H), 2.73 (d, J=12.0 Hz, 2H), 3.42 (s, 2H), 4.86 (s, 1H), 6.54 (dd, J=3.4, 1.8 Hz, 1H), 6.79 (d, J=3.3 Hz, 1H), 6.98 (br.s., 1H), 7.02-7.23 (m, 5H), 7.33 (d, J=8.4 Hz, 2H), 7.54 (d, J=1.3 Hz, 1H), 7.88 (d, J=8.1 Hz, 1H)

Compound 9 (1-(3,4-Difluorobenzyl)-7'-(pyrimidin-4-yl)-3'-(4-(trifluoromethoxy)phenyl)-1'H-spiro[piperidine-4,2'-quinazolin]-4'(3'H)-one); LCMS (ESI) 582 (M+H); $^1$H NMR (400 MHz, DMSO-d$_6$) δ ppm: 9.29 (d, J=1.2 Hz, 1H), 8.92 (d, J=5.4 Hz, 1H), 8.04 (dd, J=5.4, 1.4 Hz, 1H), 8.01 (d, J=1.5 Hz, 1H), 7.81 (d, J=8.2 Hz, 1H), 7.55 (dd, J=8.2, 1.6 Hz, 1H), 7.43-7.49 (m, 2H), 7.37-7.42 (m, 2H), 7.22-7.36 (m, 3H), 7.04-7.10 (m, 1H), 3.44 (s, 2H), 2.60 (d, J=11.7 Hz, 2H), 2.42 (t, J=11.8 Hz, 2H), 2.02 (d, J=12.3 Hz, 2H), 1.59 (td, J=12.7, 4.4 Hz, 2H); $^{19}$F NMR (376 MHz, DMSO-d$_6$) δ ppm: −141.76 (d, J=8.7 Hz, 1F), −139.75--139.52 (m, 1F), −57.18 (br. s., 3F)

Example 13

Synthesis of Compound 77 (7'-Acetyl-1-(3,4-difluorobenzyl)-3'-(4-(trifluoromethoxy)phenyl)-1'H-spiro[piperidine-4,2'-quinazolin]-4'(3'H)-one)

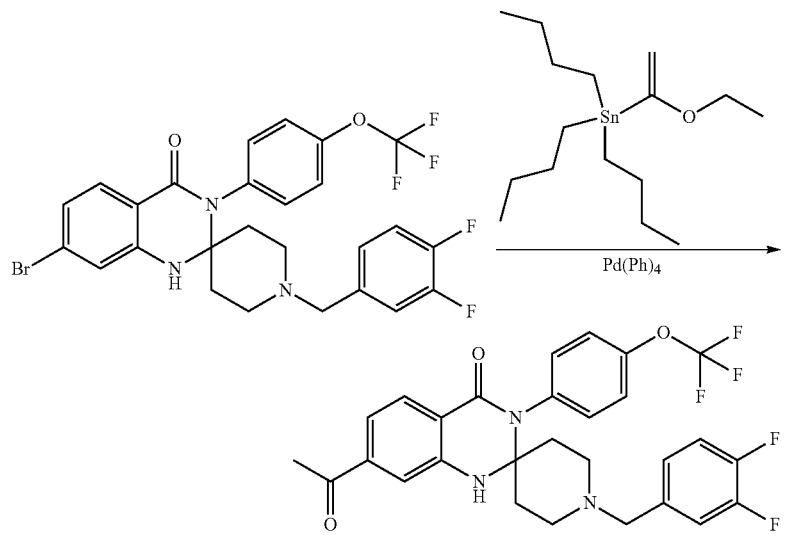

7'-Bromo-1-(3,4-difluorobenzyl)-3'-(4-(trifluoromethoxy)phenyl)-1'H-spiro[piperidine-4,2'-quinazolin]-4'(3'H)-one, compound 32 (100 mg, 0.17 mmol), tributyl-(1-ethoxy-vinyl)-stannane (66 µL, 0.19 mmol), and tetrakis(triphenylphosphine)palladium (0) (4 mg, 3.5 µmol) were combined into toluene (2 mL). The reaction mixture was degassed with nitrogen for 10 min and refluxed overnight. The reaction mixture was cooled, concentrated under vacuo and the residue was purified by chromatography using dichloromethane/ethyl acetate (0%-20%) as eluent to give title compound 7'-acetyl-1-(3,4-difluorobenzyl)-3'-(4-(trifluoromethoxy)phenyl)-1'H-spiro[piperidine-4,2'-quinazolin]-4'(3'H)-one (43 mg; 46%) as a yellow solid; LCMS (ESI) 546 (M+H); $^1$H NMR (400 MHz, DICHLOROMETHANE-$d_2$) δ ppm: 7.98 (d, J=8.5 Hz, 1H), 7.44 (d, J=1.6 Hz, 1H), 7.31-7.38 (m, 2H), 7.25-7.31 (m, 2H), 7.03-7.15 (m, 2H), 6.94-7.00 (m, 1H), 3.43 (s, 2H), 2.59 (s, 3H), 2.19 (s, 2H), 2.06 (d, J=11.1 Hz, 2H), 1.78 (d, J=4.3 Hz, 2H), 1.60-1.68 (m, 1H), 1.56 (s, 1H), 1.36 (d, J=7.4 Hz, 2H), 0.92 (t, J=7.3 Hz, 2H).

Example 14

Synthesis of Compound 79 (1-(3,4-Difluorobenzyl)-4'-oxo-3'-(4-(trifluoromethoxy)phenyl)-3',4'-dihydro-1'H-spiro[piperidine-4,2'-quinazoline]-7'-carbonitrile)

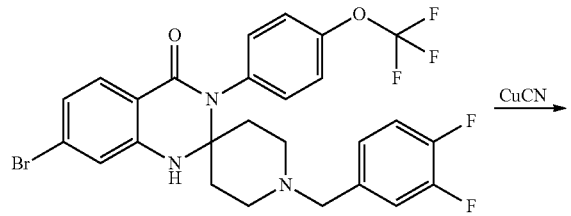

A scintillation vial was charged with 7'-bromo-1-(3,4-difluorobenzyl)-3'-(4-(trifluoromethoxy)phenyl)-1'H-spiro[piperidine-4,2'-quinazolin]-4'(3'H)-one, compound 32 (291 mg, 0.50 mmol), copper cyanide (90 mg, 1.00 mmol) and 1-methyl-pyrrolidin-2-one (1 mL). The reaction mixture was degassed with nitrogen and heated at 140° C. for 3 h. The reaction mixture was cooled, poured into water and the precipitate was filtered and washed with water. The precipitate was dissolved in DCM/MeOH, the insoluble copper was filtered and the filtrate was evaporated under reduced pressure. The residue was purified by chromatography using heptane/ethyl acetate (0%-30%) as eluent to give title compound 1-(3,4-Difluorobenzyl)-4'-oxo-3'-(4-(trifluoromethoxy-phenyl)-3',4'-dihydro-1'H-spiro[piperidine-4,2'-quinazoline]-7'-carbonitrile (50 mg; 19%); LCMS (ESI) 529 (M+H).

Example 15

Synthesis of Compound 37 (7'-bromo-1-(3,4-difluorobenzyl)-3'-(4-(2-methoxyethoxy)phenyl)-1'H-spiro[piperidine-4,2'-quinazolin]-4'(3'H)-one)

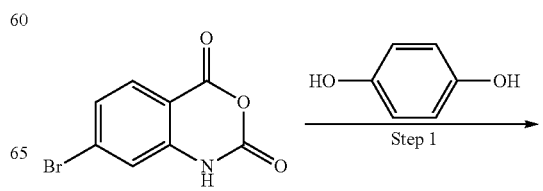

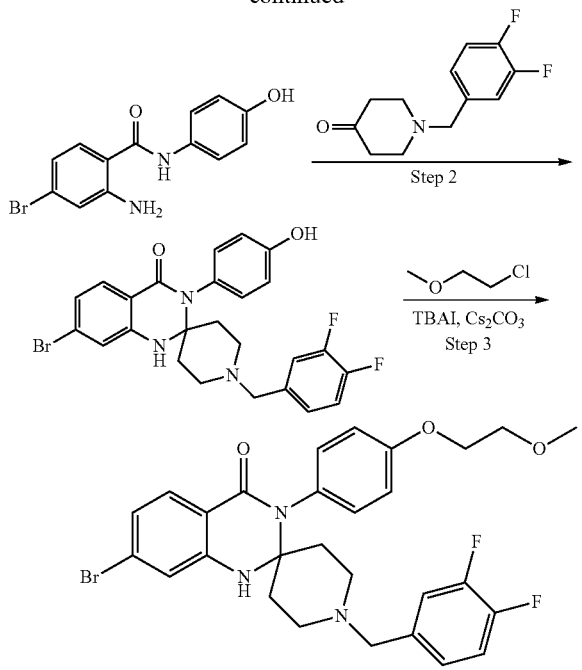

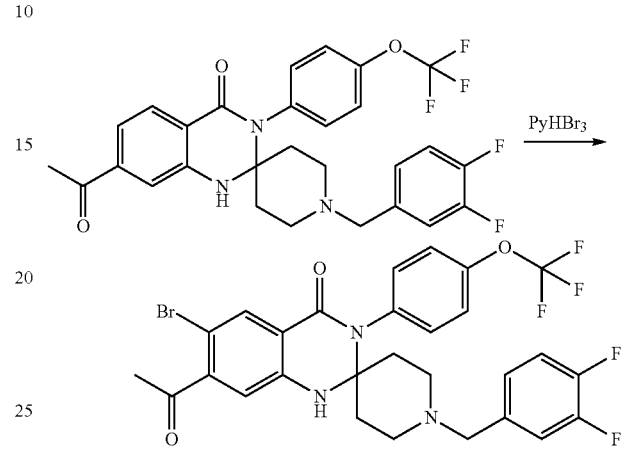

Step 1: Prepared following the same procedure as example 1, step 1 to give 2-amino-4-bromo-N-(4-hydroxyphenyl)-benzamide (0.49 g; 76%) as a yellow solid; $^1$H NMR (400 MHz, DMSO-d$_6$) δ ppm: 9.82 (s, 1H), 9.22 (s, 1H), 7.53 (d, J=8.5 Hz, 1H), 7.40-7.46 (m, 2H), 6.95 (d, J=2.0 Hz, 1H), 6.68-6.74 (m, 3H), 6.53 (s, 2H).

Step 2: Prepared following the same procedure as example 4, step 2 to give 7'-bromo-1-(3,4-difluorobenzyl)-3'-(4-hydroxyphenyl)-1'H-spiro[piperidine-4,2'-quinazolin]-4'(3'H)-one (0.35 g; 55%) as a white solid; LCMS (ESI) 514 (M+H); $^1$H NMR (400 MHz, DMSO-d$_6$) δ ppm: 9.60 (s, 1H), 7.55 (d, J=8.3 Hz, 1H), 7.22-7.37 (m, 3H), 7.12 (s, 1H), 7.04-7.09 (m, 1H), 6.94-6.99 (m, 2H), 6.88 (dd, J=8.3, 1.9 Hz, 1H), 6.76-6.82 (m, 2H), 3.42 (s, 2H), 2.57 (d, J=10.7 Hz, 2H), 2.32 (t, J=11.6 Hz, 2H), 1.90 (dd, J=12.6, 1.0 Hz, 2H), 1.54-1.64 (m, 2H); $^{19}$F NMR (376 MHz, DMSO-d$_6$) δ ppm: −141.82 (br.s., 1F) −139.77−−139.51 (m, 1F).

Step 3: Prepared following the same procedure as example 10, step 4 to give title compound 7'-bromo-1-(3,4-difluorobenzyl)-3'-(4-(2-methoxyethoxyl)phenyl)-1'H-spiro[piperidine-4,2'-quinazolin]-4'(3'H)-one (0.35 g; 55%) as a white solid; LCMS (ESI) 572 (M+H); $^1$H NMR (400 MHz, DMSO-d$_6$) δ ppm: 7.56 (d, J=8.3 Hz, 1H), 7.21-7.37 (m, 3H), 7.15 (s, 1H), 7.03-7.12 (m, 3H), 6.96-7.01 (m, 2H), 6.89 (dd, J=8.3, 1.9 Hz, 1H), 4.10-4.15 (m, 2H), 3.66-3.70 (m, 2H), 3.42 (s, 2H), 3.33 (s, 3H), 2.57 (d, J=11.9 Hz, 2H), 2.28-2.38 (m, 2H), 1.93 (d, J=12.4 Hz, 2H), 1.59 (td, J=13.1, 4.7 Hz, 2H); $^{19}$F NMR (376 MHz, DMSO-d$_6$) δ ppm: −141.89−−141.69 (m, 1F) −139.75−−139.50 (m, 1F).

The following compounds were synthesized in an analogous manner:

Compound 106 (1-(3,4-difluorobenzyl)-7'-fluoro-3'-(4-(2-methoxyethoxyl)phenyl)-1'H-spiro[piperidine-4,2'-quinazolin]-4'(3'H)-one); LCMS (ESI) 512 (M+H); $^1$H NMR (400 MHz, DMSO-d$_6$) δ ppm: 7.69 (dd, J=8.7, 6.7 Hz, 1H), 7.32 (dt, J=10.8, 8.4 Hz, 1H), 7.25 (ddd, J=11.7, 8.0, 1.8 Hz, 1H), 7.20 (s, 1H), 7.03-7.12 (m, 3H), 6.96-7.01 (m, 2H), 6.80 (dd, J=11.0, 2.5 Hz, 1H), 6.54 (td, J=8.7, 2.5 Hz, 1H), 4.10-4.15 (m, 2H), 3.65-3.70 (m, 2H), 3.42 (s, 2H), 3.33 (s, 3H), 2.58 (d, J=12.0 Hz, 2H), 2.33 (t, J=11.8 Hz, 2H), 1.93 (d, J=12.3 Hz, 2H), 1.59 (td, J=12.9, 4.6 Hz, 2H); $^{19}$F NMR (376 MHz, DMSO-d$_6$) δ ppm: −141.77 (d, J=8.5 Hz, 1F) −139.73−−139.49 (m, 1F) −107.18 (br.s., 1F)

Example 16

Synthesis of Compound 12 (7'-Acetyl-6'-bromo-1-(3,4-difluorobenzyl)-3'-(4-(trifluoromethoxy)phenyl)-1'H-spiro[piperidine-4,2'-quinazolin]-4'(3'H)-one)

To a solution of 7'-acetyl-1-(3,4-difluorobenzyl)-3'-(4-(trifluoromethoxy)phenyl)-1'H-spiro[piperidine-4,2'-quinazolin]-4'(3'H)-one, compound 77 (51 mg, 0.09 mmol) in ethanol (1.6 mL) and water (0.4 mL), a solution of pyridinium tribromide (43 mg, 0.14 mmol) in ethanol (2 mL) was added dropwise over a period of 30 min. The reaction solution was then stirred for 2 h, before a 10% solution of sodium thiosulfate was added. The pH was then adjusted to pH=8 with a saturated solution of sodium bicarbonate. The aqueous mixture was extracted with ethyl acetate. The combined organic phase was dried over anhydrous sodium sulfate, filtered and evaporated in vacuo to give title compound. The combined organic phase was dried over anhydrous sodium sulfate, filtered and evaporated in vacuo to give title compound 7'-acetyl-6'-bromo-1-(3,4-difluorobenzyl)-3'-(4-(trifluoromethoxy)phenyl)-1'H-spiro[piperidine-4,2'-quinazolin]-4'(3'H)-one; LCMS (ESI) 625 (M+H); $^1$H NMR (400 MHz, DICHLOROMETHANE-d$_2$) δ ppm: 8.09 (s, 1H), 7.30-7.38 (m, 3H), 7.23-7.30 (m, 3H), 7.02-7.16 (m, 3H), 6.87 (s, 1H), 4.99 (s, 1H), 3.42 (s, 3H), 2.73 (d, J=11.6 Hz, 3H), 2.61 (s, 3H), 2.17 (br.s., 3H), 2.05 (d, J=11.6 Hz, 3H), 1.78 (br.s., 3H).

Example 17

Synthesis of 107 (7'-Bromo-1-(1-(3,4-difluorophenyl)-2,2,2-trifluoroethyl)-3'-(4-(trifluoromethoxy)phenyl)-1'H-spiro[piperidine-4,2'-quinazolin]-4'(3'H)-one)

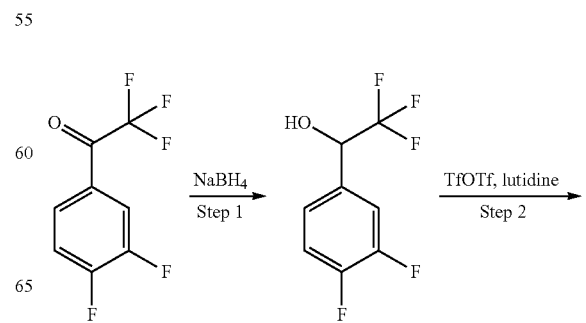

-continued

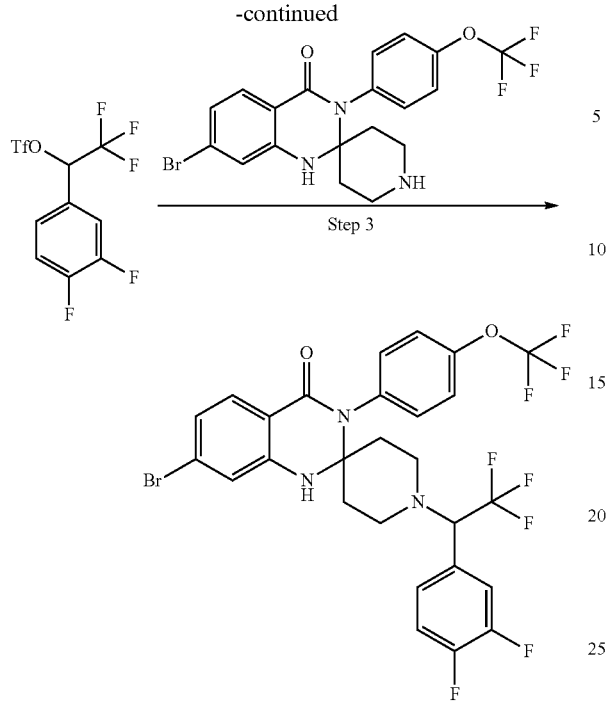

Step 1: A round bottom flask equipped with a stir bar was charged with 1-(3,4-difluoro-phenyl)-2,2,2-trifluoro-ethanone (0.500 g, 2.38 mmol) and dry methanol (10 mL). To this mixture was added sodium borohydride (0.135 g, 3.57 mmol) portionwise. The reaction was allowed 1 h at RT, then poured into dilute HCl. After 10 min, it was extracted with ethyl acetate. The combined organic phase was washed with a solution of sodium carbonate, dried over anhydrous sodium sulfate, filtered and evaporated in vacuo to give 1-(3,4-difluoro-phenyl)-2,2,2-trifluoro-ethanol (500 mg; 99%) as an oil. The material was used as is in the next step.

Step 2: A round bottom flask equipped with a stir bar and nitrogen inlet was charged with 1-(3,4-difluoro-phenyl)-2,2,2-trifluoro-ethanol (0.442 g, 2.08 mmol), 2,6-lutidine (0.388 ml, 3.33 mmol) and cyclohexane (10 mL). The reaction mixture was cooled to −10° C. in a brine/ice bath. Triflic anhydride (3.13 mL, 3.13 mmol) was added dropwise over 30 minutes and the reaction was allowed to stir between 0° C. and 10° C. for 1.5 h. The reaction mixture was diluted with cyclohexane (25 mL) and water (25 mL). The organic phase was washed with 1N HCl (25 mL) and water (25 mL). The combined organic phase was dried over anhydrous sodium sulfate, filtered and evaporated in vacuo to give trifluoromethanesulfonic acid 1-(3,4-difluorophenyl)-2,2,2-trifluoroethyl ester (650 mg; 91%).

Step 3: Prepared following the same procedure as example 4, step 2 to give title compound 7'-bromo-1-(1-(3,4-difluorophenyl)-2,2,2-trifluoroethyl)-3'-(4-(trifluoromethoxy)phenyl)-1'H-spiro[piperidine-4,2'-quinazolin]-4'(3'H)-one (22 mg; 22%); LCMS (ESI) 649 (M+H); $^1$H NMR (400 MHz, METHANOL-$d_4$) δ ppm: 7.64 (d, J=8.3 Hz, 1H), 7.24-7.47 (m, 5H), 7.21 (br.s., 1H), 7.04-7.14 (m, 2H), 6.94 (dd, J=8.3, 1.7 Hz, 1H), 5.99 (d, J=6.1 Hz, 1H), 4.32 (q, J=8.7 Hz, 1H), 2.77-2.94 (m, 2H), 2.63-2.76 (m, 1H), 2.46 (t, J=11.7 Hz, 1H), 2.00-2.15 (m, 2H), 1.76 (td, J=12.7, 4.4 Hz, 2H).

The following compound was synthesized in an analogous manner:

Compound 43 (7'-Bromo-1-(2,2,2-trifluoro-1-(3-fluorophenyl)ethyl)-3'-(4-(trifluoromethoxy)phenyl)-1'H-spiro[piperidine-4,2'-quinazolin]-4'(3'H)-one); LCMS (ESI) 631 (M+H); $^1$H NMR (400 MHz, METHANOL-$d_4$) δ ppm: 7.64 (d, J=8.4 Hz, 1H), 7.37-7.50 (m, 3H), 7.33 (s, 2H), 7.20 (d, J=7.7 Hz, 1H), 7.04-7.16 (m, 3H), 6.94 (dd, J=8.4, 1.7 Hz, 1H), 4.32 (q, J=8.8 Hz, 1H), 2.79-2.96 (m, 2H), 2.67-2.77 (m, 1H), 2.46 (t, J=11.8 Hz, 1H), 2.08 (t, J=9.9 Hz, 2H), 1.76 (td, J=12.7, 4.5 Hz, 2H)

Example 18

Synthesis of Compound 117 (1-(3,4-Difluorobenzyl)-7'-(5-((dimethylamino)methyl)furan-2-yl)-3'-(4-methoxyphenyl)-1'H-spiro[piperidine-4,2'-quinazolin]-4'(3'H)-one)

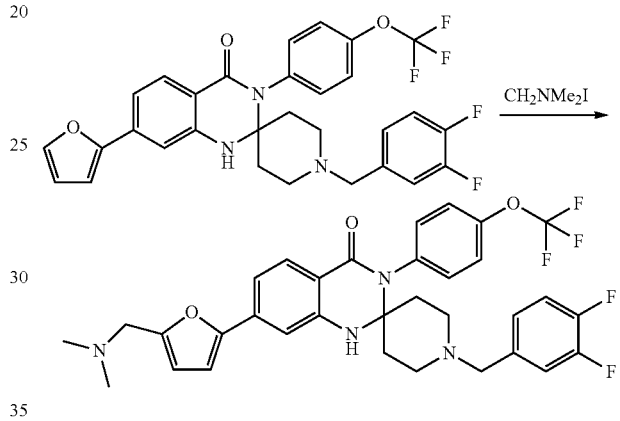

To a solution of 1-(3,4-difluorobenzyl)-7'-(furan-2-yl)-3'-(4-methoxyphenyl)-1'H-spiro[piperidine-4,2'-quinazolin]-4'(3'H)-one, compound 11 (14 mg, 0.026 mmol) in acetonitrile (1.5 mL) was added dimethyl-methylene-ammonium iodide (20 mg, 0.106 mmol). The reaction was heated at 60° C. for 16 hours and then concentrated to dryness. The reaction mixture was diluted with ethyl acetate (25 mL) and saturated aqueous sodium bicarbonate (25 mL) and stirred for some time. The aqueous phase was extracted with ethyl acetate and the combined organic phase was dried over anhydrous sodium sulfate, filtered and evaporated in vacuo. The residue was purified by chromatography using ethyl acetate/methanol as eluent to give title compound 1-(3,4-difluorobenzyl)-7'-(5-((dimethylamino)methyl)furan-2-yl)-3'-(4-methoxyphenyl)-1'H-spiro[piperidine-4,2'-quinazolin]-4'(3'H)-one (5.8 mg; 38%) as an off-white foam; LCMS (ESI) 574 (M+H); $^1$H NMR (400 MHz, DICHLOROMETHANE-$d_2$) δ ppm: 1.80 (dd, J=12.9, 4.2 Hz, 2H), 2.06 (d, J=12.1 Hz, 2H), 2.20 (s, 2H), 2.32 (s, 6H), 2.72 (d, J=12.1 Hz, 2H), 3.43 (s, 2H), 3.57 (s, 2H), 3.85 (s, 3H), 4.91 (s, 1H), 6.36 (d, J=3.3 Hz, 1H), 6.73 (d, J=3.3 Hz, 1H), 6.97 (d, J=8.8 Hz, 3H), 7.03-7.22 (m, 6H), 7.85 (d, J=8.1 Hz, 1H).

The following compound was synthesized in an analogous manner:

Compound 74 (1-(3,4-Difluorobenzyl)-7'-(5-((dimethylamino)methyl)furan-2-yl)-3'-(4-(trifluoromethoxy)phenyl)-1'H-spiro[piperidine-4,2'-quinazolin]-4'(3'H)-one); LCMS (ESI) 627 (M+H); $^1$H NMR (400 MHz, DICHLOROMETHANE-$d_2$) δ ppm: 1.76 (d, J=4.2 Hz, 2H), 2.09 (d, J=11.9 Hz, 2H), 2.21 (s, 2H), 2.29 (s, 6H), 2.72 (br.s., 2H), 3.44 (s, 2H), 3.53 (s, 2H), 4.92 (s, 1H), 6.34 (d, J=3.3

Hz, 1H), 6.73 (d, J=3.3 Hz, 1H), 6.93-7.02 (m, 1H), 7.03-7.21 (m, 4H), 7.24-7.39 (m, 4H), 7.86 (d, J=8.1 Hz, 1H)

Example 19

Synthesis of Compound 78 (1-(1-(3,4-Difluorophenyl)-2,2,2-trifluoroethyl)-7'-fluoro-3'-(4-(trifluoromethoxy)phenyl)-1'H-spiro[azetidine-3,2'-quinazolin]-4'(3'H)-one)

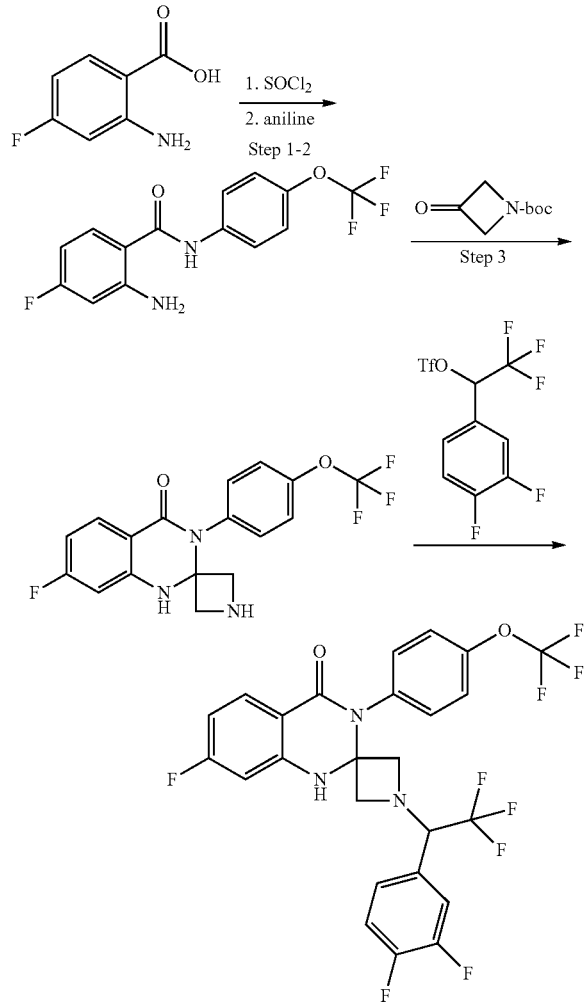

Prepared following the same procedures as example 7 step 1 through 3 and example 26 step 3 to give title compound 1-(1-(3,4-difluorophenyl)-2,2,2-trifluoroethyl)-7'-fluoro-3'-(4-(trifluoromethoxy)phenyl)-1'H-spiro[azetidine-3,2'-quinazolin]-4'(3'H)-one (3 mg; 2%); LCMS (ESI) 562 (M+H); $^{1}$H NMR (400 MHz, CHLOROFORM-d) δ ppm: 7.93 (dd, J=8.6, 6.2 Hz, 1H), 7.35 (d, J=8.3 Hz, 2H), 7.22-7.31 (m, 4H), 7.05-7.17 (m, 2H), 6.95 (br.s., 1H), 6.61-6.70 (m, 1H), 6.58 (dd, J=9.5, 2.2 Hz, 1H), 5.40 (s, 1H), 3.62 (d, J=8.2 Hz, 1H), 3.54 (q, J=6.4 Hz, 1H), 3.31-3.38 (m, 1H), 3.16 (d, J=8.2 Hz, 1H).

The following compound was synthesized in an analogous manner:

Compound 53 (7'-Fluoro-1-(2,2,2-trifluoro-1-(3-fluorophenyl)ethyl)-3'-(4-(trifluoromethoxy)phenyl)-1'H-spiro[azetidine-3,2'-quinazolin]-4'(3'H)-one); LCMS (ESI) 544 (M+H); $^{1}$H NMR (400 MHz, CHLOROFORM-d) δ ppm: 7.92 (dd, J=8.6, 6.3 Hz, 1H), 7.21-7.37 (m, 6H), 7.03-7.13 (m, 1H), 6.93-7.01 (m, 2H), 6.64 (td, J=8.6, 2.2 Hz, 1H), 6.58 (dd, J=9.6, 2.2 Hz, 1H), 5.44 (s, 1H), 3.53-3.65 (m, 2H), 3.31-3.38 (m, 2H), 3.17 (d, J=8.3 Hz, 1H)

Example 20

Synthesis of Compound 30 (Ethyl 1-(1-(2-chlorophenyl)ethyl)-4'-oxo-3'-(4-(trifluoromethoxy)phenyl)-3',4'-dihydro-1'H-spiro[azetidine-3,2'-quinazoline]-7'-carboxylate)

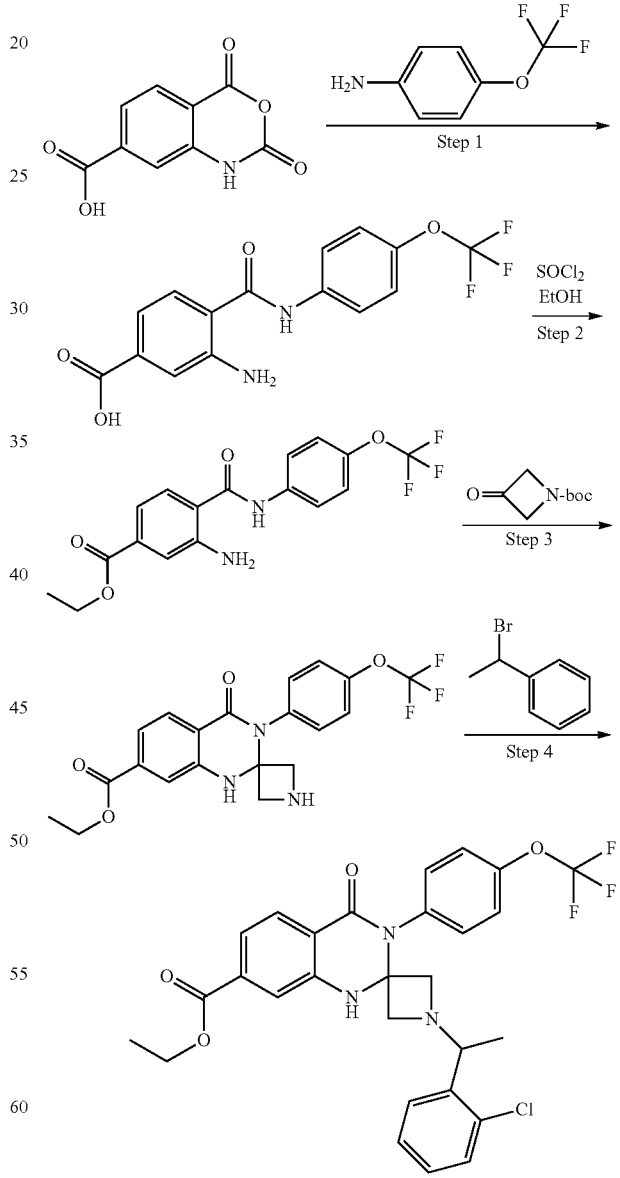

Step 1: Prepared following the same procedure as example 4 step 1 to give 3-amino-4-((4-(trifluoromethoxy)phenyl)carbamoyl)benzoic acid (2.97 g; 87%).

Step 2: A round bottom flask equipped condenser and nitrogen inlet was charged with 2,4-dioxo-1,4-dihydro-2H-benzo[d][1,3]oxazine-7-carboxylic acid (681 mg; 2.00 mmol) and ethanol (50 mL). Thionyl chloride (1.5 mL; 20.0 mmol) was added and the reaction mixture was heated at 60° C. for 6 h. The solvent was evaporated under reduced pressure and residue was dissolved in ethyl acetate, washed with a saturated solution of sodium bicarbonate, dried over anhydrous sodium sulfate, filtered and evaporated under reduced pressure to give ethyl 3-amino-4-((4-(trifluoromethoxy)phenyl)carbamoyl)benzoate (715 mg; 97%). The material was used as is in the next step; LCMS (ESI) 369 (M+H); $^1$H NMR (400 MHz, CHLOROFORM-d) δ ppm: 7.81 (br.s., 1H), 7.63 (d, J=9.0 Hz, 2H), 7.52 (d, J=8.2 Hz, 1H), 7.40-7.44 (m, 1H), 7.36 (dd, J=8.2, 1.4 Hz, 1H), 7.25 (d, J=8.8 Hz, 2H), 5.59 (br.s., 1H), 4.39 (q, J=7.1 Hz, 2H), 1.41 (t, J=7.1 Hz, 2H).

Step 3: Prepared following the same procedure as example 6 step 2 to give ethyl 4'-oxo-3'-(4-(trifluoromethoxy)phenyl)-3',4'-dihydro-1'H-spiro[azetidine-3,2'-quinazoline]-7'-carboxylate tosylate salt (586 mg; 40%); LCMS (ESI) 422 (M+H); $^1$H NMR (400 MHz, METHANOL-d$_4$) δ ppm: 7.93 (d, J=8.2 Hz, 1H), 7.66-7.73 (m, 3H), 7.50-7.61 (m, 5H), 7.22 (d, J=8.0 Hz, 3H), 4.36-4.49 (m, 4H), 4.29 (d, J=13.1 Hz, 2H), 2.36 (s, 4H), 1.40 (t, J=7.1 Hz, 3H).

Step 4: Prepared following the same procedure as example 7 step 4 to give title compound ethyl 1-(1-(2-chlorophenyl)ethyl)-4'-oxo-3'-(4-(trifluoromethoxy)phenyl)-3',4'-dihydro-1'H-spiro[azetidine-3,2'-quinazoline]-7'-carboxylate (45 mg; 32%); LCMS (ESI) 560 (M+H); $^1$H NMR (400 MHz, CHLOROFORM-d) δ ppm: 7.99 (d, J=8.4 Hz, 1H), 7.57 (dd, J=4.1, 2.8 Hz, 2H), 7.24-7.38 (m, 7H), 7.10-7.23 (m, 2H), 5.44 (s, 1H), 4.41 (q, J=7.1 Hz, 2H), 3.68 (q, J=6.4 Hz, 1H), 3.48 (d, J=7.9 Hz, 1H), 3.26 (d, J=7.3 Hz, 1H), 3.19 (d, J=8.1 Hz, 1H), 3.13 (d, J=8.2 Hz, 1H), 1.43 (t, J=7.1 Hz, 3H), 1.10 (d, J=6.4 Hz, 3H).

The following compounds were synthesized in an analogous manner:

Compound 34 (Ethyl 1-(1-(3,4-difluorophenyl)-2,2,2-trifluoroethyl)-4'-oxo-3'-(4-(trifluoromethoxy)phenyl)-3',4'-dihydro-1'H-spiro[azetidine-3,2'-quinazoline]-7'-carboxylate)

Compound 87 (Ethyl 1-(1-(4-fluorophenyl)ethyl)-4'-oxo-3'-(4-(trifluoromethoxy)phenyl)-3',4'-dihydro-1'H-spiro[azetidine-3,2'-quinazoline]-7'-carboxylate); LCMS (ESI) 544 (M+H); $^1$H NMR (400 MHz, CHLOROFORM-d) δ ppm: 7.98 (d, J=8.4 Hz, 1H), 7.53-7.60 (m, 2H), 7.30-7.36 (m, 2H), 7.24-7.30 (m, 3H), 7.10 (dd, J=8.5, 5.5 Hz, 2H), 6.94 (t, J=8.6 Hz, 2H), 5.46 (s, 1H), 4.41 (q, J=7.1 Hz, 2H), 3.46-3.51 (m, 1H), 3.15-3.21 (m, 1H), 3.03-3.11 (m, 2H), 2.98 (d, J=8.1 Hz, 1H), 1.43 (t, J=7.1 Hz, 3H), 1.11 (d, J=6.4 Hz, 3H)

Compound 18 (Ethyl 1-(2-chlorobenzyl)-4'-oxo-3'-(4-(trifluoromethoxy)phenyl)-3',4'-dihydro-1'H-spiro[azetidine-3,2'-quinazoline]-7'-carboxylate); LCMS (ESI) 546 (M+H); $^1$H NMR (400 MHz, CHLOROFORM-d) δ ppm: 7.99 (d, J=8.1 Hz, 1H), 7.53-7.60 (m, 2H), 7.29-7.35 (m, 3H), 7.24-7.29 (m, 3H), 7.16-7.22 (m, 2H), 7.11-7.16 (m, 1H), 5.52 (s, 1H), 4.41 (q, J=7.1 Hz, 2H), 3.62 (s, 2H), 3.48 (d, J=9.0 Hz, 2H), 3.27 (d, J=9.0 Hz, 2H), 1.42 (t, J=7.1 Hz, 3H)

Example 21

Synthesis of Compound 91 (3-((4'-Oxo-3'-(4-(trifluoromethoxy)phenyl)-7'-(trifluoromethyl)-3',4'-dihydro-1'H-spiro[azetidine-3,2'-quinazolin]-1-yl)methyl)benzonitrile)

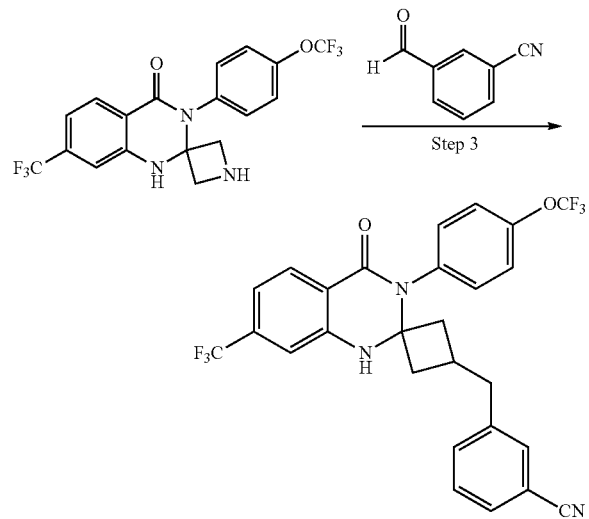

Prepared following the same procedure as example 8, step 1 and example 6, step 2.

Step 3: Prepared following the same procedure as example 7 step 4 to give title compound 3-((4'-oxo-3'-(4-(trifluoromethoxy)phenyl)-7'-(trifluoromethyl)-3',4'-dihydro-1'H-spiro[azetidine-3,2'-quinazolin]-1-yl)methyl)benzonitrile (67 mg; 99%); $^1$H NMR (400 MHz, DICHLOROMETHANE-d$_2$) δ ppm: 7.99 (d, J=8.5 Hz, 1H), 7.67 (s, 1H), 7.56-7.62 (m, 1H), 7.51-7.55 (m, 1H), 7.46-7.50 (m, 1H), 7.34-7.41 (m, 4H), 7.29-7.34 (m, 2H), 7.12-7.16 (m, 2H), 5.78 (s, 1H), 4.70 (d, J=3.9 Hz, 1H), 3.49 (s, 2H), 3.42-3.47 (m, 2H), 3.18-3.24 (m, 2H).

Example 22

Synthesis of Compound 70 (1-(2-Chlorobenzyl)-7'-fluoro-3'-(4-(trifluoromethoxy)phenyl)-1'H-spiro[azetidine-3,2'-quinazolin]-4'(3'H)-one)

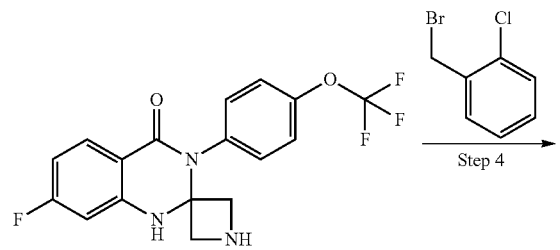

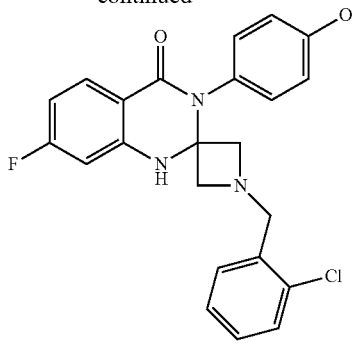

Prepared following the same procedure as example 19 through step 3.

Step 4: Prepared following the same procedure as example 7 step 4 to give title compound 1-(2-chlorobenzyl)-7'-fluoro-3'-(4-(trifluoromethoxy)phenyl)-1'H-spiro[azetidine-3,2'-quinazolin]-4'(3'H)-one (632 mg; 26%); LCMS (ESI) 492 (M+H).

The following compound was synthesized in an analogous manner:

Compound 82 (7'-Fluoro-1-(1-(4-fluorophenyl)ethyl)-3'-(4-(trifluoromethoxy)phenyl)-1'H-spiro[azetidine-3,2'-quinazolin]-4'(3'H)-one); LCMS (ESI) 490 (M+H); $^1$H NMR (400 MHz, CHLOROFORM-d) δ ppm: 7.93 (dd, J=8.6, 6.3 Hz, 1H), 7.33 (d, J=8.4 Hz, 2H), 7.25 (d, J=8.9 Hz, 2H), 7.10 (dd, J=8.5, 5.5 Hz, 2H), 6.94 (t, J=8.6 Hz, 2H), 6.59-6.66 (m, 1H), 6.55 (dd, J=9.7, 2.2 Hz, 1H), 5.43 (s, 1H), 3.50 (d, J=6.4 Hz, 1H), 3.19 (d, J=6.6 Hz, 1H), 3.08 (t, J=6.5 Hz, 2H), 2.98 (d, J=8.0 Hz, 1H), 1.12 (d, J=6.4 Hz, 3H)

Example 23

Synthesis of Compound 44 (3'-(4-Methoxyphenyl)-4-(phenylamino)-1'H-spiro[cyclohexane-1,2'-quinazolin]-4'(3'H)-one)

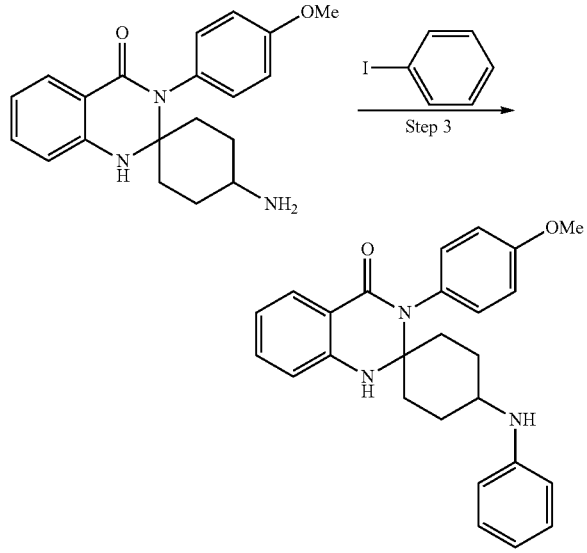

Prepared following the same procedure as example 1 through step 2; LC/MS (ESI) 338 (M+H); $^1$H NMR (METHANOL-d$_4$) δ: 7.79-7.83 (m, 1H), 7.71 (d, J=8.2 Hz, 2H), 7.37-7.44 (m, 1H), 7.23 (d, J=8.0 Hz, 3H), 7.14 (d, J=8.8 Hz, 2H), 6.87-7.08 (m, 4H), 3.83 (s, 3H), 2.37 (s, 4H), 2.25 (d, J=11.7 Hz, 2H), 1.75-1.91 (m, 4H), 1.57-1.68 (m, 2H).

Step 3: A scintillation vial was charged with 4-amino-3'-(4-methoxyphenyl)-1'H-spiro[cyclohexane-1,2'-quinazolin]-4'(3'H)-one tosylate salt (127 mg, 0.25 mmol), iodobenzene (50 mg, 0.25 mmol), X-Phos (20 mg, 0.04 mmol), cesium carbonate (244 mg, 0.75 mmol) and dioxane (2.5 mL). The reaction mixture was degassed with N$_2$ and then Pd(OAc)$_2$ (7 mg, 0.03 mmol) was added. The reaction was heated at 90° C. for 4 h. The reaction mixture was cooled, and ethyl acetate (50 mL) and water (50 mL) were added. The phases were separated, the aqueous phase was extracted with ethyl acetate (2×5 mL), the combined organic phase was dried over anhydrous sodium sulfate, filtered and the solvent was evaporated under reduced pressure. The material was purified by chromatography using heptane/ethyl acetate (0-50%) as eluant to give title compound 3'-(4-methoxyphenyl)-4-(phenylamino)-1'H-spiro[cyclohexane-1,2'-quinazolin]-4'(3'H)-one (10 mg; 10%); LCMS (ESI) 414 (M+H); $^1$H NMR (CHLOROFORM-d) δ: 7.99 (d, J=7.2 Hz, 1H), 7.37 (t, J=7.1 Hz, 1H), 7.11-7.19 (m, 4H), 6.90-7.01 (m, 3H), 6.79 (d, J=8.0 Hz, 1H), 6.69 (t, J=7.3 Hz, 1H), 6.49-6.56 (m, 2H), 4.61 (s, 1H), 3.86 (s, 3H), 3.49 (br.s., 1H), 3.10-3.19 (m, 1H), 2.24 (d, J=12.4 Hz, 2H), 2.09 (d, J=13.1 Hz, 2H), 1.67 (td, J=13.6, 3.6 Hz, 2H), 1.30-1.43 (m, 2H).

Example 24

Synthesis of Compound 108 (7-Bromo-1'-(3,4-difluorobenzyl)-3-(4-methoxyphenyl)spiro[benzo[e][1,3]oxazine-2,4'-piperidin]-4(3H)-one)

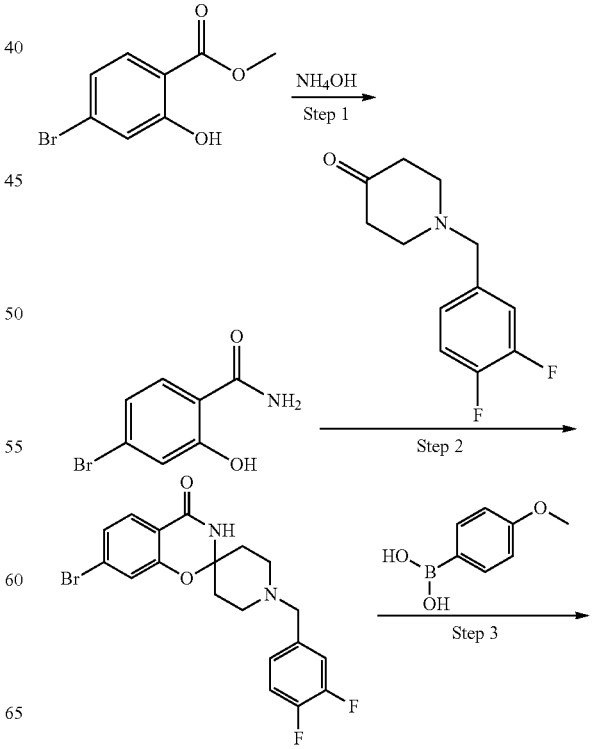

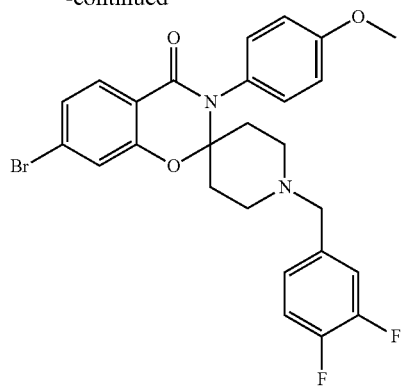

Step 1: To a solution of 4-bromo-2-hydroxy-benzoic acid methyl ester (4.62 g, 20.0 mmol) in isopropanol (40 mL) under nitrogen was added ammonium hydroxide (80 mL). The reaction mixture was stirred overnight at room temperature. The solvent was evaporated under reduced pressure to give 4-bromo-2-hydroxy-benzamide (2.6 g; 60%). The material was used as is in the next step.

Step 2: A round bottom flask was charged with 4-bromo-2-hydroxy-benzamide (864 mg, 4.00 mmol), 1-(3,4-difluoro-benzyl)-piperidin-4-one (901 mg, 4.00 mmol), toluene-4-sulfonic acid hydrate (76.1 mg, 0.40 mmol) and toluene (10 mL). The mixture was heated at 140° C. bath temperature for 4 h. The reaction mixture was cooled down, diluted with ethyl acetate and an aqueous solution of sodium carbonate was added. The aqueous phase was extracted with ethyl acetate and the combined organic phase was dried over anhydrous sodium sulfate, filtered and evaporated in vacuo. The material was purified by chromatography using dichloromethane-ethyl acetate (0-100%), then dichloromethane/dichloromethane/methanol/ammonia (95:4.5:0.5), gradient 0 to 100% as eluent to give 7-bromo-1'-(3,4-difluorobenzyl)spiro[benzo[e][1,3]oxazine-2,4'-piperidin]-4(3H)-one (800 mg, 47%); LCMS (ESI) 423 (M+H); $^1$H NMR (CHLOROFORM-d) δ: 7.79 (d, J=8.2 Hz, 1H), 7.23 (dd, J=8.3, 1.6 Hz, 1H), 7.17-7.21 (m, 2H), 7.07-7.16 (m, 1H), 6.99-7.05 (m, 1H), 6.29 (s, 1H), 3.50 (s, 2H), 2.62 (d, J=11.6 Hz, 2H), 2.45-2.54 (m, 2H), 2.20 (d, J=13.2 Hz, 2H), 1.84-1.93 (m, 2H).

Step 3: To a mixture of 7-bromo-1'-(3,4-difluorobenzyl)spiro[benzo[e][1,3]oxazine-2,4'-piperidin]-4(3H)-one (106 mg, 0.25 mmol), (4-methoxyphenyl)boronic acid (76 mg, 0.50 mmol), copper acetate (90 mg, 0.50 mmol), 4 A molecular sieves and dichloromethane (5 mL) was added triethylamine (50.6 mg, 0.50 mmol) and the reaction was stirred overnight at room temperature. The reaction was filtered through celite and the solvent was evaporated under reduced pressure. The material was purified by chromatography using heptane/ethyl acetate (0-70%) as eluent to give title compound 7-bromo-1'-(3,4-difluorobenzyl)-3-(4-methoxyphenyl)spiro[benzo[e][1,3]oxazine-2,4'-piperidin]-4(3H)-one (16 mg; 12%); LCMS (ESI) 529 (M+H); $^1$H NMR (CHLOROFORM-d) δ: 7.85 (d, J=8.0 Hz, 1H), 7.25 (s, 2H), 7.02-7.16 (m, 4H), 6.97 (d, J=8.7 Hz, 3H), 3.85 (s, 3H), 3.44 (s, 2H), 2.68 (d, J=11.2 Hz, 2H), 2.37 (t, J=11.2 Hz, 2H), 2.17 (d, J=12.6 Hz, 2H), 1.82 (td, J=12.9, 4.4 Hz, 2H).

Example 25

Synthesis of Compound 88 (tert-Butyl (3'-(4-methoxyphenyl)-4'-oxo-3',4'-dihydro-1'H-spiro[cyclohexane-1,2'-quinazolin]-4-yl)carbamate)

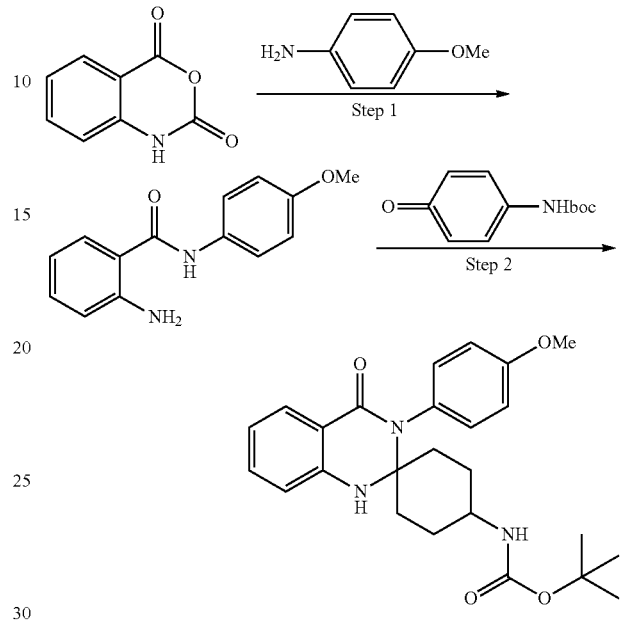

Step 1: Prepared following the same procedure as example 1, step 1.

Step 2: Prepared following the same procedure as example 4, step 2 to give title compound tert-butyl (3'-(4-methoxyphenyl)-4'-oxo-3',4'-dihydro-1'H-spiro[cyclohexane-1,2'-quinazolin]-4-yl)carbamate; LCMS (ESI) 438 (M+H); $^1$H NMR (CHLOROFORM-d) δ: 7.98 (d, J=6.9 Hz, 1H), 7.33-7.39 (m, 1H), 7.11 (d, J=8.7 Hz, 2H), 6.90-6.98 (m, 3H), 6.77 (d, J=8.0 Hz, 1H), 4.55 (s, 1H), 4.40 (br.s., 1H), 3.84 (s, 2H), 3.27 (br.s., 1H), 2.17 (d, J=12.2 Hz, 2H), 1.92 (d, J=12.4 Hz, 2H), 1.58-1.77 (m, 2H), 1.42 (s, 9H), 1.36 (d, J=14.4 Hz, 2H).

Example 26

Synthesis of Compound 125 (4-Bromo-2-hydroxy-N-(4-trifluoromethoxy-phenyl)-benzamide)

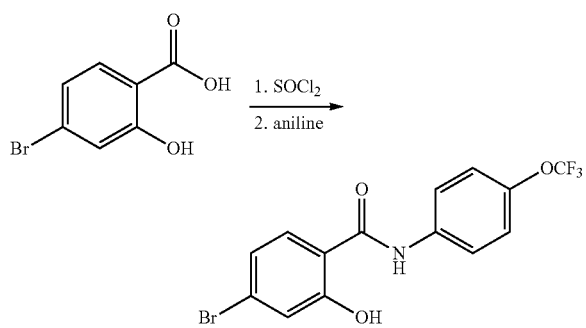

A round bottom flask was charged with the 2-amino-4-bromo-benzoic acid (868 mg, 4.0 mmol), thionyl chloride (10 mL) and catalytic dimethyl formamide (1 drop). The reaction was heated at 80° C. for 3 h, cooled and the solvent was evaporated under reduced pressure, followed by a second evaporation after adding a little toluene. The resulting oil was dissolved in dichloromethane (20 mL) and pyridine (1 mL, 12 mmol) and 4-trifluoromethoxy-phenylamine (709 mg, 4.0 mmol) were added. The reaction was stirred overnight at room temperature. It was added to a saturated aqueous solution NaHCO3 (50 mL), extracted with dichloromethane (3×50 mL), dried over anhydrous sodium sulfate and the solvent was evaporated under reduced pressure. The material was purified by chromatography using heptanes/ethyl acetate (0%-50%) as eluent to give title compound 4-bromo-2-hydroxy-N-(4-trifluoromethoxy-phenyl)-benzamide (800 mg, 53%).

Example 27

Synthesis of Compound 126 (1'-(3,4-difluorobenzyl)-2-(4-methoxyphenyl)-2,4-dihydro-1H-spiro[isoquinoline-3,4'-piperidin]-1-one)

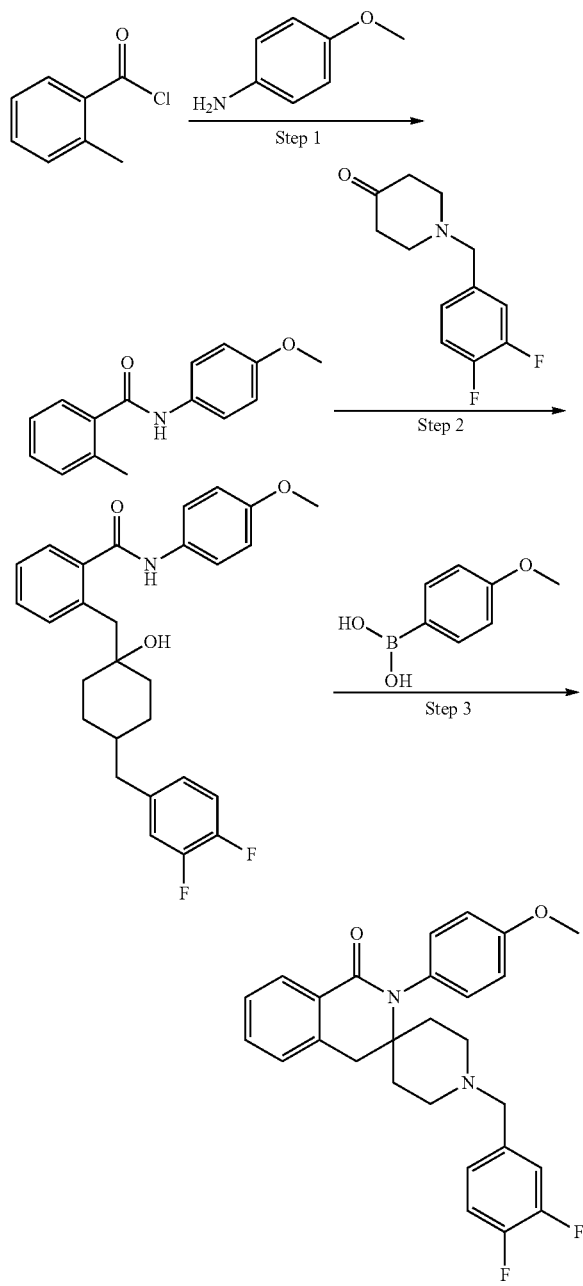

Step 1: To a solution of 4-methoxy-phenylamine (2.46 g, 20.0 mmol), dimethyl-pyridin-4-yl-amine (24.4 mg, 0.20 mmol) and triethylamine (6.07 g, 60.0 mmol) in dichloromethane (100 mL) was added 2-methyl-benzoyl chloride (3.09 g, 20.0 mmol). The reaction mixture was stirred 1 h at room temperature and poured into water. The phases were separated and the organic phase was washed with water, dried over anhydrous sodium sulfate, filtered and evaporated in vacuo to give N-(4-methoxy-phenyl)-2-methyl-benzamide (4.8 g; 99%). The material was used as is in the next step.

Step 2: To a solution of N-(4-methoxy-phenyl)-2-methyl-benzamide (724 mg, 3.00 mmol) in dry tetrahydrofuran (30 mL) under nitrogen was added dropwise a solution of n-butyllithium 1.6 M (4.1 mL, 6.60 mmol). The reaction was stirred for 30 min and 1-(3,4-difluoro-benzyl)-piperidin-4-one (676 mg, 3.00 mmol) was added as a solution in THF. The reaction was stirred 1 h and poured into a saturated solution of ammonium chloride, extracted with ethyl acetate, dried over anhydrous sodium sulfate, filtered and evaporated in vacuo. The residue was purified by chromatography using dichloromethane/dichloromethane/methanol/ammonia (95:4.5:0.5), gradient 0 to 100% as eluent to give 2-[1-(3,4-difluoro-benzyl)-4-hydroxy-piperidin-4-ylmethyl]-N-(4-methoxy-phenyl)-benzamide (520 mg; 37%); LCMS (ESI) 467 (M+H); $^1$H NMR (CHLOROFORM-d) δ: 8.25 (s, 1H), 7.62 (d, J=7.6 Hz, 1H), 7.51-7.57 (m, 2H), 7.43 (t, J=7.0 Hz, 1H), 7.34 (t, J=7.2 Hz, 1H), 7.16-7.28 (m, 3H), 7.00-7.13 (m, 2H), 6.89-6.95 (m, 2H), 4.44 (s, 1H), 3.82 (s, 3H), 2.97 (s, 2H), 2.64 (d, J=11.3 Hz, 2H), 2.39 (t, J=10.4 Hz, 2H), 1.74-1.84 (m, 2H), 1.66-1.74 (m, 2H).

Step 3: A mixture of 2-[1-(3,4-difluoro-benzyl)-4-hydroxy-piperidin-4-ylmethyl]-N-(4-methoxy-phenyl)-benzamide (467 mg, 1.00 mmol) and polyphosphoric acid (100 g, 1021 mmol) was heated at 85° C. for 1 h. The reaction was added to a 15% aqueous solution of sodium hydroxide and extracted with ethyl acetate. The combined organic phase was washed with water, dried over anhydrous sodium sulfate, filtered and evaporated in vacuo. The residue was purified by chromatography using heptane/ethyl acetate, (40%-80%) as eluent to give title compound 1'-(3,4-difluorobenzyl)-2-(4-methoxyphenyl)-2,4-dihydro-1H-spiro[isoquinoline-3,4'-piperidin]-1-one (244 mg; 54%); LCMS (ESI) 449 (M+H); $^1$H NMR (CHLOROFORM-d) δ: 8.26 (d, J=7.7 Hz, 1H), 7.38-7.44 (m, 1H), 7.28-7.36 (m, 2H), 7.03-7.19 (m, 3H), 6.94-7.00 (m, 1H), 6.89 (d, J=8.9 Hz, 2H), 3.86 (s, 3H), 3.39 (s, 2H), 2.96 (s, 2H), 2.49-2.56 (m, 2H), 2.26-2.35 (m, 2H), 1.88 (d, J=12.8 Hz, 2H), 1.65-1.75 (m, 2H).

The following compounds were synthesized in an analogous manner:

Compound 127 (1'-(3,4-difluorobenzyl)-6-fluoro-2-(4-(trifluoromethoxy)phenyl)-2,4-dihydro-1H-spiro[isoquinoline-3,4'-piperidin]-1-one); LCMS (ESI) 521 (M+H); $^1$H NMR (CHLOROFORM-d) δ: 8.27 (dd, J=8.7, 5.8 Hz, 1H), 7.01-7.22 (m, 7H), 6.87-6.97 (m, 2H), 3.29 (s, 2H), 2.95 (s, 2H), 2.75 (t, J=6.1 Hz, 1H), 2.45-2.54 (m, 2H), 2.11 (t, J=10.5 Hz, 2H), 1.83 (d, J=12.5 Hz, 2H), 1.63-1.73 (m, 2H)

TABLE 1

| Compound No. | LC/MS RT (min) | LC/MS m/z [M + H] | hrmGluR4/HEK293T-hmGluR4 (EC$_{50}$) A > 10 μM B = 1-10 μM C < 1 μM |
|---|---|---|---|
| 1 | | | C |
| 2 | 1.70 | 552 | C |
| 3 | | | C |
| 4 | | | C |
| 5 | 1.28 | 544 | C |

TABLE 1-continued

| Compound No. | LC/MS RT (min) | LC/MS m/z [M + H] | hrmGluR4/HEK293T-hmGluR4 ($EC_{50}$) A > 10 μM B = 1-10 μM C < 1 μM |
|---|---|---|---|
| 6 | 1.44 | 570 | C |
| 7 | 1.26 | 546 | C |
| 8 | 1.45 | 596 | C |
| 9 | 1.51 | 582 | C |
| 10 | 1.56 | 570 | C |
| 11 | 1.19 | 516 | C |
| 12 | 1.41 | 625 | C |
| 13 | 3.63 | 482 | C |
| 14 | 1.10 | 533 | C |
| 15 | 0.90 | 472 | C |
| 16 | 1.48 | 572 | C |
| 17 | 1.47 | 528 | C |
| 18 | 2.04 | 546 | C |
| 19 | | | C |
| 20 | 0.73 | 527 | C |
| 21 | 1.59 | 589 | C |
| 22 | 1.53 | 612 | C |
| 23 | | | C |
| 24 | 1.53 | 546 | C |
| 25 | 1.26 | 532 | C |
| 26 | 1.24 | 510 | C |
| 27 | 1.63 | 597 | C |
| 28 | 1.54 | 546 | C |
| 29 | 1.48 | 576 | C |
| 30 | 2.16 | 560 | C |
| 31 | 1.57 | 590 | C |
| 32 | 1.38 | 584 | C |
| 33 | | | C |
| 34 | | | C |
| 35 | 1.02 | 444 | C |
| 36 | 1.35 | 562 | C |
| 37 | 1.53 | 572 | C |
| 38 | 3.93 | 482 | C |
| 39 | 1.20 | 480 | C |
| 40 | 0.87 | 527 | C |
| 41 | 1.29 | 532 | C |
| 42 | 1.43 | 561 | C |
| 43 | 2.20 | 631 | C |
| 44 | 1.55 | 414 | C |
| 45 | 1.04 | 533 | C |
| 46 | 2.01 | 630 | C |
| 47 | 2.04 | 597 | C |
| 48 | 1.30 | 574 | C |
| 49 | 1.18 | 562 | C |
| 50 | 1.39 | 420 | C |
| 51 | 1.55 | 516 | C |
| 52 | 1.37 | 566 | C |
| 53 | 2.07 | 544 | C |
| 54 | 1.44 | 482 | C |
| 55 | 3.94 | 498 | C |
| 56 | 1.46 | 454 | C |
| 57 | 2.04 | 597 | C |
| 58 | 1.60 | 602 | C |
| 59 | 1.35 | 484 | C |
| 60 | | | C |
| 61 | 1.16 | 524 | C |
| 62 | 3.80 | 482 | C |
| 63 | | | C |
| 64 | | | C |
| 65 | 1.76 | 470 | C |
| 66 | 1.45 | 482 | B |
| 67 | 3.80 | 498 | B |
| 68 | 1.11 | 462 | B |
| 69 | 1.27 | 522 | B |
| 70 | 1.89 | 492 | B |
| 71 | 1.07 | 496 | B |
| 72 | 0.93 | 400 | B |
| 73 | | | B |
| 74 | 0.89 | 627 | B |
| 75 | 3.55 | 473 | B |
| 76 | | | B |
| 77 | 1.27 | 546 | B |
| 78 | 2.09 | 562 | B |
| 79 | 1.30 | 529 | B |
| 80 | 1.18 | 450 | B |
| 81 | 1.64 | 464 | B |
| 82 | 1.78 | 490 | B |
| 83 | | | B |
| 84 | 0.93 | 404 | B |
| 85 | 1.34 | 420 | B |
| 86 | 1.42 | 436 | B |
| 87 | 1.90 | 544 | B |
| 88 | 1.72 | 438 | B |
| 89 | 0.95 | 400 | B |
| 90 | 1.39 | 436 | B |
| 91 | | | B |
| 92 | 0.77 | 386 | B |
| 93 | 0.95 | 404 | B |
| 94 | 0.97 | 400 | B |
| 95 | 1.41 | 422 | B |
| 96 | 1.33 | 482 | B |
| 97 | 1.54 | 547 | B |
| 98 | 1.32 | 426 | B |
| 99 | 1.38 | 606 | B |
| 100 | 1.07 | 469 | B |
| 101 | 0.84 | 404 | B |
| 102 | 1.96 | 616 | B |
| 103 | 1.44 | 549 | B |
| 104 | 3.53 | 448 | B |
| 105 | 1.29 | 442 | B |
| 106 | 1.34 | 512 | B |
| 107 | 2.22 | 649 | C |
| 108 | 1.46 | 529 | B |
| 109 | 1.09 | 428 | B |
| 110 | 2.14 | 632 | B |
| 111 | 3.34 | 448 | B |
| 112 | 1.08 | 414 | B |
| 113 | 1.54 | 550 | B |
| 114 | 0.73 | 432 | B |
| 115 | 3.59 | 482 | B |
| 116 | 2.99 | 439 | B |
| 117 | 0.60 | 574 | B |
| 118 | 1.42 | 547 | B |
| 119 | 1.60 | 440 | B |
| 120 | 1.45 | 549 | B |
| 121 | 1.59 | 578 | B |
| 122 | 0.93 | 466 | B |
| 123 | 3.95 | 482 | B |
| 124 | 3.85 | 482 | B |
| 125 | | | C |
| 126 | 1.12 | 449 | B |
| 127 | 1.61 | 521 | B |

II. Biological Assays

HEK-293 mGluR4 Cells cAMP Assay with EC20 L-Glutamate

Using mGluR4 suspension cell format, 10 μM Forskolin (final conc.) used to induce the production of cAMP.

Test the positive allosteric activity of the compounds of the invention at $EC_{20}$ (2.3 μM for mGluR4 and 4.3 μM for mGluR6) L-Glutamate, cAMP dymanic2 kit is intended for the direct quantitative determination of cAMP and its principle is based on HTRF technology.

Reagents:
Cells: HEK293T mGluR4 cells from Multispan, cat# C1191a lot# C1191a-040910
Culture Media: DMEM+GlutaMAX1+10% dialyzed FBS, 100 mM Sodium Pyruvate, 1 ug/ml puromycin.
Glutamine Starvation Media: DMEM without GlutaMax for plating the cells (glutamine starvation overnight). DMEM high Glucose, without phenol red, glutamine, or sodium pyruvate+10% dialyzed FBS, 100 mM Sodium Pyruvate, 1 ug/ml puromycin, 10 mM Hepes.

Hanks' balanced Salt Solution, HBSS from Invitrogen

Greiner 384 well white low volume high base plate (784075)

cAMP dynamic2 from Cisbio Bioassays

Glutamate: L-Glutamaic acid, monosodium salt, Monohydrate, 98%, from Sigma-Aldrich Cell Preparation: split cells at 80%-90% confluence. The following day, rinse the cells with DMEM without GlutaMax and change to Glutamine Starvation Media. Incubate overnight.

Assay:

Prepare compound plate: Perform compound serial dilution (uses Matrix 4341 plate), using the Bravo liquid handling platform protocol (compound serial dilution) which adds DMSO to columns 1-24 (except cols. 3 and 13). Serial dilute compounds located in columns 3 and 13 at a 1:3 ratio; 10 points (10 ul of 3 mM compound into 20 ul DMSO). Use the Bravo liquid handling platform to transfer 1 ul from the serial dilution plate into Matrix 4314 plate to create stamp plates.

Prepare Compound Dilution Buffer:

Dilute 20 mM Forskolin (in DMSO) stock solution in HBSS buffer to make a 20 uM solution (forskolin buffer; 2× solution). To the forskolin buffer, add glutamate to a concentration of 8 uM (compound dilution buffer; 2× EC20 glutamate and forskolin).

Using a multidrop, add 50 ul/well of compound dilution buffer to columns 1-22 of the 2 ul compound stamp plate. Columns 23 and 24 receive forskolin buffer containing 400 uM glutamate (EC100 glutamate; 2× solution). Columns 1 and 2 receive compound dilution buffer containing EC20 glutamate, which is the basal control.

Add a glutamate dose response to row P of compound plate. Prepare the dose response by serial diluting glutamate at a 1:3 ratio in forskolin buffer starting at 2 mM glutamate (2×). Dilute the glutamate 9 times and transfer to compound plate.

Prepare Cell Plates:

Harvest cells: Rinse cells with pre-warmed HBSS-10 mM HEPES (without Ca Mg) and dissociate the cells from the flask with versene. Centrifuge the cells, remove the supernatant and suspend in pre-warmed HBSS+10 mM Hepes. Count the cells and centrifuge. Remove the supernatant and suspend the cells in HBSS+Hepes (with Ca Mg) at a density of 400,000 cells/ml.

Perform Assay:

Dispense 5 ul from the diluted compound plate into Greiner low volume cell plate using the Bravo liquid handling platform. Using a Multidrop with the small tubing cassette, dispense 5 ul of cells (2000 cells/well) onto the compounds contained in the low volume plates. Incubate the cells at 37° C., 5% $CO_2$ for 30 minutes in the incubator.

Assay for cAMP:

Prepare cAMP-d2 and anti-cAMP-Crytate according to the instructions for the two step assay (see Cisbio manual) and add 10 ul of the mixed reagent to each well of the assay plate using the Multidrop. Incubate at room temperature for 60 minutes and read on the Envision plate reader using the mGluR low volume cAMP HTRF 384 well protocol. The readout is the calculated fluoresence ratio (665 nM/615 nM*10000).

The measured half maximal effective concentration ($EC_{50}$) of the compounds of the invention is displayed in table 1.

The invention claimed is:

1. A compound of formula (I)

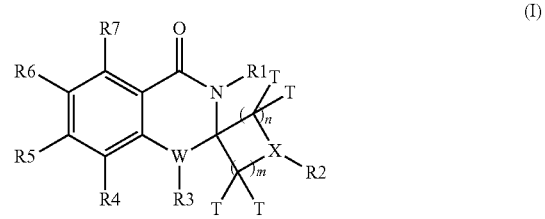

wherein:

W denotes N, O or CH,

X denotes N or CH;

R1 denotes cycloalkyl, cycloalkylalkyl, heterocyclyl, aryl, arylalkyl, heteroaryl, heteroarylalkyl, which can optionally be substituted by one or more identical or different substituents T;

R2 denotes, $(NY)_p$-cycloalkyl, $(NY)_p$-cycloalkylalkyl, $(NY)_p$-heterocyclyl, $(NY)_p$-heterocyclylalkyl, $(NY)_p$-aryl, $(NY)_p$-arylalkyl, $(NY)_p$-heteroaryl, $(NY)_p$-heteroarylalkyl, $(NY)_p$—C(O)-alkyl, $(NY)_p$—C(O)-cycloalkyl, $(NY)_p$—C(O)-alkyl-cycloalkyl, $(NY)_p$—C(O)-heterocyclyl, $(NY)_p$—C(O)-alkyl-heterocyclyl, $(NY)_p$—C(O)-aryl, $(NY)_p$—C(O)-alkyl-aryl, $(NY)_p$—C(O)-heteroaryl, $(NY)_p$—C(O)-alkyl-heteroaryl, $(NY)_p$—C(O)O-cycloalkyl, $(NY)_p$—C(O)O-alkyl-cycloalkyl, $(NY)_p$—C(O)O-heterocyclyl, $(NY)_p$—C(O)O-alkyl-heterocyclyl, $(NY)_p$—C(O)O-aryl, $(NY)_p$—C(O)O-alkyl-aryl, $(NY)_p$—C(O)O-heteroaryl, $(NY)_p$—C(O)O-alkyl-heteroaryl, $(NY)_p$—C(O)NH-alkyl, $(NY)_p$—C(O)NH-cycloalkyl, $(NY)_p$—C(O)NH-alkyl-cycloalkyl, $(NY)_p$—C(O)NH-heterocyclyl, $(NY)_p$—C(O)NH-alkyl-heterocyclyl, $(NY)_p$—C(O)NH-aryl, $(NY)_p$—C(O)NH-alkyl-aryl, $(NY)_p$—C(O)NH-heteroaryl, $(NY)_p$—C(O)NH-alkyl-heteroaryl, $(NY)_p$—S(O)$_2$-alkyl, $(NY)_p$—S(O)$_2$-cycloalkyl, $(NY)_p$—S(O)$_2$-alkyl-cycloalkyl, $(NY)_p$—S(O)$_2$-heterocyclyl, $(NY)_p$—S(O)$_2$-alkyl-heterocyclyl, $(NY)_p$—S(O)$_2$-aryl, $(NY)_p$—S(O)$_2$-alkyl-aryl, $(NY)_p$—S(O)$_2$-heteroaryl, $(NY)_p$—S(O)$_2$-alkyl-heteroaryl, which can optionally be substituted by one or more identical or different substituents T;

R3 if W is N or CH, R3 denotes H or alkyl, cycloalkyl, cycloalkylalkyl, heterocyclyl, heterocyclylalkyl, aryl, arylalkyl, heteroaryl, heteroarylalkyl; which can optionally be substituted by one or more identical or different substituents T;

if W is O, R3 is absent;

R4, R5, R6, R7 independently from each other denote H, alkyl, aryl, heteroaryl, cycloalkyl, heterocyclyl, halogen, F, Cl, Br, I, OH, CN, $NO_2$, NYY, $CF_3$, $OCF_3$, O-alkyl-heterocyclyl, O-alkyl-aryl, O-alkyl-heteroaryl, O-alkyl-NYY, O-alkyl-O-alkyl, C(O)OY, C(O)NY-alkyl-NYY, C(O)NYY, C(O)-alkyl, C(O)-heterocyclyl, $S(O)_2$—Y;

whereby alkyl, heterocyclyl, aryl, heteroaryl can optionally be substituted by one or more identical or different substituents T;

T denotes independently from each other H, alkyl, halogen, F, Cl, Br, I, OH, CN, $NO_2$, NYY, $CF_3$, $OCF_3$, O-alkyl, O-alkyl-heterocyclyl, alkyl-NYY, O-alkyl-aryl, O-alkyl-heteroaryl, O-alkyl-NYY, O-alkyl-O-alkyl, C(O)OY, C(O)NY-alkyl-NYY, C(O)NYY, $S(O)_2$—Y, S-alkyl; or two adjacent substituents T can also form together with the atoms to which they are attached to cycloalkyl or heterocyclyl;

Y denotes independently from each other H, alkyl, cycloalkyl, cycloalkylalkyl, aryl, arylalkyl, heteroaryl, heteroarylalkyl, alkyl-O-alkyl;

n, m independently from each other denote 1 or 2;

p denotes independently from each other 0 if X is N or denotes independently from each other 1 if X is CH;

and the physiologically acceptable salts, solvates, tautomers and stereoisomers thereof, including mixtures thereof in all ratios.

2. A compound according to claim 1, wherein
n, m both denote 2;
and the physiologically acceptable salts, solvates, tautomers and stereoisomers thereof, including mixtures thereof in all ratios.

3. A compound according to claim 1, wherein
n, m both denote 1;
and the physiologically acceptable salts, solvates, tautomers and stereoisomers thereof, including mixtures thereof in all ratios.

4. A compound according to claim 1, wherein
X denotes N;
p denotes 0;
and the physiologically acceptable salts, solvates, tautomers and stereoisomers thereof, including mixtures thereof in all ratios.

5. A compound according to claim 1, wherein
X denotes CH;
p denotes 1;
and the physiologically acceptable salts, solvates, tautomers and stereoisomers thereof, including mixtures thereof in all ratios.

6. A Compound according to claim 1, wherein
R1 denotes cycloalkyl, aryl, or heteroaryl; which can optionally be substituted by one or more identical or different substituents T;
and the physiologically acceptable salts, solvates, tautomers and stereoisomers thereof, including mixtures thereof in all ratios.

7. A compound according to claim 6, wherein
R1 denotes methoxy-ethyl, 1-methoxy-ethan-2-yl, methoxy-propyl, 1-methoxy-propan-3-yl, cyclopropyl, phenyl, methyl-phenyl, 1-methyl-phen-4-yl, 1-methyl-phen-3-yl, hydroxy-phenyl, 1-hydroxy-phen-2-yl, 1-hydroxy-phen-3-yl, 1-hydroxy-phen-4-yl, methoxy-phenyl, 1-methoxy-phen-4-yl, 1-methoxy-phen-3-yl, 1-methoxy-phen-2-yl, fluoro-phenyl, 1-fluoro-phen-4-yl, fluoro-methoxy-phenyl, bromo-phenyl, 1-bromo-phen-4-yl, cyano-phenyl, 1-cyano-phen-4-yl, 1-methoxy-2-fluoro-phen-4-yl, pyridyl, pyridin-3-yl, methoxy-pyridyl, 2-methoxy-pyridin-5-yl, thiazolyl, thiazol-2-yl, benzimidazolyl, benzimidazol-2-yl, pyrazolyl, pyrazol-3-yl, methyl-pyrazolyl, 1-methyl-3-pyrazol-3-yl, methyl-benzofuranyl, 2-methyl-benzofuran-5-yl, dimethyl-aminoethyl, 1,1-dimethylaminoethan-2-yl, dimethyl-aminopropyl, 1,1-dimethylaminopropan-3-yl, dimethyl-aminoethoxy-phenyl, 1,1-dimethyl-aminoethoxy-phen-4-yl, methoxy-ethoxy-phenyl, 2-methoxy-ethoxy-phen-4-yl, chloro-phenyl, 1-chloro-phen-4-yl, trifluoromethoxy-phenyl, 1-trifluoromethoxy-phen-4-yl, trifluoromethyl-phenyl, 1-trifluoromethyl-phen-4-yl, trifluoromethyl-chloro-phenyl, 1-trifluoromethyl-2-chloro-phen-4-yl, trifluoromethoxy-chloro-phenyl, 1-trifluoromethoxy-2-chloro-phen-4-yl, methyl-sulfonyl-phenyl, 1-methyl-sulfonyl-phen-4-yl, methyl-thio-phenyl, methyl-thio-phen-4-yl;

and the physiologically acceptable salts, solvates, tautomers and stereoisomers thereof, including mixtures thereof in all ratios.

8. A compound according to claim 6, wherein said cycloalkyl is cyclopropyl.

9. A compound according to claim 6 wherein said aryl is phenyl.

10. A compound according to claim 6 wherein said heteroaryl is pyridyl, thiazolyl, benzimidazole or benzofuranyl.

11. A compound according to claim 1, wherein
R2 denotes methyl, ethyl, propenyl, cyclopropylmethyl, phenylmethyl, phenylethyl, phenylpropyl, trifluoromethoxy-phenylmethyl, chloro-phenylmethyl, chloro-phenylethyl, difluoro-phenylmethyl, cyano-phenylmethyl, hydroxy-phenylmethyl, pyridylmethyl, fluoro-pyridylmethyl, fluoro-phenylmethyl, fluoro-phenylethyl, dimethyl-phenylmethyl, methyl-phenylmethyl, benzo[1,3]dioxole-methyl, methoxy-phenylmethyl, chloro-thiophenylmethyl, ethyl-phenylmethyl, dichloro-phenylmethyl, chloro-phenylethyl, chloro-phenylpropyl, difluoro-phenylethyl, methyl-pyrrolylmethyl, methyl-furanylmethyl, quinolinylmethyl, isoquinolinylmethyl, bromo-thiazolylmethyl, methyl-pyrazolylmethyl, difluoro-phenylpropyl, methyl-thiazolylmethyl, methyl-isooxazolylmethyl, [1,2,4]-oxadiazolylmethyl, methyl-imidazolylmethyl, imidazo-pyridylmethyl, fluoro-phenylmethyl, trifluoromethyl-phenylmethyl, nitro-phenylmethyl, phenylmethyloxy-phenylmethyl, naphthylmethyl, isobutyl-phenylmethyl, isopropyl-phenylmethyl, trifluoro-phenylmethyl, dichloro-phenyl-carbonyl, fluoro-phenyl-carbonyl, difluoro-phenyl-trifluoroethyl, fluoro-phenyl-trifluoroethyl, tert.-butyl-carbamate, difluoro-phenyl-methyl-amino, phenyl-methyl-amino, acetamide, trifluoro-acetamide, benzamide, phenylamino, methane-sulfonamide, benzene-sulfonamide, trifluoromethyl-benzene-sulfonamide, phenyl-urea, methyl-urea;

and the physiologically acceptable salts, solvates, tautomers and stereoisomers thereof, including mixtures thereof in all ratios.

12. A compound according to claim 1, which are selected from the group consisting of:

| Compound No. | Chemical Structure |
|---|---|
| 1 | 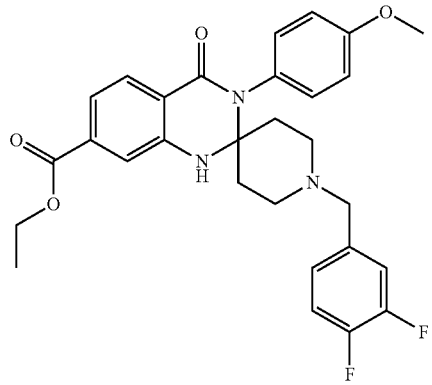 [SMILES: CCOC(=O)c1ccc2c(c1)NC1(CCN(Cc3ccc(F)c(F)c3)CC1)N(c1ccc(OC)cc1)C2=O] |
| 2 | 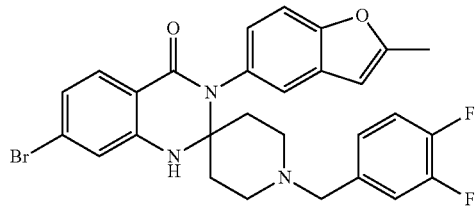 [SMILES: Cc1cc2cc(N3C(=O)c4ccc(Br)cc4NC34CCN(Cc3ccc(F)c(F)c3)CC4)ccc2o1] |
| 3 | 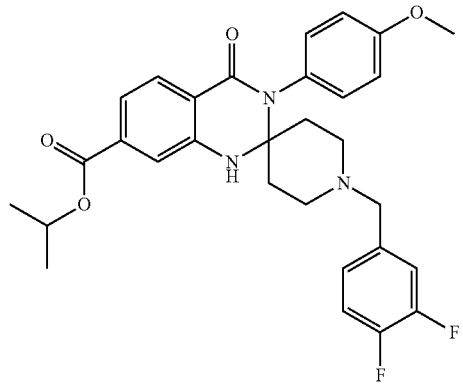 [SMILES: COc1ccc(N2C(=O)c3ccc(C(=O)OC(C)C)cc3NC23CCN(Cc2ccc(F)c(F)c2)CC3)cc1] |
| 4 | 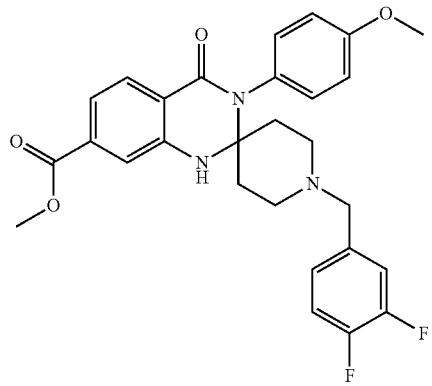 [SMILES: COC(=O)c1ccc2c(c1)NC1(CCN(Cc3ccc(F)c(F)c3)CC1)N(c1ccc(OC)cc1)C2=O] |

-continued
| Compound No. | Chemical Structure |
|---|---|
| 5 | 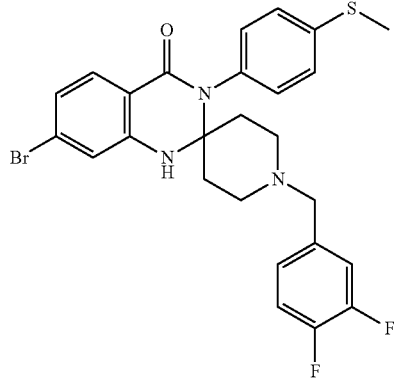 [SMILES: CSc1ccc(N2C(=O)c3ccc(Br)cc3NC23CCN(Cc2ccc(F)c(F)c2)CC3)cc1] |
| 6 | 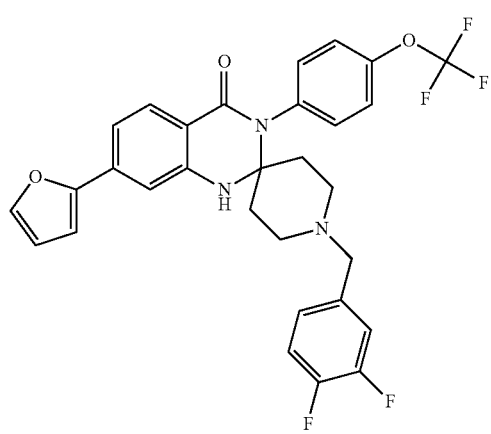 [SMILES: O=C1c2ccc(-c3ccco3)cc2NC2(CCN(Cc3ccc(F)c(F)c3)CC2)N1c1ccc(OC(F)(F)F)cc1] |
| 7 | 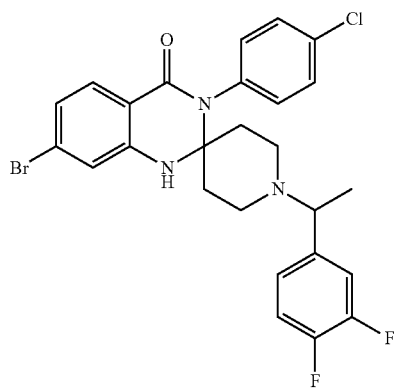 [SMILES: CC(c1ccc(F)c(F)c1)N1CCC2(CC1)Nc1cc(Br)ccc1C(=O)N2c1ccc(Cl)cc1] |

-continued
| Compound No. | Chemical Structure |
|---|---|
| 8 | 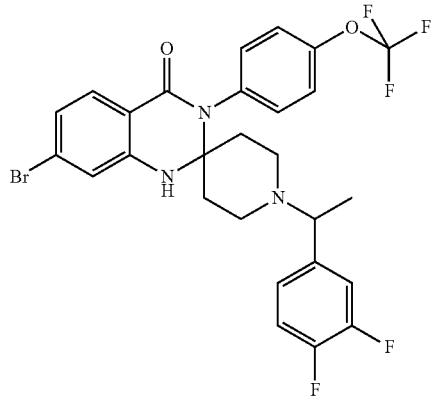 [SMILES: CC(c1ccc(F)c(F)c1)N1CCC2(CC1)Nc1cc(Br)ccc1C(=O)N2c1ccc(OC(F)(F)F)cc1] |
| 9 | 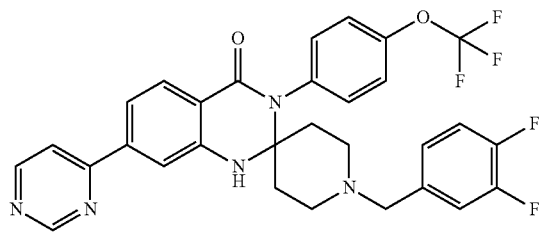 [SMILES: O=C1c2ccc(-c3ccncn3)cc2NC2(CCN(Cc3ccc(F)c(F)c3)CC2)N1c1ccc(OC(F)(F)F)cc1] |
| 10 | 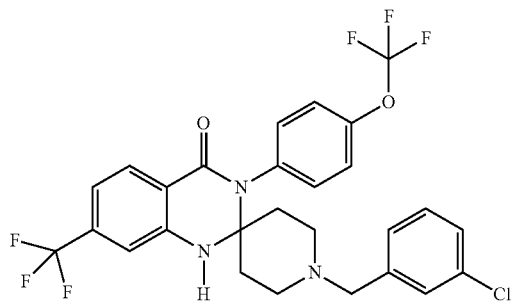 [SMILES: O=C1c2ccc(C(F)(F)F)cc2NC2(CCN(Cc3cccc(Cl)c3)CC2)N1c1ccc(OC(F)(F)F)cc1] |
| 11 | 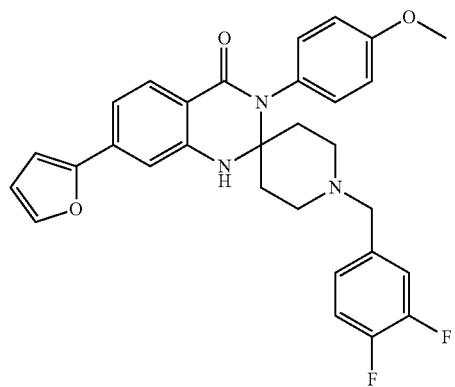 [SMILES: COc1ccc(N2C(=O)c3ccc(-c4ccco4)cc3NC23CCN(Cc2ccc(F)c(F)c2)CC3)cc1] |

-continued
| Compound No. | Chemical Structure |
|---|---|
| 12 | 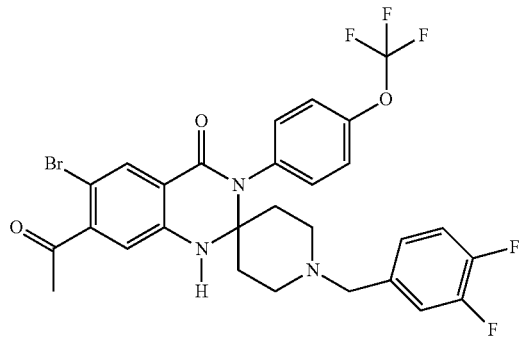 [SMILES: CC(=O)c1cc2c(cc1Br)C(=O)N(c1ccc(OC(F)(F)F)cc1)C1(CCN(Cc3ccc(F)c(F)c3)CC1)N2] |
| 13 | 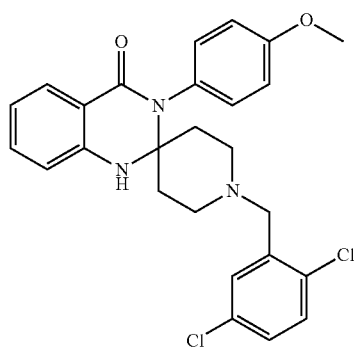 [SMILES: COc1ccc(N2C(=O)c3ccccc3NC23CCN(Cc2cc(Cl)ccc2Cl)CC3)cc1] |
| 14 | 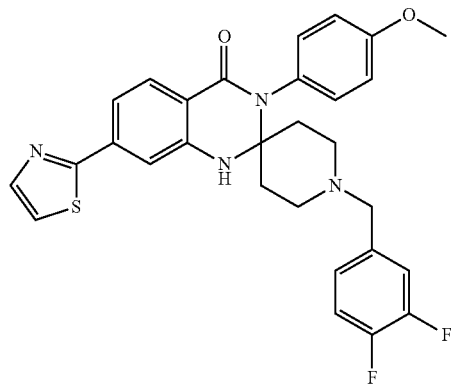 [SMILES: COc1ccc(N2C(=O)c3ccc(-c4nccs4)cc3NC23CCN(Cc2ccc(F)c(F)c2)CC3)cc1] |
| 15 | 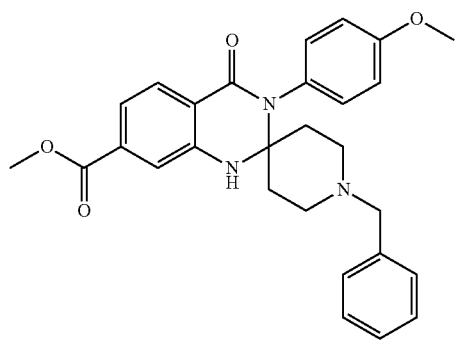 |

-continued
| Compound No. | Chemical Structure |
|---|---|
| 16 | 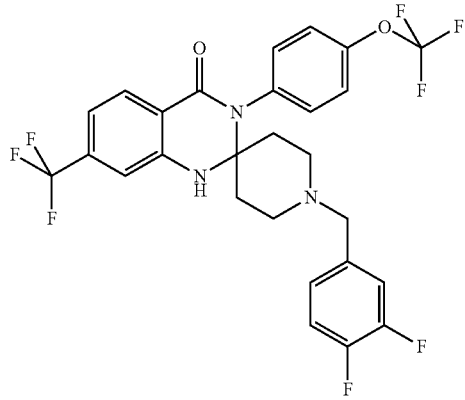 [SMILES: O=C1c2ccc(C(F)(F)F)cc2NC2(CCN(Cc3ccc(F)c(F)c3)CC2)N1c1ccc(OC(F)(F)F)cc1] |
| 17 | 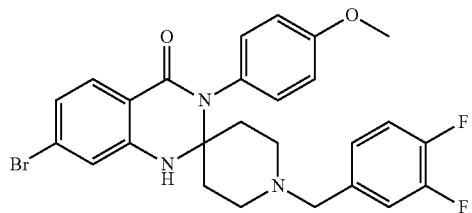 [SMILES: COc1ccc(N2C(=O)c3ccc(Br)cc3NC23CCN(Cc2ccc(F)c(F)c2)CC3)cc1] |
| 18 | 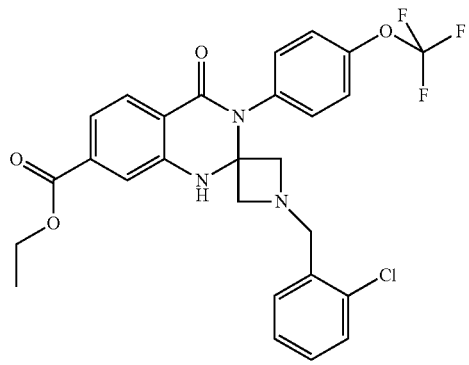 [SMILES: CCOC(=O)c1ccc2c(c1)NC1(CN(Cc3ccccc3Cl)C1)N(c1ccc(OC(F)(F)F)cc1)C2=O] |
| 19 | 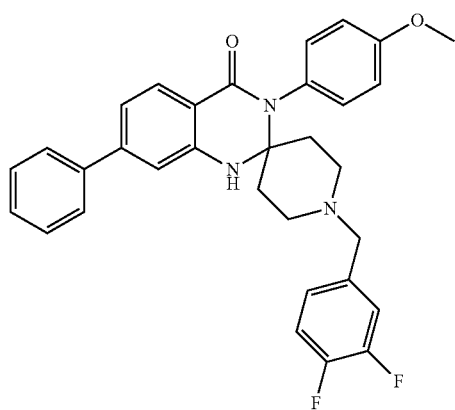 [SMILES: COc1ccc(N2C(=O)c3ccc(-c4ccccc4)cc3NC23CCN(Cc2ccc(F)c(F)c2)CC3)cc1] |

-continued
| Compound No. | Chemical Structure |
|---|---|
| 20 | 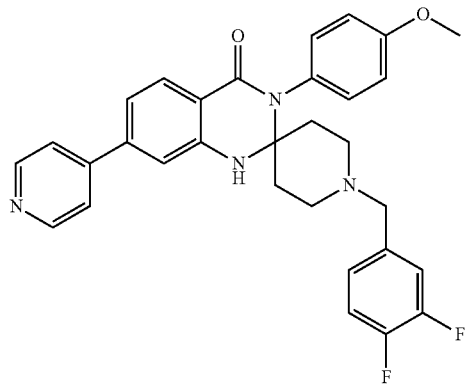 [SMILES: COc1ccc(N2C(=O)c3ccc(-c4ccncc4)cc3NC23CCN(Cc2ccc(F)c(F)c2)CC3)cc1] |
| 21 | 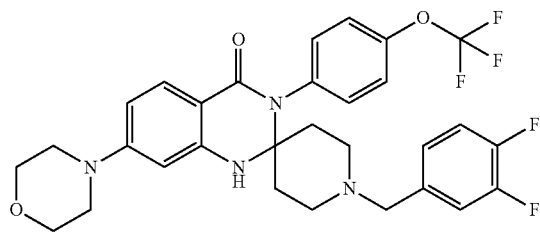 [SMILES: O=C1c2ccc(N3CCOCC3)cc2NC2(CCN(Cc3ccc(F)c(F)c3)CC2)N1c1ccc(OC(F)(F)F)cc1] |
| 22 | 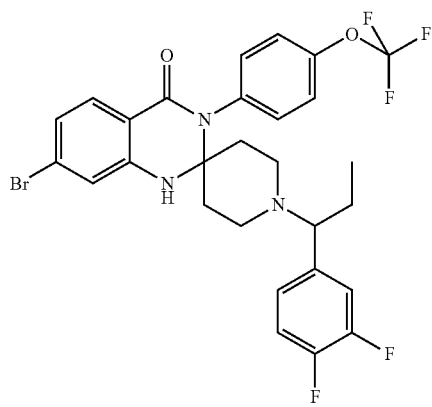 [SMILES: CCC(c1ccc(F)c(F)c1)N1CCC2(CC1)Nc1cc(Br)ccc1C(=O)N2c1ccc(OC(F)(F)F)cc1] |
| 23 | 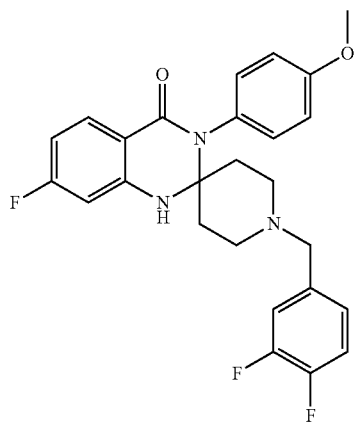 [SMILES: COc1ccc(N2C(=O)c3ccc(F)cc3NC23CCN(Cc2ccc(F)c(F)c2)CC3)cc1] |

-continued
| Compound No. | Chemical Structure |
|---|---|
| 24 | 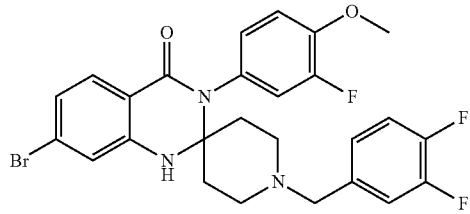 [SMILES: COc1ccc(N2C(=O)c3ccc(Br)cc3NC23CCN(Cc2ccc(F)c(F)c2)CC3)cc1F] |
| 25 | 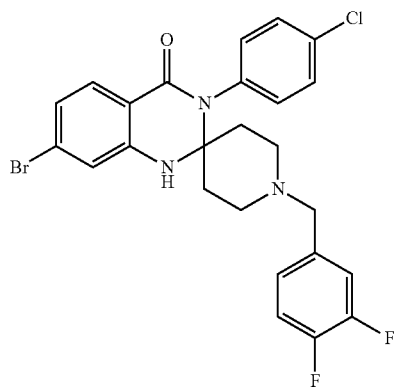 [SMILES: O=C1c2ccc(Br)cc2NC2(CCN(Cc3ccc(F)c(F)c3)CC2)N1c1ccc(Cl)cc1] |
| 26 | 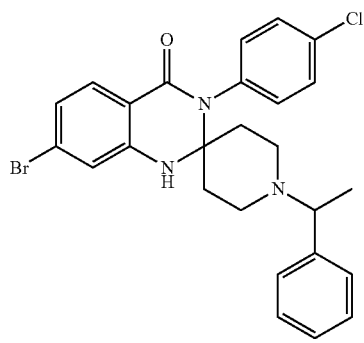 [SMILES: CC(c1ccccc1)N1CCC2(CC1)Nc1cc(Br)ccc1C(=O)N2c1ccc(Cl)cc1] |
| 27 | 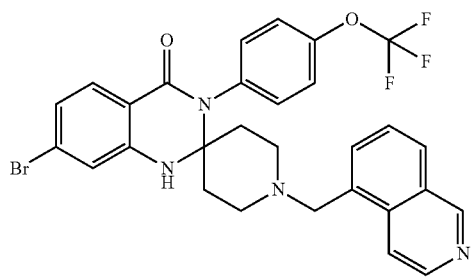 [SMILES: O=C1c2ccc(Br)cc2NC2(CCN(Cc3cccc4cnccc34)CC2)N1c1ccc(OC(F)(F)F)cc1] |
| 28 | 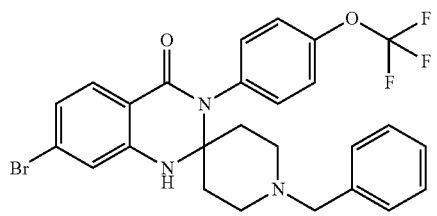 [SMILES: O=C1c2ccc(Br)cc2NC2(CCN(Cc3ccccc3)CC2)N1c1ccc(OC(F)(F)F)cc1] |

-continued
| Compound No. | Chemical Structure |
|---|---|
| 29 | 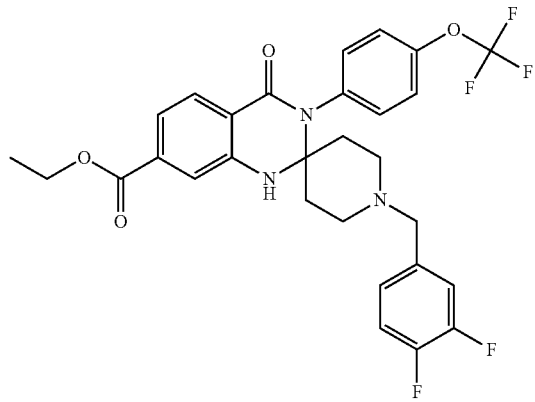 [SMILES: CCOC(=O)c1ccc2c(c1)NC1(CCN(Cc3ccc(F)c(F)c3)CC1)N(c1ccc(OC(F)(F)F)cc1)C2=O] |
| 30 | 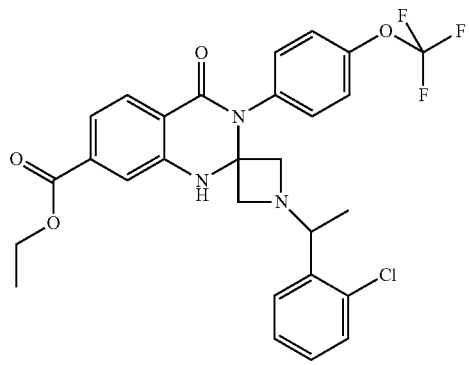 [SMILES: CCOC(=O)c1ccc2c(c1)NC1(CN(C(C)c3ccccc3Cl)C1)N(c1ccc(OC(F)(F)F)cc1)C2=O] |
| 31 | 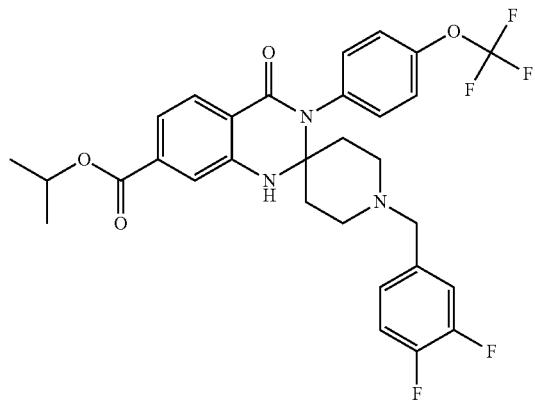 [SMILES: CC(C)OC(=O)c1ccc2c(c1)NC1(CCN(Cc3ccc(F)c(F)c3)CC1)N(c1ccc(OC(F)(F)F)cc1)C2=O] |
| 32 | 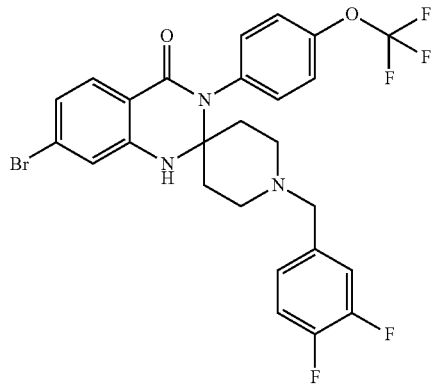 [SMILES: O=C1c2ccc(Br)cc2NC2(CCN(Cc3ccc(F)c(F)c3)CC2)N1c1ccc(OC(F)(F)F)cc1] |

-continued
| Compound No. | Chemical Structure |
|---|---|
| 33 | 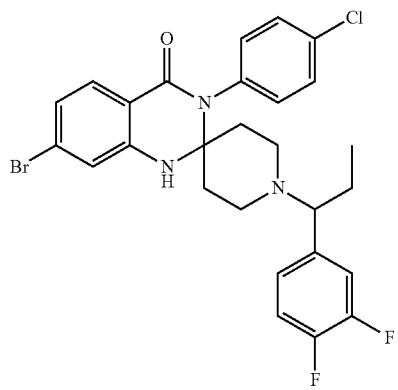 [SMILES: CCC(c1ccc(F)c(F)c1)N1CCC2(CC1)Nc1cc(Br)ccc1C(=O)N2c1ccc(Cl)cc1] |
| 34 | 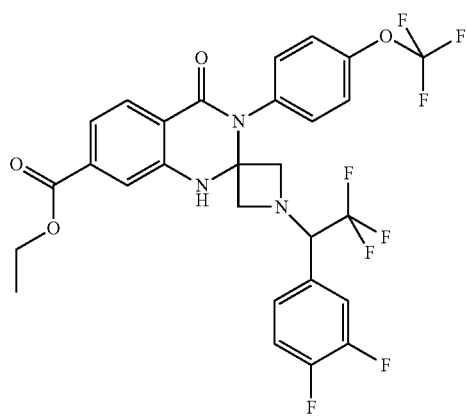 [SMILES: CCOC(=O)c1ccc2c(c1)NC1(CN(C(c3ccc(F)c(F)c3)C(F)(F)F)C1)N(c1ccc(OC(F)(F)F)cc1)C2=O] |
| 35 | 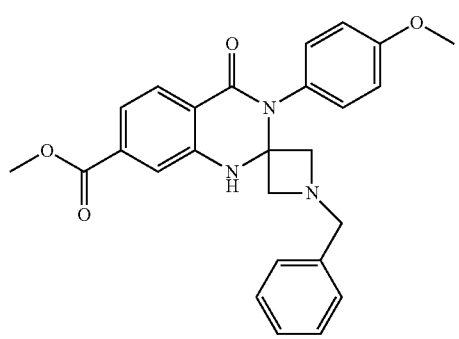 |
| 36 | 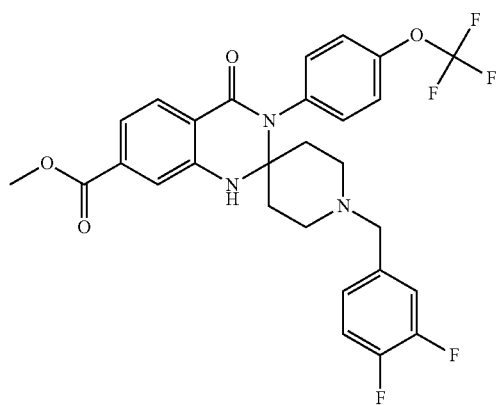 [SMILES: COC(=O)c1ccc2c(c1)NC1(CCN(Cc3ccc(F)c(F)c3)CC1)N(c1ccc(OC(F)(F)F)cc1)C2=O] |

-continued
| Compound No. | Chemical Structure |
|---|---|
| 37 | 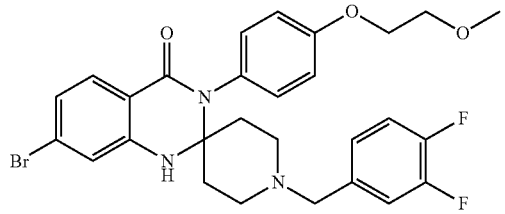 [SMILES: COCCOc1ccc(N2C(=O)c3ccc(Br)cc3NC23CCN(Cc2ccc(F)c(F)c2)CC3)cc1] |
| 38 | 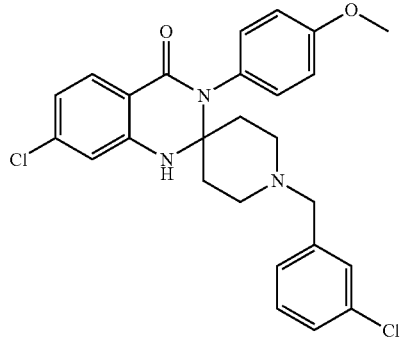 [SMILES: COc1ccc(N2C(=O)c3ccc(Cl)cc3NC23CCN(Cc2cccc(Cl)c2)CC3)cc1] |
| 39 | 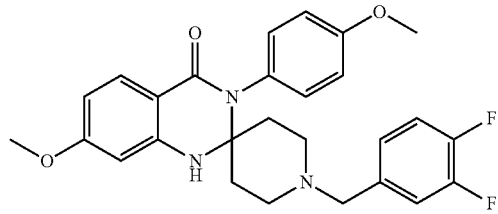 [SMILES: COc1ccc(N2C(=O)c3ccc(OC)cc3NC23CCN(Cc2ccc(F)c(F)c2)CC3)cc1] |
| 40 | 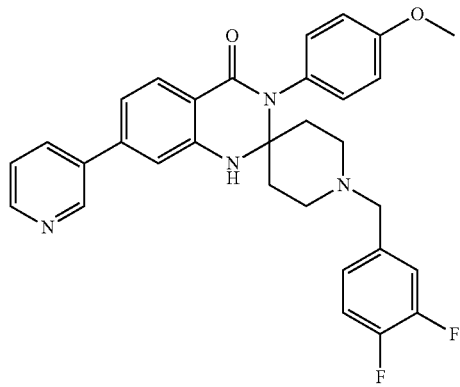 [SMILES: COc1ccc(N2C(=O)c3ccc(-c4cccnc4)cc3NC23CCN(Cc2ccc(F)c(F)c2)CC3)cc1] |
| 41 | 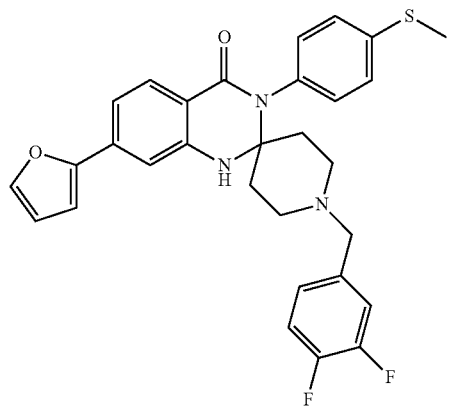 [SMILES: CSc1ccc(N2C(=O)c3ccc(-c4ccco4)cc3NC23CCN(Cc2ccc(F)c(F)c2)CC3)cc1] |

-continued
| Compound No. | Chemical Structure |
|---|---|
| 42 | 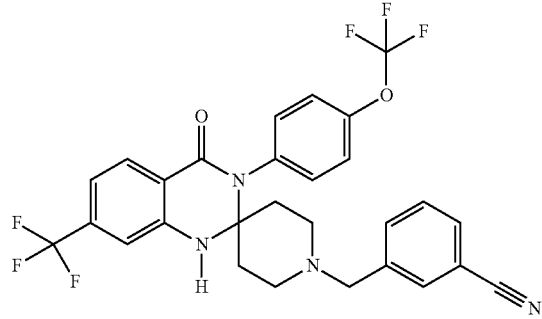 [SMILES: N#Cc1cccc(CN2CCC3(CC2)Nc2cc(C(F)(F)F)ccc2C(=O)N3c2ccc(OC(F)(F)F)cc2)c1] |
| 43 | 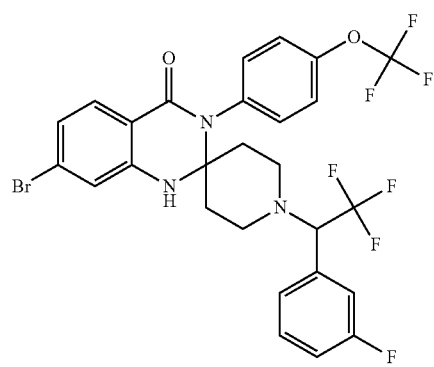 [SMILES: O=C1c2ccc(Br)cc2NC2(CCN(C(c3cccc(F)c3)C(F)(F)F)CC2)N1c1ccc(OC(F)(F)F)cc1] |
| 44 | 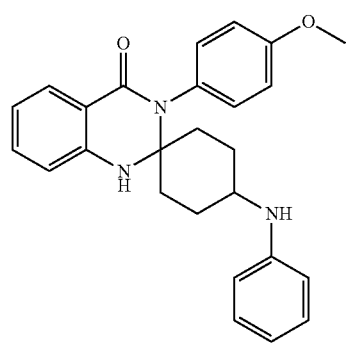 [SMILES: COc1ccc(N2C(=O)c3ccccc3NC23CCC(Nc2ccccc2)CC3)cc1] |
| 45 | 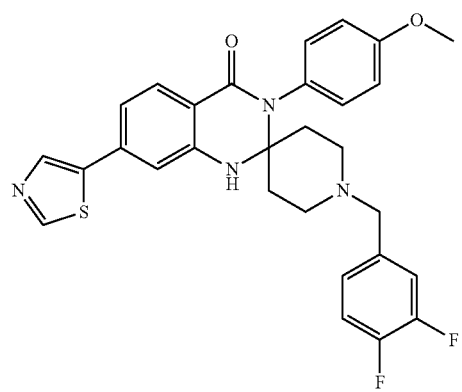 [SMILES: COc1ccc(N2C(=O)c3ccc(-c4cncs4)cc3NC23CCN(Cc2ccc(F)c(F)c2)CC3)cc1] |

-continued
| Compound No. | Chemical Structure |
|---|---|
| 46 | 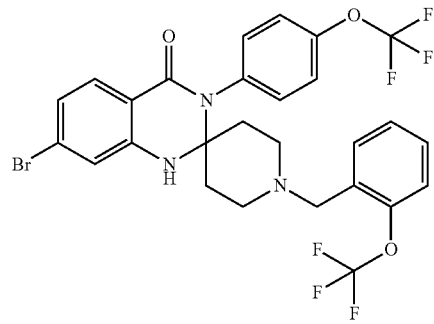 [SMILES: O=C1c2ccc(Br)cc2NC2(CCN(Cc3ccccc3OC(F)(F)F)CC2)N1c1ccc(OC(F)(F)F)cc1] |
| 47 | 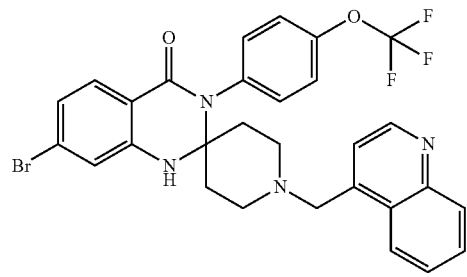 [SMILES: O=C1c2ccc(Br)cc2NC2(CCN(Cc3ccnc4ccccc34)CC2)N1c1ccc(OC(F)(F)F)cc1] |
| 48 | 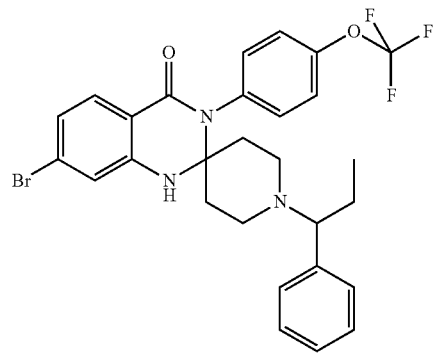 [SMILES: CCC(c1ccccc1)N1CCC2(CC1)Nc1cc(Br)ccc1C(=O)N2c1ccc(OC(F)(F)F)cc1] |
| 49 | 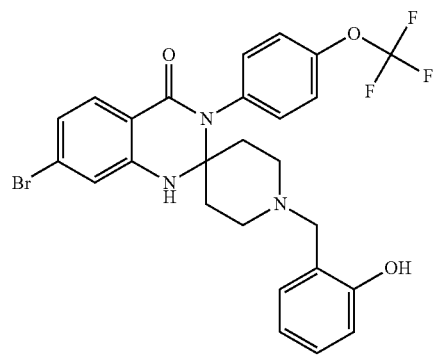 [SMILES: O=C1c2ccc(Br)cc2NC2(CCN(Cc3ccccc3O)CC2)N1c1ccc(OC(F)(F)F)cc1] |

-continued
| Compound No. | Chemical Structure |
|---|---|
| 50 | 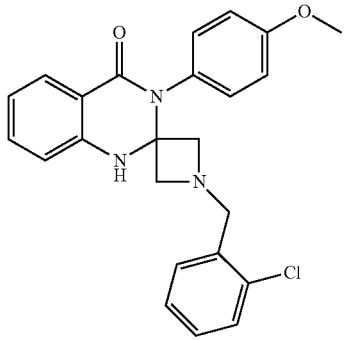 [SMILES: COc1ccc(N2C(=O)c3ccccc3NC23CN(Cc2ccccc2Cl)C3)cc1] |
| 51 | 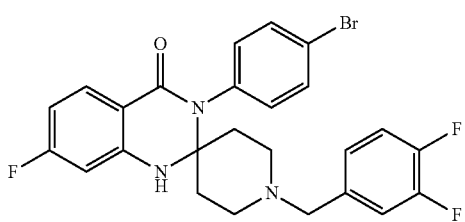 [SMILES: O=C1c2ccc(F)cc2NC2(CCN(Cc3ccc(F)c(F)c3)CC2)N1c1ccc(Br)cc1] |
| 52 | 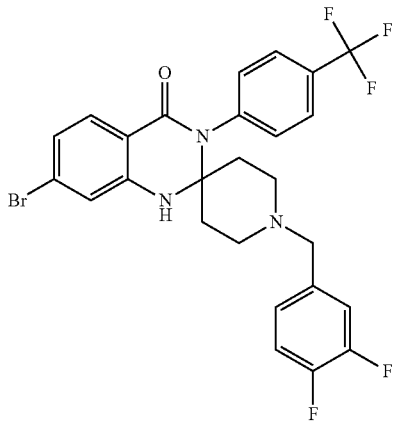 [SMILES: O=C1c2ccc(Br)cc2NC2(CCN(Cc3ccc(F)c(F)c3)CC2)N1c1ccc(C(F)(F)F)cc1] |
| 53 | 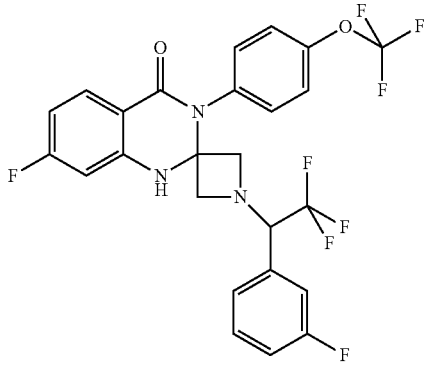 [SMILES: O=C1c2ccc(F)cc2NC2(CN(C(c3cccc(F)c3)C(F)(F)F)C2)N1c1ccc(OC(F)(F)F)cc1] |
| 54 | 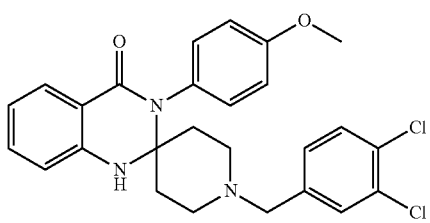 [SMILES: COc1ccc(N2C(=O)c3ccccc3NC23CCN(Cc2ccc(Cl)c(Cl)c2)CC3)cc1] |

| Compound No. | Chemical Structure |
|---|---|
| 55 | 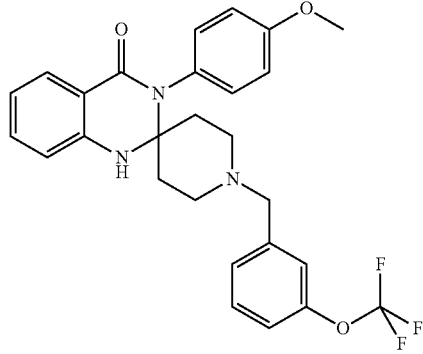 [SMILES: COc1ccc(N2C(=O)c3ccccc3NC23CCN(Cc2cccc(OC(F)(F)F)c2)CC3)cc1] |
| 56 | 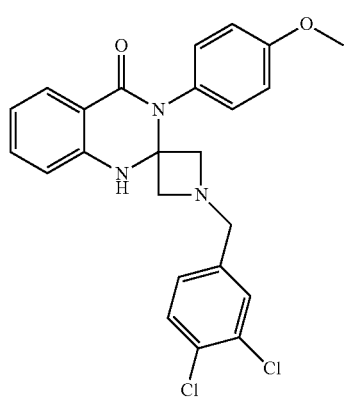 [SMILES: COc1ccc(N2C(=O)c3ccccc3NC23CN(Cc2ccc(Cl)c(Cl)c2)C3)cc1] |
| 57 | 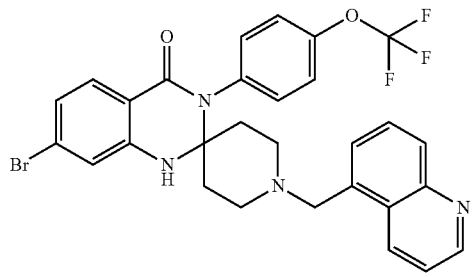 [SMILES: O=C1c2ccc(Br)cc2NC2(CCN(Cc3cccc4ncccc34)CC2)N1c1ccc(OC(F)(F)F)cc1] |
| 58 | 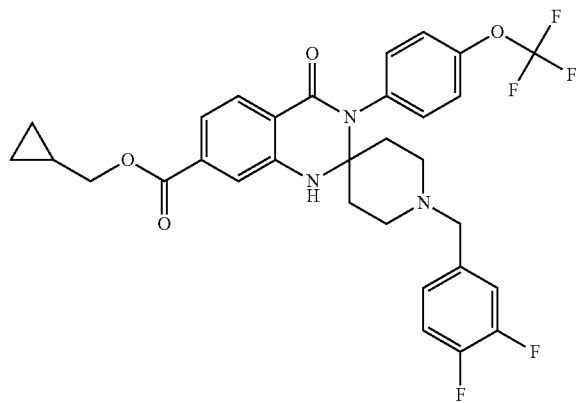 [SMILES: O=C(OCC1CC1)c1ccc2c(c1)NC1(CCN(Cc3ccc(F)c(F)c3)CC1)N(c1ccc(OC(F)(F)F)cc1)C2=O] |

-continued
| Compound No. | Chemical Structure |
|---|---|
| 59 | 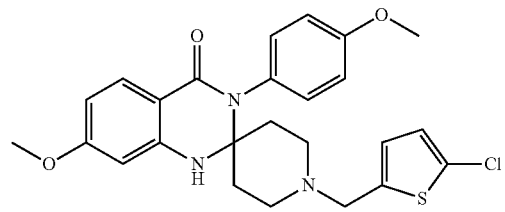 [SMILES: COc1ccc(N2C(=O)c3ccc(OC)cc3NC23CCN(Cc2ccc(Cl)s2)CC3)cc1] |
| 60 | 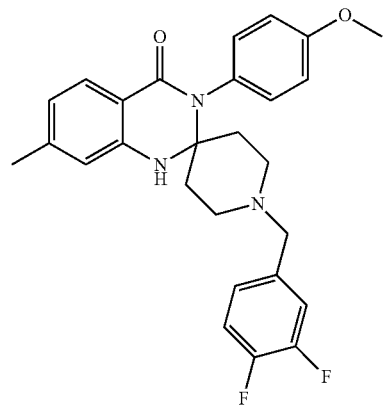 |
| 61 | 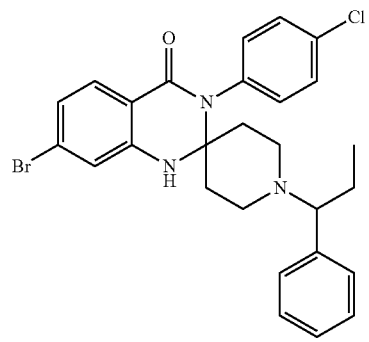 [SMILES: CCC(c1ccccc1)N1CCC2(CC1)Nc1cc(Br)ccc1C(=O)N2c1ccc(Cl)cc1] |
| 62 | 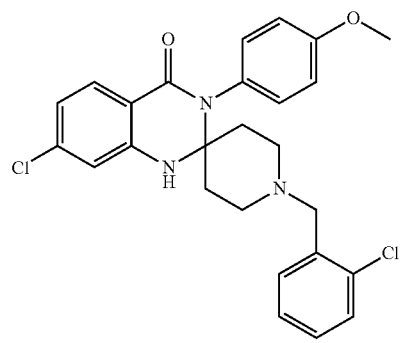 [SMILES: COc1ccc(N2C(=O)c3ccc(Cl)cc3NC23CCN(Cc2ccccc2Cl)CC3)cc1] |

| Compound No. | Chemical Structure |
|---|---|
| 63 | 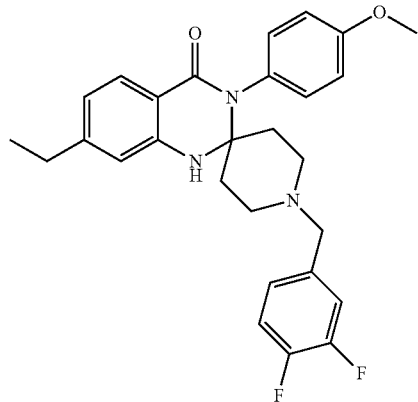 [SMILES: CCc1ccc2c(c1)NC1(CCN(Cc3ccc(F)c(F)c3)CC1)N(c1ccc(OC)cc1)C2=O] |
| 64 | 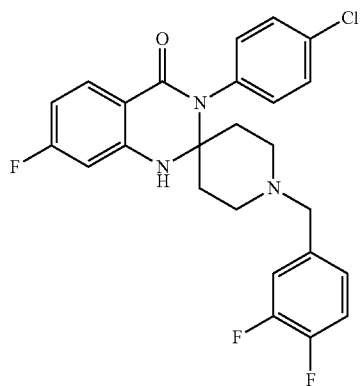 [SMILES: O=C1c2ccc(F)cc2NC2(CCN(Cc3ccc(F)c(F)c3)CC2)N1c1ccc(Cl)cc1] |
| 65 | 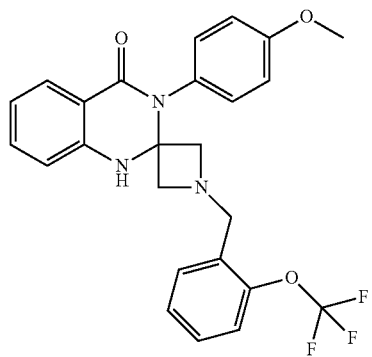 [SMILES: COc1ccc(N2C(=O)c3ccccc3NC23CN(Cc2ccccc2OC(F)(F)F)C3)cc1] |
| 66 | 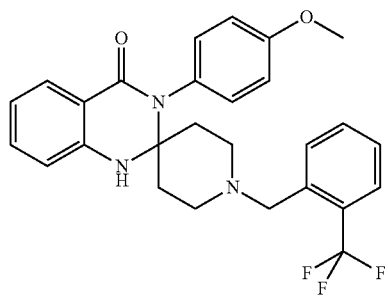 [SMILES: COc1ccc(N2C(=O)c3ccccc3NC23CCN(Cc2ccccc2C(F)(F)F)CC3)cc1] |

| Compound No. | Chemical Structure |
|---|---|
| 67 | 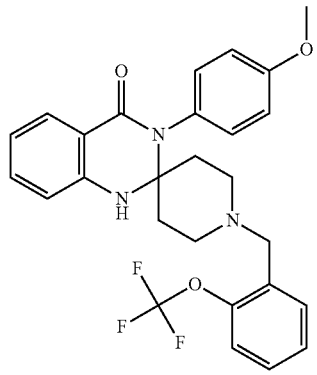 [SMILES: COc1ccc(N2C(=O)c3ccccc3NC23CCN(Cc2ccccc2OC(F)(F)F)CC3)cc1] |
| 68 | 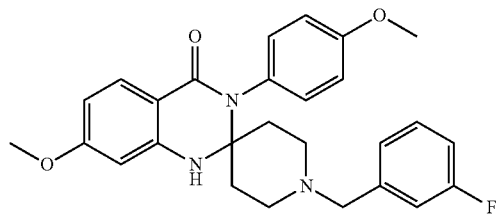 [SMILES: COc1ccc(N2C(=O)c3ccc(OC)cc3NC23CCN(Cc2cccc(F)c2)CC3)cc1] |
| 69 | 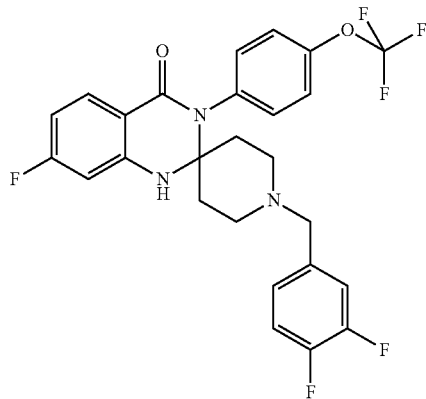 [SMILES: O=C1c2ccc(F)cc2NC2(CCN(Cc3ccc(F)c(F)c3)CC2)N1c1ccc(OC(F)(F)F)cc1] |
| 70 | 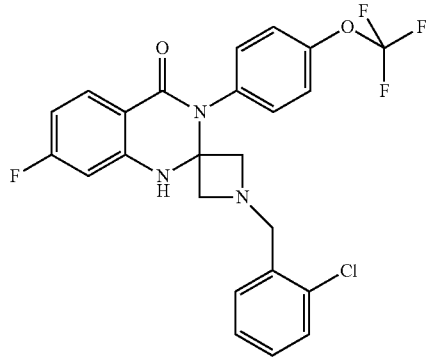 [SMILES: O=C1c2ccc(F)cc2NC2(CN(Cc3ccccc3Cl)C2)N1c1ccc(OC(F)(F)F)cc1] |

-continued
| Compound No. | Chemical Structure |
|---|---|
| 71 | 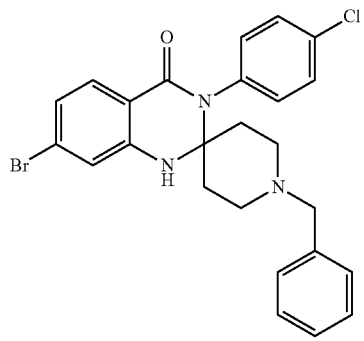 [SMILES: O=C1c2ccc(Br)cc2NC2(CCN(Cc3ccccc3)CC2)N1c1ccc(Cl)cc1] |
| 72 | 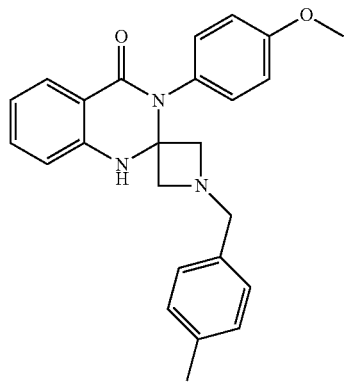 [SMILES: COc1ccc(N2C(=O)c3ccccc3NC23CN(Cc2ccc(C)cc2)C3)cc1] |
| 73 | 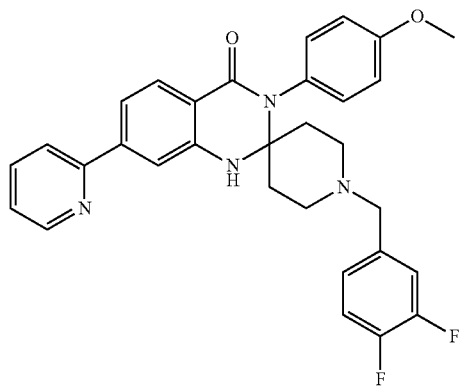 [SMILES: COc1ccc(N2C(=O)c3ccc(-c4ccccn4)cc3NC23CCN(Cc2ccc(F)c(F)c2)CC3)cc1] |
| 74 | 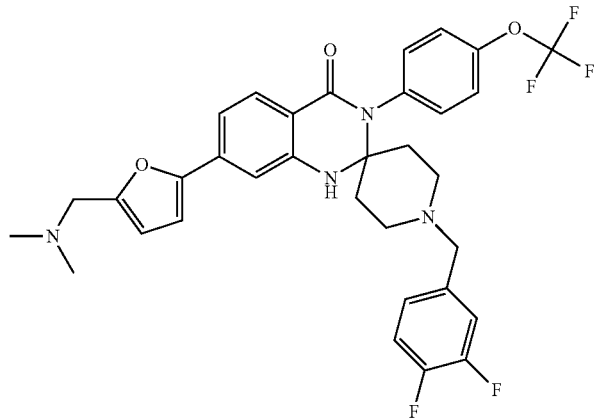 [SMILES: CN(C)Cc1ccc(-c2ccc3c(c2)NC2(CCN(Cc4ccc(F)c(F)c4)CC2)N(c2ccc(OC(F)(F)F)cc2)C3=O)o1] |

-continued
| Compound No. | Chemical Structure |
|---|---|
| 75 | 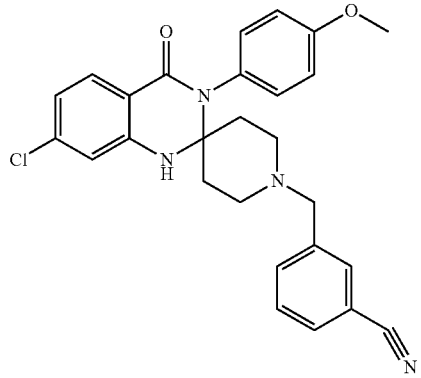 [SMILES: COc1ccc(N2C(=O)c3ccc(Cl)cc3NC23CCN(Cc2cccc(C#N)c2)CC3)cc1] |
| 76 | 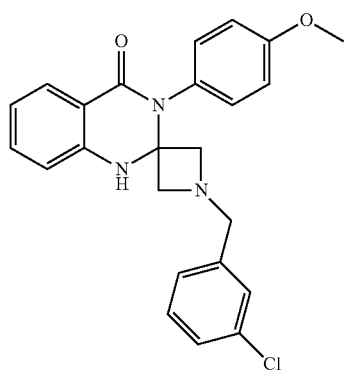 [SMILES: COc1ccc(N2C(=O)c3ccccc3NC23CN(Cc2cccc(Cl)c2)C3)cc1] |
| 77 | 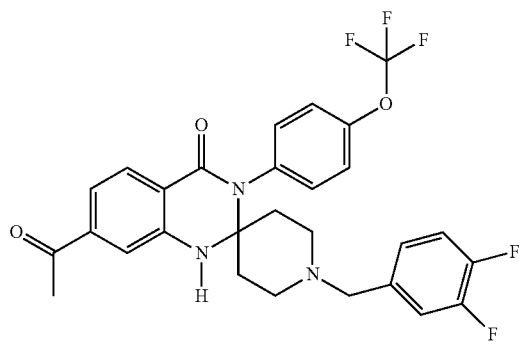 [SMILES: CC(=O)c1ccc2c(c1)NC1(CCN(Cc3ccc(F)c(F)c3)CC1)N(c1ccc(OC(F)(F)F)cc1)C2=O] |
| 78 | 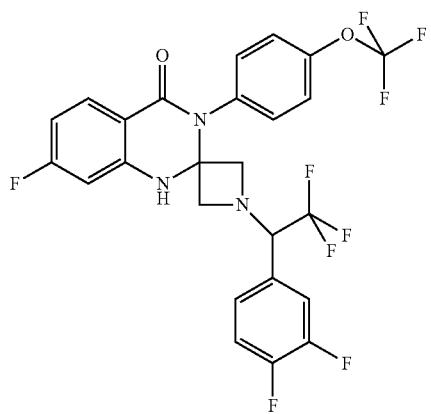 [SMILES: O=C1c2ccc(F)cc2NC2(CN(C(c3ccc(F)c(F)c3)C(F)(F)F)C2)N1c1ccc(OC(F)(F)F)cc1] |

| Compound No. | Chemical Structure |
|---|---|
| 79 | 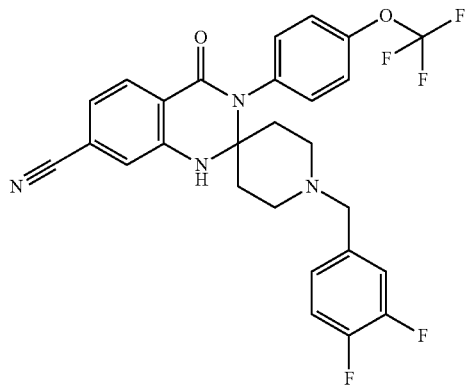 [SMILES: N#Cc1ccc2c(c1)NC1(CCN(Cc3ccc(F)c(F)c3)CC1)N(c1ccc(OC(F)(F)F)cc1)C2=O] |
| 80 | 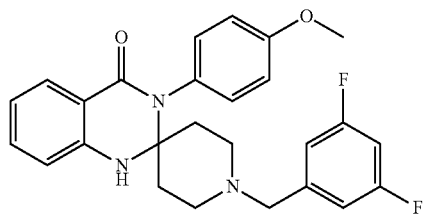 [SMILES: COc1ccc(N2C(=O)c3ccccc3NC23CCN(Cc2cc(F)cc(F)c2)CC3)cc1] |
| 81 | 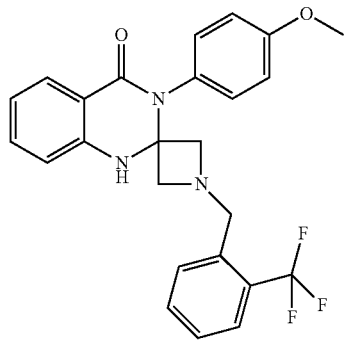 [SMILES: COc1ccc(N2C(=O)c3ccccc3NC23CN(Cc2ccccc2C(F)(F)F)C3)cc1] |
| 82 | 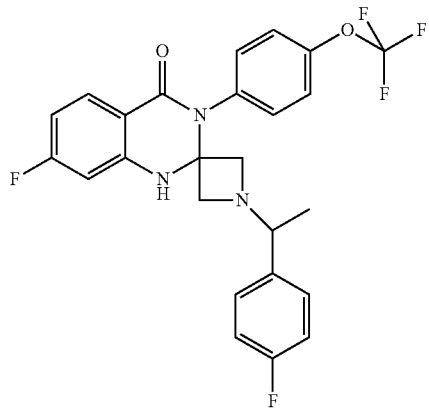 [SMILES: CC(c1ccc(F)cc1)N1CC2(C1)Nc1cc(F)ccc1C(=O)N2c1ccc(OC(F)(F)F)cc1] |

-continued
| Compound No. | Chemical Structure |
|---|---|
| 83 | 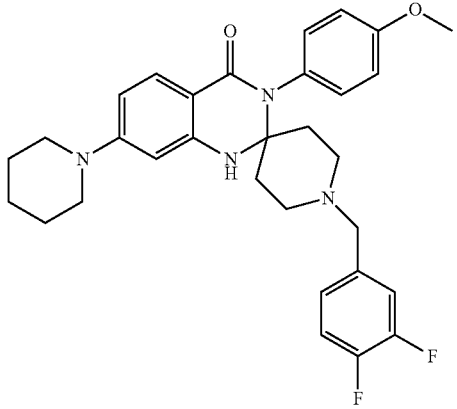 [SMILES: COc1ccc(N2C(=O)c3ccc(N4CCCCC4)cc3NC23CCN(Cc2ccc(F)c(F)c2)CC3)cc1] |
| 84 | 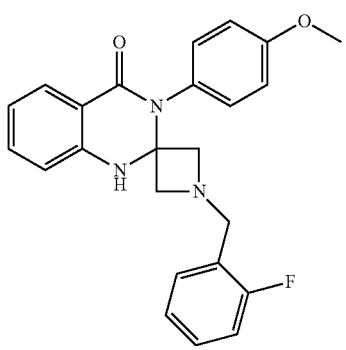 |
| 85 | 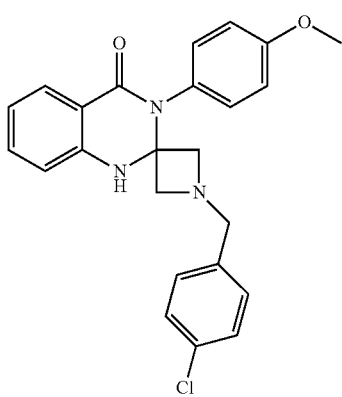 [SMILES: COc1ccc(N2C(=O)c3ccccc3NC23CN(Cc2ccc(Cl)cc2)C3)cc1] |
| 86 | 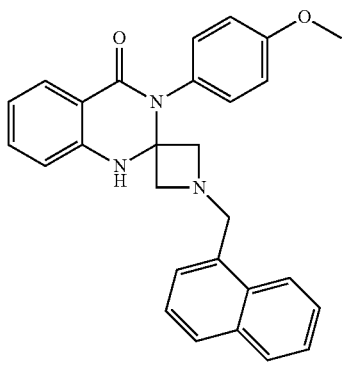 [SMILES: COc1ccc(N2C(=O)c3ccccc3NC23CN(Cc2cccc4ccccc24)C3)cc1] |

| Compound No. | Chemical Structure |
|---|---|
| 87 | 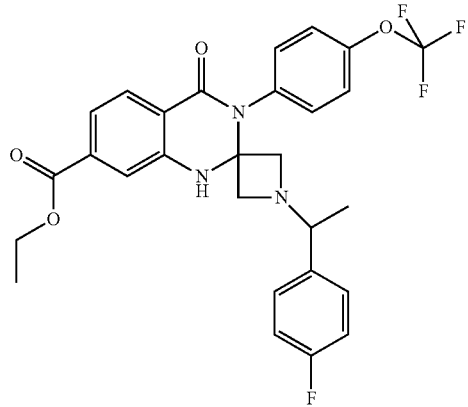 [SMILES: CCOC(=O)c1ccc2c(c1)NC1(CN(C(C)c3ccc(F)cc3)C1)N(c1ccc(OC(F)(F)F)cc1)C2=O] |
| 88 | 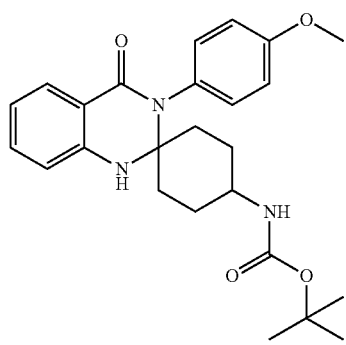 [SMILES: COc1ccc(N2C(=O)c3ccccc3NC23CCC(NC(=O)OC(C)(C)C)CC3)cc1] |
| 89 | 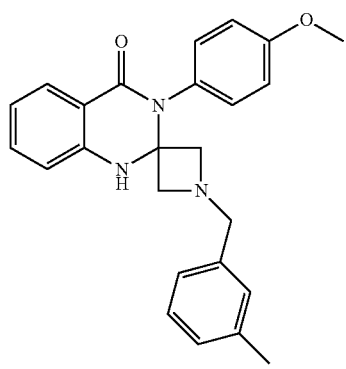 [SMILES: COc1ccc(N2C(=O)c3ccccc3NC23CN(Cc2cccc(C)c2)C3)cc1] |
| 90 | 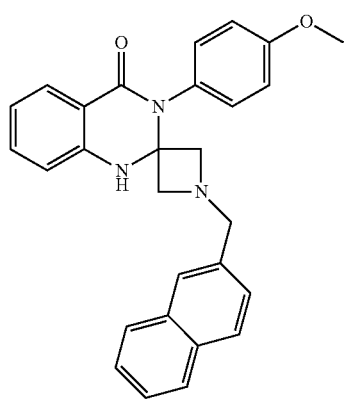 [SMILES: COc1ccc(N2C(=O)c3ccccc3NC23CN(Cc2ccc4ccccc4c2)C3)cc1] |

-continued
| Compound No. | Chemical Structure |
|---|---|
| 91 | 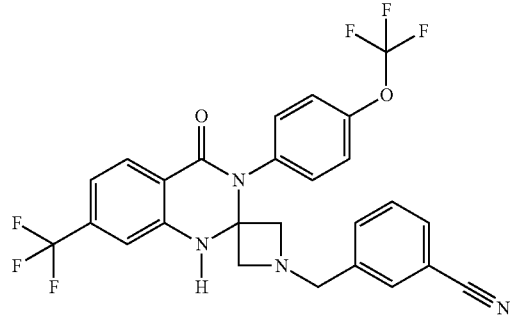 [SMILES: N#Cc1cccc(CN2CC3(C2)Nc2cc(C(F)(F)F)ccc2C(=O)N3c2ccc(OC(F)(F)F)cc2)c1] |
| 92 | 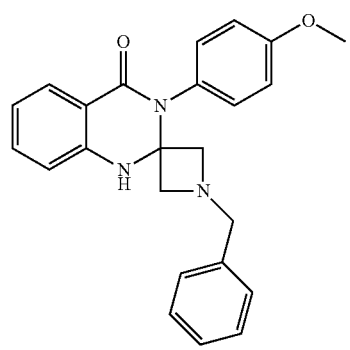 [SMILES: COc1ccc(N2C(=O)c3ccccc3NC23CN(Cc2ccccc2)C3)cc1] |
| 93 | 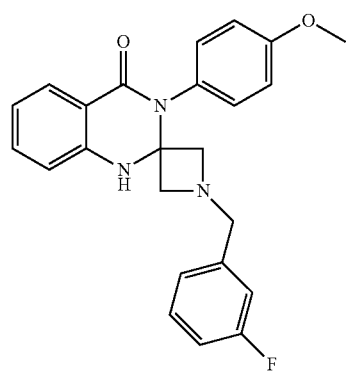 [SMILES: COc1ccc(N2C(=O)c3ccccc3NC23CN(Cc2cccc(F)c2)C3)cc1] |
| 94 | 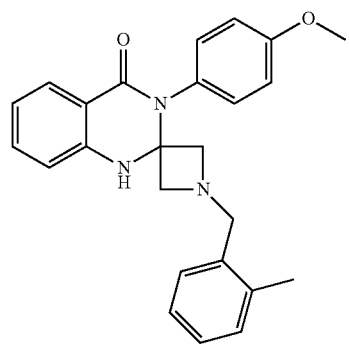 [SMILES: COc1ccc(N2C(=O)c3ccccc3NC23CN(Cc2ccccc2C)C3)cc1] |

| Compound No. | Chemical Structure |
|---|---|
| 95 | 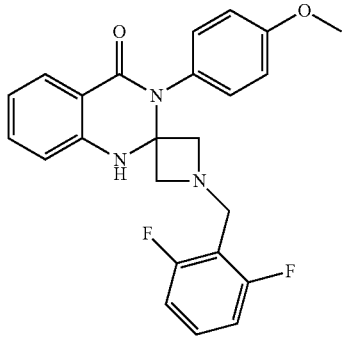 [SMILES: COc1ccc(N2C(=O)c3ccccc3NC23CN(Cc2c(F)cccc2F)C3)cc1] |
| 96 | 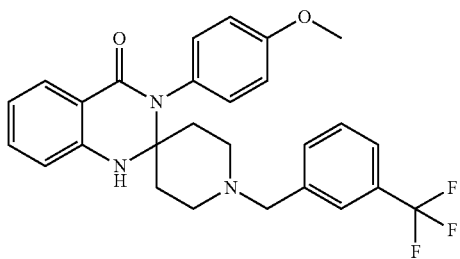 [SMILES: COc1ccc(N2C(=O)c3ccccc3NC23CCN(Cc2cccc(C(F)(F)F)c2)CC3)cc1] |
| 97 | 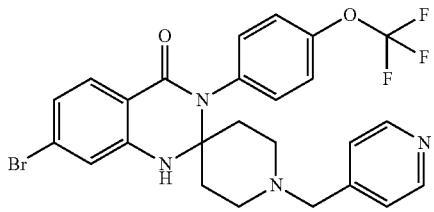 [SMILES: O=C1c2ccc(Br)cc2NC2(CCN(Cc3ccncc3)CC2)N1c1ccc(OC(F)(F)F)cc1] |
| 98 | 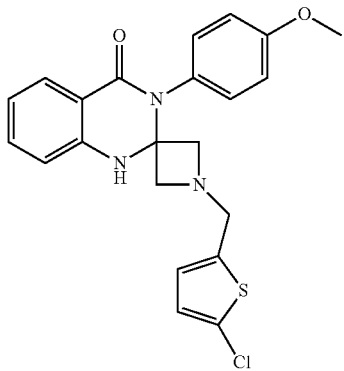 [SMILES: COc1ccc(N2C(=O)c3ccccc3NC23CN(Cc2ccc(Cl)s2)C3)cc1] |

-continued
| Compound No. | Chemical Structure |
|---|---|
| 99 | 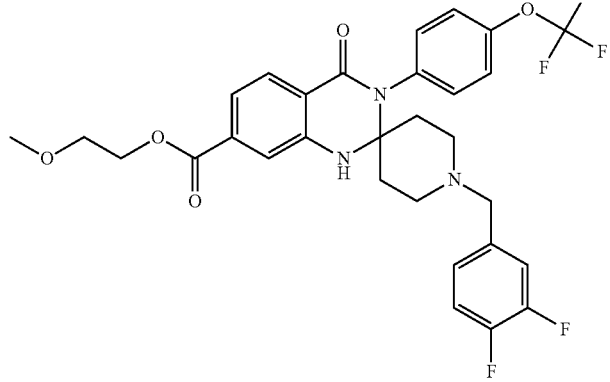 |
| 100 | 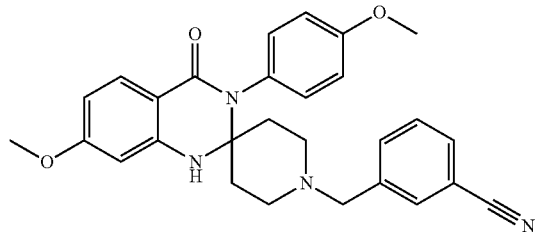 [SMILES: COc1ccc(N2C(=O)c3ccc(OC)cc3NC23CCN(Cc2cccc(C#N)c2)CC3)cc1] |
| 101 | 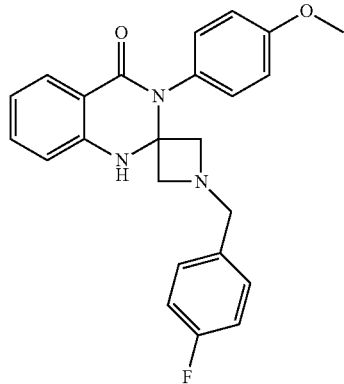 [SMILES: COc1ccc(N2C(=O)c3ccccc3NC23CN(Cc2ccc(F)cc2)C3)cc1] |
| 102 | 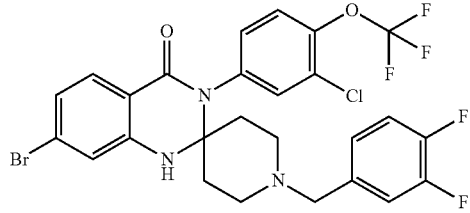 [SMILES: O=C1c2ccc(Br)cc2NC2(CCN(Cc3ccc(F)c(F)c3)CC2)N1c1ccc(OC(F)(F)F)c(Cl)c1] |
| 103 | 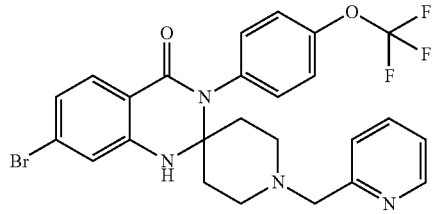 [SMILES: O=C1c2ccc(Br)cc2NC2(CCN(Cc3ccccn3)CC2)N1c1ccc(OC(F)(F)F)cc1] |

-continued
| Compound No. | Chemical Structure |
|---|---|
| 104 | 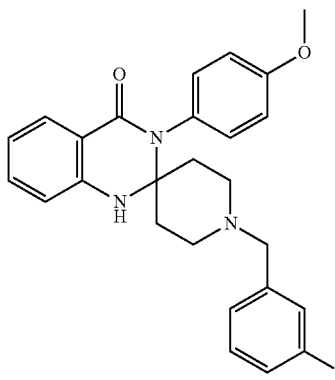 |
| 105 | 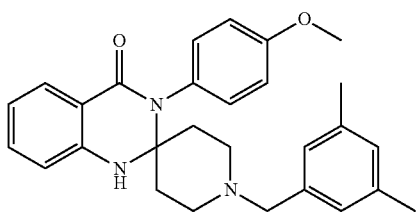 [SMILES: COc1ccc(N2C(=O)c3ccccc3NC23CCN(Cc2cc(C)cc(C)c2)CC3)cc1] |
| 106 | 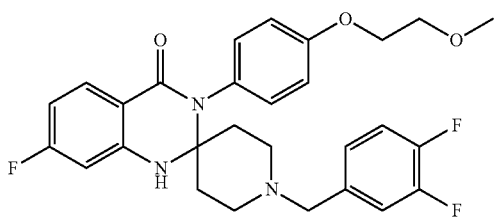 [SMILES: COCCOc1ccc(N2C(=O)c3ccc(F)cc3NC23CCN(Cc2ccc(F)c(F)c2)CC3)cc1] |
| 107 | 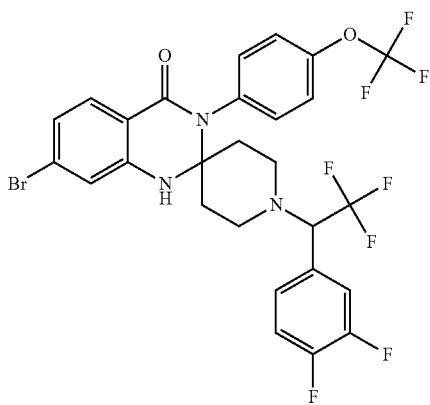 [SMILES: O=C1c2ccc(Br)cc2NC2(CCN(C(c3ccc(F)c(F)c3)C(F)(F)F)CC2)N1c1ccc(OC(F)(F)F)cc1] |

-continued
| Compound No. | Chemical Structure |
|---|---|
| 108 | 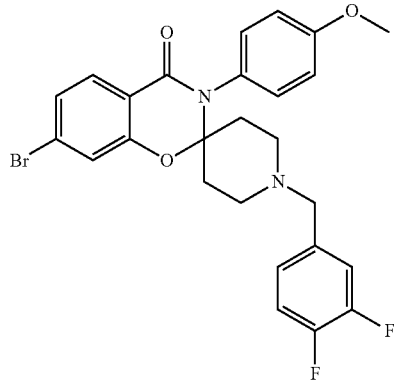 [SMILES: COc1ccc(N2C(=O)c3ccc(Br)cc3OC23CCN(Cc2ccc(F)c(F)c2)CC3)cc1] |
| 109 | 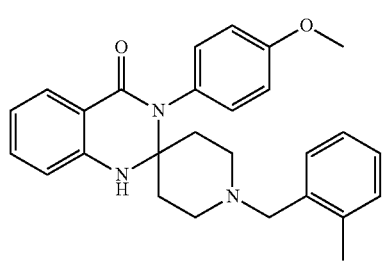 [SMILES: COc1ccc(N2C(=O)c3ccccc3NC23CCN(Cc2ccccc2C)CC3)cc1] |
| 110 | 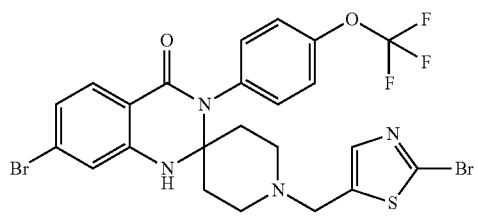 [SMILES: O=C1c2ccc(Br)cc2NC2(CCN(Cc3cnc(Br)s3)CC2)N1c1ccc(OC(F)(F)F)cc1] |
| 111 | 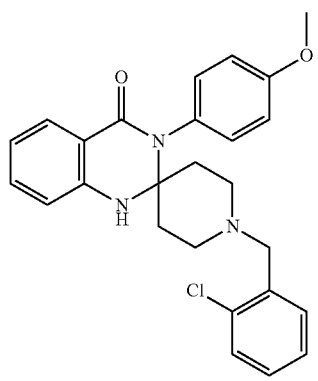 |

-continued
| Compound No. | Chemical Structure |
|---|---|
| 112 | 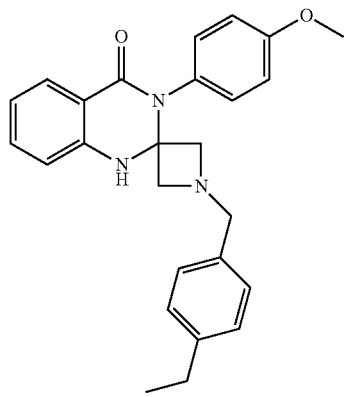 [SMILES: CCc1ccc(CN2CC3(C2)Nc2ccccc2C(=O)N3c2ccc(OC)cc2)cc1] |
| 113 | 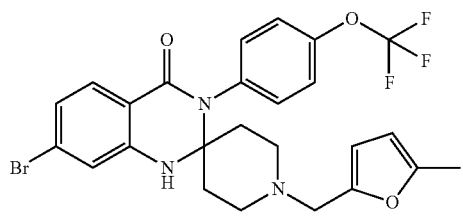 [SMILES: Cc1ccc(CN2CCC3(CC2)Nc2cc(Br)ccc2C(=O)N3c2ccc(OC(F)(F)F)cc2)o1] |
| 114 | 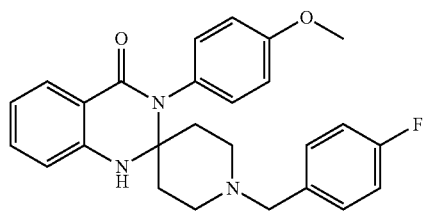 [SMILES: COc1ccc(N2C(=O)c3ccccc3NC23CCN(Cc2ccc(F)cc2)CC3)cc1] |
| 115 | 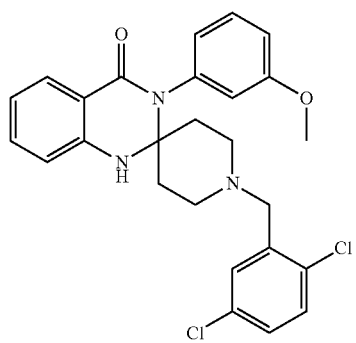 [SMILES: COc1cccc(N2C(=O)c3ccccc3NC23CCN(Cc2cc(Cl)ccc2Cl)CC3)c1] |
| 116 | 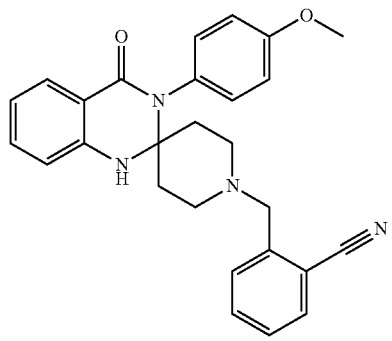 [SMILES: COc1ccc(N2C(=O)c3ccccc3NC23CCN(Cc2ccccc2C#N)CC3)cc1] |

-continued

| Compound No. | Chemical Structure |
|---|---|
| 117 | 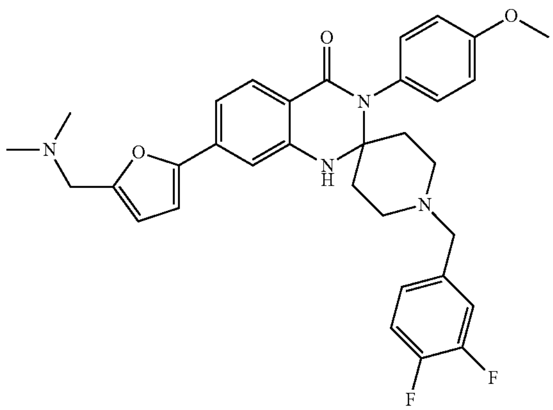 |
| 118 | 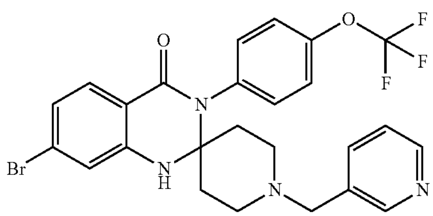 [SMILES: O=C1c2ccc(Br)cc2NC2(CCN(Cc3cccnc3)CC2)N1c1ccc(OC(F)(F)F)cc1] |
| 119 | 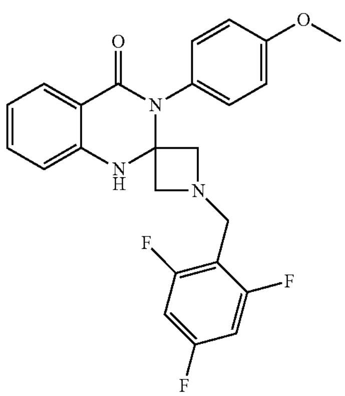 [SMILES: COc1ccc(N2C(=O)c3ccccc3NC23CN(Cc2c(F)cc(F)cc2F)C3)cc1] |
| 120 | 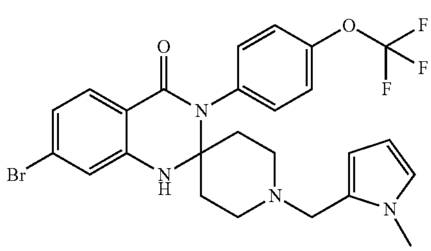 [SMILES: Cn1cccc1CN1CCC2(CC1)Nc1cc(Br)ccc1C(=O)N2c1ccc(OC(F)(F)F)cc1] |
| 121 | 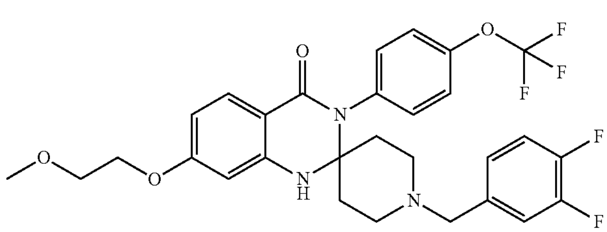 [SMILES: COCCOc1ccc2c(c1)NC1(CCN(Cc3ccc(F)c(F)c3)CC1)N(c1ccc(OC(F)(F)F)cc1)C2=O] |

| Compound No. | Chemical Structure |
|---|---|
| 122 | 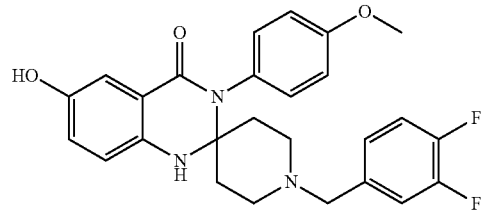 [SMILES: COc1ccc(N2C(=O)c3cc(O)ccc3NC23CCN(Cc2ccc(F)c(F)c2)CC3)cc1] |
| 123 | 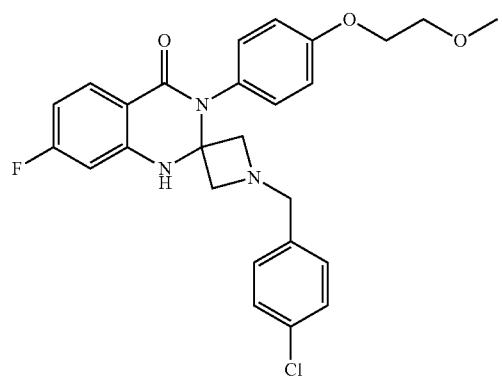 [SMILES: COCCOc1ccc(N2C(=O)c3ccc(F)cc3NC23CN(Cc2ccc(Cl)cc2)C3)cc1] |
| 124 | 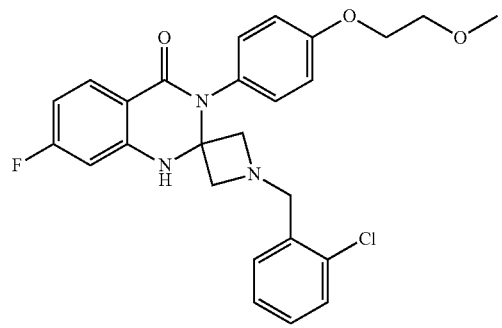 [SMILES: COCCOc1ccc(N2C(=O)c3ccc(F)cc3NC23CN(Cc2ccccc2Cl)C3)cc1] |
| 126 | 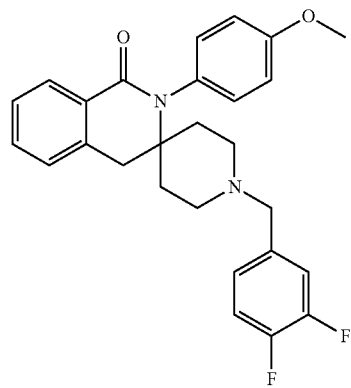 [SMILES: COc1ccc(N2C(=O)c3ccccc3CC23CCN(Cc2ccc(F)c(F)c2)CC3)cc1] |

| Compound No. | Chemical Structure |
|---|---|
| 127 | 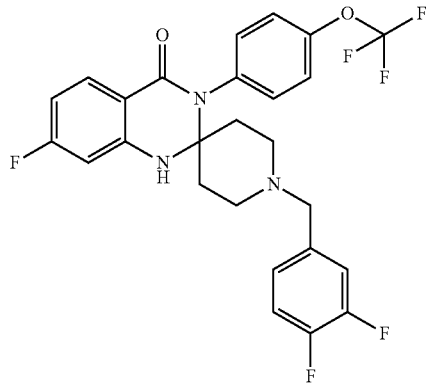 [SMILES: O=C1c2ccc(F)cc2NC2(CCN(Cc3ccc(F)c(F)c3)CC2)N1c1ccc(OC(F)(F)F)cc1] | and the physiologically acceptable salts, solvates, tautomers and stereoisomers thereof, including mixtures thereof in all ratios.

13. A pharmaceutical composition comprising a therapeutically effective amount of at least one compound according to claim 1, optionally further comprising at least one additional compound selected from the group consisting of physiologically acceptable excipients, auxiliaries, adjuvants, diluents, carriers and/or additional pharmaceutically active substance other than the compound according to claim 1.

14. A medicament comprising at least one compound according to claim 1.

15. A medicament comprising at least one compound according to claim 1 for the treatment of physiological and/or pathophysiological conditions selected from the group consisting of conditions which are affected or facilitated by the neuromodulatory effect of mGluR4 allosteric modulators, central nervous system disorders, addiction, tolerance or dependence, affective disorders selected from the group consisting of anxiety, agoraphobia, generalized anxiety disorder (GAD), obsessive-compulsive disorder (OCD), panic disorder, post-traumatic stress disorder (PTSD), social phobia, other phobias, substance-induced anxiety disorder, and acute stress disorder, mood disorders, bipolar disorders (I & II), cyclothymic disorder, depression, dysthymic disorder, major depressive disorder, and substance-induced mood disorder, psychiatric disease selected from the group consisting of psychotic disorders and attention-deficit/hyperactivity disorder, Parkinson's disease, and movement disorders selected from the group consisting of bradykinesia, rigidity, dystonia, drug-induced parkinsonism, dyskinesia, tardive dyskinesia, L-DOPA-induced dyskinesia, dopamine agonist-induced dyskinesia, hyperkinetic movement disorders, Gilles de la Tourette syndrome, resting tremor, action tremor, akinesia, akinetic-rigid syndrome, akathisia, athetosis, asterixis, tics, postural instability, postencephalitic parkinsonism, muscle rigidity, chorea and choreaform movements, spasticity, myoclonus, hemiballismus, progressive supranuclear palsy, restless legs syndrome, and periodic limb movement disorder, cognitive disorders selected from the group consisting of delirium, substance-induced persisting delirium, dementia, dementia due to HIV disease, dementia due to Huntington's disease, dementia due to Parkinson's disease, Parkinsonian-ALS demential complex, dementia of the Alzheimer's type, substance-induced persisting dementia, and mild cognitive impairment, neurological disorders selected from the group consisting of neurodegeneration, neurotoxicity or ischemia selected from the group consisting of stroke, spinal cord injury, cerebral hypoxia, intracranial hematoma, memory impairment, Alzheimer's disease, dementia, delirium tremens, other forms of neurodegeneration, neurotoxicity, and ischemia, inflammation and/or neurodegeneration resulting from traumatic brain injury, inflammatory central nervous system disorders selected from the group consisting of multiple sclerosis, benign multiple sclerosis, relapsing-remitting multiple sclerosis, secondary progressive multiple sclerosis, primary progressive multiple sclerosis, and progressive-relapsing multiple sclerosis, migraine, epilepsy and tremor, temporal lobe epilepsy, epilepsy secondary to another disease or injury selected from the group consisting of chronic encephalitis, traumatic brain injury, stroke or ischemia, medulloblastomas, inflammatory or neuropathic pain, metabolic disorders associated with glutamate dysfunction, type 2 diabetes, diseases or disorders of the retina, retinal degeneration or macular degeneration, diseases or disorders of the gastrointestinal tract, gastroesophageal reflux disease (GERD), lower esophageal sphincter diseases or disorders, diseases of gastrointestinal motility, colitis, Crohn's disease or irritable bowel syndrome (IBS), or cancers.

16. The medicament according to claim 14, wherein such medicament comprises at least one additional pharmacologically active substance.

17. The medicament according to claim 14, wherein the medicament is applied before and/or during and/or after treatment with at least one additional pharmacologically active substance.

18. A kit comprising a therapeutically effective amount of at least one compound according to claim 1 and a therapeutically effective amount of at least one further pharmacologically active substance other than the compound according to claim 1.

19. A method for modulating metabotropic glutamate receptor subtype 4 (mGluR4) and/or altering glutamate level or glutamatergic signalling comprising administering an effective amount to a patient in need thereof a compound of claim 1.

20. Process for manufacturing a compound of formula (I) comprising the steps of:

(a) reacting a compound of formula (II)

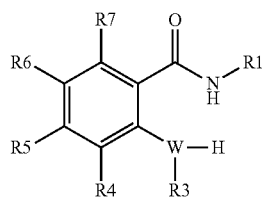

(II)

wherein
W, R1, R3, R4, R5, R6, R7 are as defined in claim 1,
with a compound of formula (III)

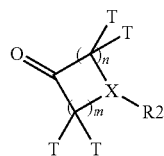

(III)

wherein
X, R2, T, n, m are as defined in claim 1,
to yield the compound of formula (I)

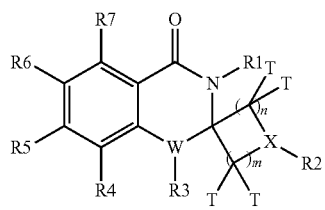

(I)

wherein
W, X, R1, R2, R3, R4, R5, R6, R7, T, n, m are as defined in claim 1,
or
(b) reacting a compound of formula (IV)

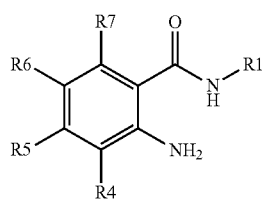

(IV)

wherein
R1, R4, R5, R6, R7 are as defined in claim 1,
with a compound of formula (III)

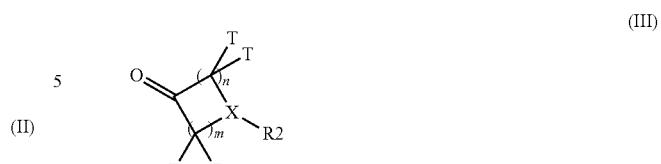

(III)

wherein
X, R2, T, n, m are as defined in claim 1,
to yield the compound of formula (I)

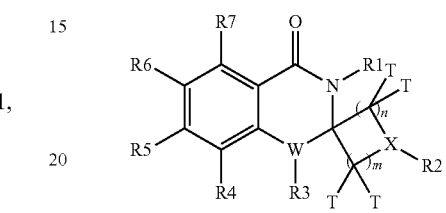

(I)

wherein
X, R1, R2, R4, R5, R6, R7, T, n, m are as defined in claim 1 and W is N and R3 is H;
or
(c) reacting a compound of formula (V)

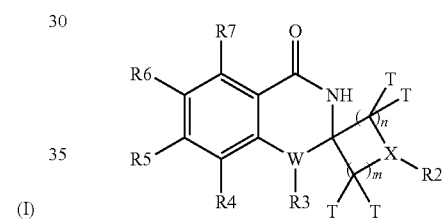

(V)

wherein
W, X, R2, R3, R4, R5, R6, R7, T, n, m are as defined in claim 1,
with a compound of formula (VI)

Z—R1 (VI)

wherein
Z denotes halogen, boronic acid or a ester of boronic acid and
R1 is as defined in claim 1,
to yield the compound of formula (I)

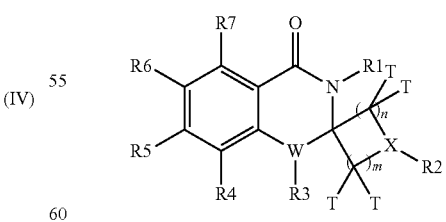

(I)

wherein
W, X, R1, R2, R3, R4, R5, R6, R7, T, n, m are as defined in claim 1;
and optionally
(d) converting a base or an acid of the compound of formula (I) into a salt thereof.

21. The compound of formula (125):
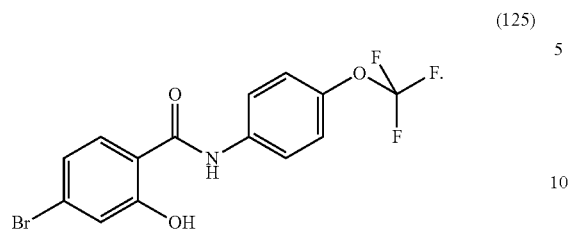
(125)
* * * * *